(12) United States Patent
Zheng et al.

(10) Patent No.: US 7,348,343 B2
(45) Date of Patent: Mar. 25, 2008

(54) AMIDES USEFUL FOR TREATING PAIN

(75) Inventors: Guo Zhu Zheng, Lake Bluff, IL (US);
Brian S. Brown, Evanston, IL (US);
Sean C. Turner, Mannheim (DE);
Tammie K. White, Gurnee, IL (US);
Robert G. Schmidt, Waukegan, IL (US); John R. Koenig, Chicago, IL (US); Chih-Hung Lee, Vernon Hills, IL (US)

(73) Assignee: Abbott Laboratories Inc., Abbott Park, IL (US)

( * ) Notice: Subject to any disclaimer, the term of this patent is extended or adjusted under 35 U.S.C. 154(b) by 0 days.

(21) Appl. No.: 11/521,807

(22) Filed: Sep. 15, 2006

(65) Prior Publication Data

US 2007/0010557 A1    Jan. 11, 2007

Related U.S. Application Data

(62) Division of application No. 10/887,383, filed on Jul. 8, 2004, now Pat. No. 7,129,235.

(60) Provisional application No. 60/486,548, filed on Jul. 11, 2003.

(51) Int. Cl.
C07D 401/14    (2006.01)
A61K 31/444   (2006.01)

(52) U.S. Cl. ............... 514/334; 514/256; 514/333; 544/333; 546/256; 546/257

(58) Field of Classification Search ........... 544/333; 546/256, 257; 514/256, 333, 334
See application file for complete search history.

(56) References Cited

FOREIGN PATENT DOCUMENTS

| EP | 1 437 344 | 7/2004 |
|---|---|---|
| JP | 2003/192673 | 7/2003 |
| WO | 02/08221 | 1/2002 |
| WO | 03/066595 | 8/2003 |
| WO | 03/074520 | 9/2003 |
| WO | 2004/011441 | 2/2004 |

OTHER PUBLICATIONS

Caterina, et al., "Impaired Nociception and Pain Sensation in Mice Lacking the Capsaicin Receptor," Science 288:306-313 (2000).
Caterina, et al., "The capsaicin receptor: a heat-activated ion channel in the pain pathway," Nature 389:816-824 (1997).
Caterina, et al., "The Vanilloid Receptor: A Molecular Gateway to the Pain Pathway," Annual Review of Neuroscience 24:487-517 (2001).
Collier et al., "The abdominal constriction response and its suppression by analgesic drugs in the mouse," Br. J. Pharmac. Chemother. 32:295-310 (1968).
Database Chemcats Apr. 23, 2003, retrieved from STN Database accession No. 2003: 3693665; 2003:3693659, 2003: 3693658 and other compounds from AsInEx Express Platinum Collection abstract.
Davis, et al., "Vanilloid receptor-1 is essential for inflammatory thermal hyperalgesia," Nature 405:183-187 (2000).
Fowler, "Intravesical treatment of overactive bladder," Urology 55(Supp 5A):60-64 (2000).
Hayes, et al., "Cloning and functional expression of a human orthologue of rat vanilloid receptor-1," Pain 88:205-215 (2000).
Nolano, et al., "Topical capsaicin in humans: parallel loss of epidermal nerve fibers and pain sensation," Pain 81:135-145 (1999).
Pircio, A New Method for the Evaluation of Analgesic Activity using Adjuvant-Induced Arthritis in the Rat, European J. of Pharmacology, V 31 pp. 207-215 (1975).
Poste, Lipid Vesicles as Carriers for Introducing Biologically Active Materials into Cells, Methods in Cell Biology, vol. XIV, pp. 33-71 (1976).
Patent Abstracts of Japan, vol. 2003, No. 11, Nov. 2003.

*Primary Examiner*—Zinna N. Davis
(74) *Attorney, Agent, or Firm*—Sonali S. Srivastava

(57) ABSTRACT

The present invention relates to compounds of formula (I-VII)

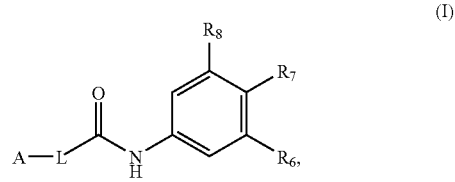

or a pharmaceutically acceptable salt or prodrug thereof, in which A, L, $R_6$, $R_7$ and $R_8$ are defined herein. The present invention also relates to methods of treating pain using these compounds and pharmaceutical compositions including these compounds.

11 Claims, No Drawings

AMIDES USEFUL FOR TREATING PAIN

This is a divisional of U.S. patent application Ser. No.10/887,383, filed Jul. 8, 2004, now U.S. Pat. No. 7,129,235 incorporated herein by reference, and which claims priority from U.S. Provisional Application Ser. No. 60/486,548 filed on Jul. 11, 2003.

TECHNICAL FIELD

The present invention relates to compounds of formula (I-VII) that are useful for treating pain, pharmaceutical compositions containing compounds of formula (I-VII) that are useful in treating pain, and methods of treating pain using compounds of formula (I-VII).

BACKGROUND OF INVENTION

Pain continues to produce severe distress in people's lives, dominating and disrupting their quality of life. Much of the currently available clinical treatment is only partially effective and may be accompanied by distressing side effects or have abuse potential. The unmet clinical need, the personal suffering, and societal economic costs of pain are substantial. The lack of success in clinical pain therapy exemplifies the need for the discovery of new analgesics.

The present invention relates to novel compounds useful as analgesics.

SUMMARY OF THE PRESENT INVENTION

The present invention discloses novel amides, a method for controlling pain in mammals, and pharmaceutical compositions including those amides. More particularly, the present invention is directed to compounds of general formula (I)

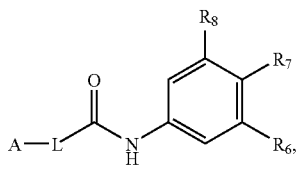

(I)

or a pharmaceutically acceptable salt or prodrug thereof, wherein

A is

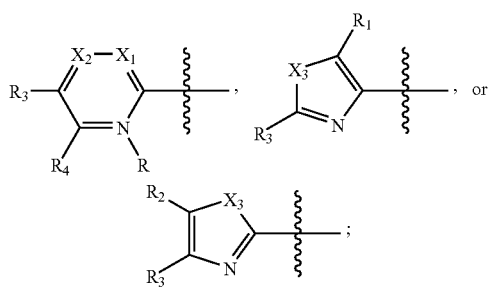

$X_1$ is N or $CR_1$;
$X_2$ is N or $CR_2$;
$X_3$ is O or S;
R is absent or O;
$R_1$ is hydrogen, lower alkoxy, lower alkenyl, lower alkyl, lower alkylthio, lower alkynyl, lower haloalkoxy, lower haloalkyl, lower haloalkylthio, halogen, hydroxy, mercapto, nitro, $R_AR_BNS(O)_2$— or $R_AR_BN$—;
$R_2$, $R_3$, and $R_4$ are independently hydrogen or halogen;
$R_7$ is hydrogen, alkenyl, alkoxy, alkoxycarbonyl, alkoxysulfonyl, alkyl, alkylcarbonyl, alkoxycarbonylalkyl, alkylsulfonyl, alkylthio, alkynyl, aryl, arylalkyl, aryloxy, arylthio, cyanoalkyl, cycloalkyl, cycloalkylalkyl, cycloalkyloxy, cycloalkylthio, haloalkoxy, haloalkyl, haloalkylsulfonyl, haloalkylthio, halogen, heteroaryl, heteroarylalkyl, heteroaryloxy, heteroarylthio, heterocycle, heterocyclealkyl, hydroxy, hydroxyalkyl, —$R_CR_DN$—, $(R_AR_BN)$carbonyl-, $(R_AR_BN)$sulfonyl-; or $R_AS(O)_2$;
$R_6$ and $R_8$ are independently hydrogen, lower alkenyl, lower alkoxy, lower alkyl, lower alkylthio, lower alkynyl, lower haloalkoxy, lower haloalkyl, lower haloalkylthio, halogen, hydroxy, mercapto, or $R_AR_BN$—;
alternatively, $R_7$ and $R_6$ taken together with the atoms they are attached can form a ring selected from the group consisting of 2,2,3,3-tetrafluoro-2,3-dihydro-benzo[1,4]dioxinyl; 2,3-tetrahydro-benzo[1,4]dioxinyl; 2,2-difluoro-benzo[1,3]dioxolyl; and 2,2-dihydro-benzo[1,3]dioxolyl;
$R_A$ and $R_B$ are independently alkyl, hydrogen, haloalkyl, or heterocycle;
$R_C$ and $R_D$ are independently hydrogen, alkenyl, alkoxycarbonyl, alkyl, alkylcarbonyl, alkynyl, or $(R_AR_BN)$carbonyl;
L is

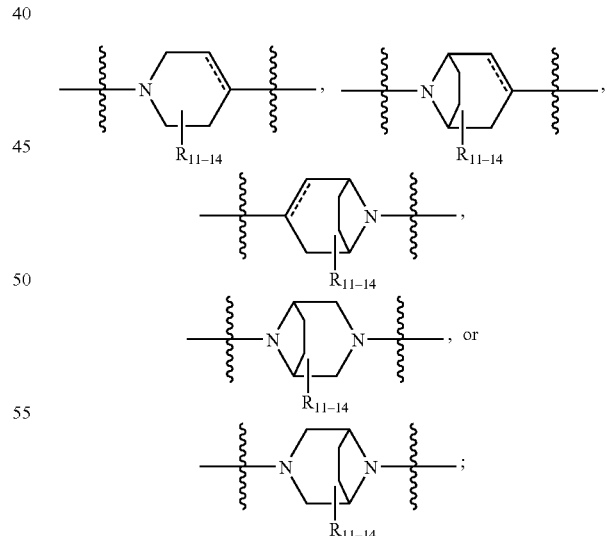

—is absent or a single bond; and
$R_{11}$, $R_{12}$, $R_{13}$, and $R_{14}$ are independently hydrogen, alkoxy, alkyl, or hydroxy.

Also, the present invention is directed to compounds of general formula (III)

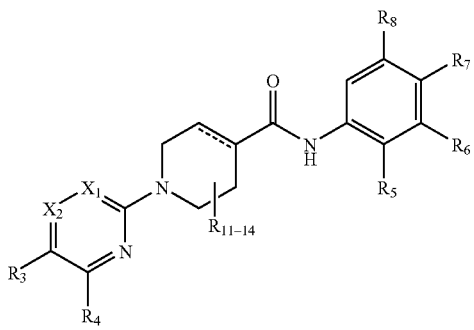

(III)

—is a single bond;
X₁ is CR₁;
X₂ is CR₂;
R₁ is hydrogen, lower haloalkyl or halogen;
R₂, R₃, R₄, and R₆, are hydrogen;
R₅ is alkyl, hydrogen, halogen, alkoxy, or haloalkoxy;
R₇ is alkoxy, alkyl, alkylthio, cycloalkyl, haloalkoxy, haloalkyl, haloalkylsulfonyl, haloalkylthio, halogen, R$_C$R$_D$N—; or R$_A$S(O)₂—;
R₁₁, R₁₂, R₁₃, and R₁₄ are hydrogen; and
R₄, R$_C$ and R$_D$ are independently hydrogen or alkyl.

Also, the present invention is directed to compounds of general formula (VI)

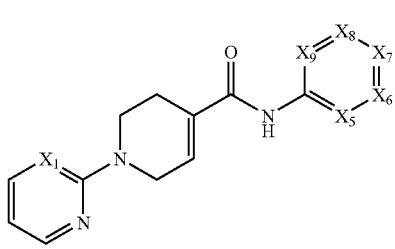

(VII)

wherein
X₁ is N or CR₁;
X₅ is N or CR₅;
X₆ is a bond or CR₆;
X₇ is N or CR₇;
X₈ is N or CR₈;
X₉ is N or CR₉;
R₁, R₅, and R₉ are independently selected from the group consisting of hydrogen, alkyl, alkoxy, halogen, haloalkyl and heterocycle;
R₇ is hydrogen, alkenyl, alkoxy, alkoxycarbonyl, alkoxysulfonyl, alkyl, alkylcarbonyl, alkoxycarbonylalkyl, alkylsulfonyl, alkylthio, alkynyl, aryl, arylalkyl, aryloxy, arylthio, cyanoalkyl, cycloalkyl, cycloalkylalkyl, cycloalkyloxy, cycloalkylthio, haloalkoxy, haloalkyl, haloalkylsulfonyl, haloalkylthio, halogen, heteroaryl, heteroarylalkyl, heteroaryloxy, heteroarylthio, heterocycle, heterocyclealkyl, hydroxy, hydroxyalkyl, —R$_C$R$_D$N—, (R$_A$R$_B$N)carbonyl-, (R$_A$R$_B$N)sulfonyl-; or R$_A$S(O)₂—;

R₆ and R₈ are independently hydrogen, lower alkenyl, lower alkoxy, lower alkyl, lower alkylthio, lower alkynyl, lower haloalkoxy, lower haloalkyl, lower haloalkylthio, halogen, hydroxy, mercapto, or R$_A$R$_B$N—;

R$_A$ and R$_B$ are independently alkyl, hydrogen, haloalkyl, or heterocycle; and R$_C$ and R$_D$ are independently hydrogen, alkenyl, alkoxycarbonyl, alkyl, alkylcarbonyl, alkynyl, or (NR$_A$R$_B$)carbonyl.

DETAILED DESCRIPTION OF THE PRESENT INVENTION (1) Embodiments

In the principal embodiment, compounds of formula (I) are disclosed

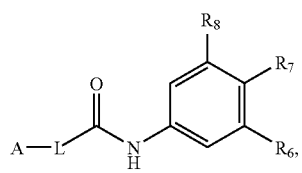

(I)

or a pharmaceutically acceptable salt or prodrug thereof, wherein
A is

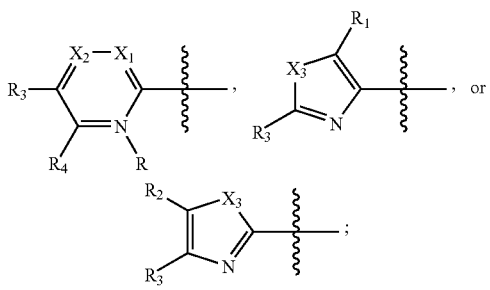

X₁ is N or CR₁;
X₂ is N or CR₂;
X₃ is O or N;
R is absent or O;
R₁ is hydrogen, lower alkoxy, lower alkenyl, lower alkyl, lower alkylthio, lower alkynyl, lower haloalkoxy, lower haloalkyl, lower haloalkylthio, halogen, hydroxy, mercapto, nitro, or R$_A$R$_B$NS(O)₂— or R$_A$R$_B$N—;
R₂, R₃, and R₄ are independently hydrogen or halogen;
R₇ is hydrogen, alkenyl, alkoxy, alkoxycarbonyl, alkoxysulfonyl, alkyl, alkylcarbonyl, alkxycarbonylalkyl, alkylsulfonyl, alkylthio, alkynyl, aryl, arylalkyl, aryloxy, arylthio, cyanoalkyl, cycloalkyl, cycloalkylalkyl, cycloalkyloxy, cycloalkylthio, haloalkoxy, haloalkyl, haloalkylsulfonyl, haloalkylthio, halogen, heteroaryl, heteroarylalkyl, heteroaryloxy, heteroarylthio, heterocycle, heterocyclealkyl, hydroxy, hydroxyalkyl, —R$_C$R$_D$N—, (R$_A$R$_B$N)carbonyl-, (R$_A$R$_B$N)sulfonyl-; or R$_A$S(O)₂.

R₆ and R₈ are independently hydrogen, lower alkenyl, lower alkoxy, lower alkyl, lower alkylthio, lower alkynyl, lower haloalkoxy, lower haloalkyl, lower haloalkylthio, halogen, hydroxy, mercapto, or R$_A$R$_B$N—;

alternatively, $R_7$ and $R_6$ taken together with the atoms they are attached can form a ring selected from the group consisting of 2,2,3,3-tetrafluoro-2,3-dihydro-benzo[1,4]dioxinyl; 2,3-tetrahydro-benzo[1,4]dioxinyl; 2,2-difluoro-benzo[1,3]dioxolyl; and 2,2-dihydro-benzo[1,3]dioxolyl;

$R_A$ and $R_B$ are independently alkyl, hydrogen, haloalkyl, or heterocycle;

$R_C$ and $R_D$ are independently hydrogen, alkenyl, alkoxycarbonyl, alkyl, alkylcarbonyl, alkynyl, or $(R_A R_B N)$carbonyl;

L is

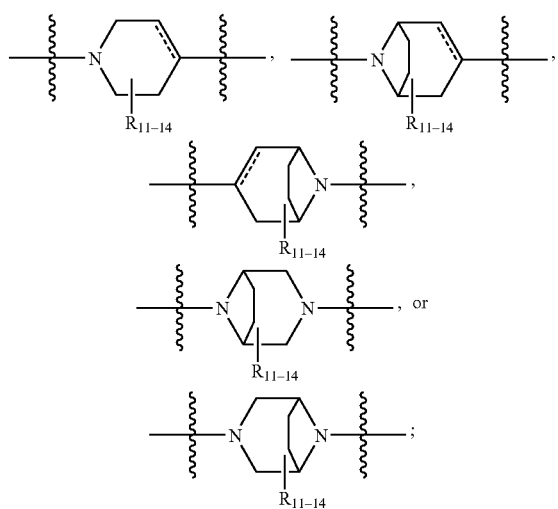

—is absent or a single bond; and $R_{11}$, $R_{12}$, $R_{13}$, and $R_{14}$ are independently hydrogen, alkoxy, alkyl, or hydroxy.

Another embodiment of the present invention relates to compounds of formula (II)

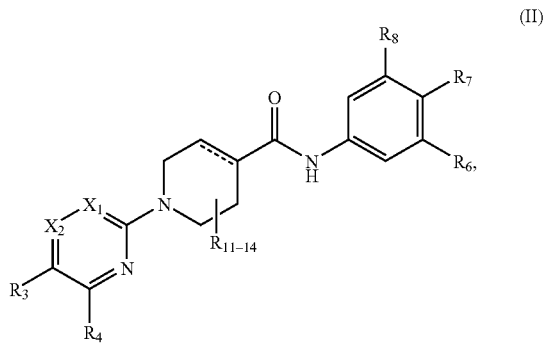

or a pharmaceutically acceptable salt or prodrug thereof wherein —is absent or a single bond; $X_1$ is N or $CR_1$; $X_2$ is N or $CR_2$; $R_1$ is hydrogen, lower alkoxy, lower alkenyl, lower alkyl, lower alkylthio, lower alkynyl, lower haloalkoxy, lower haloalkyl, lower haloalkylthio, halogen, hydroxy, mercapto, nitro, or $R_A R_B N$—; $R_2$, $R_3$, and $R_4$ are independently hydrogen or halogen; $R_7$ is hydrogen, alkenyl, alkoxy, alkoxycarbonyl, alkoxysulfonyl, alkyl, alkylcarbonyl, alkylsulfonyl, alkylthio, alkynyl, aryl, arylalkyl, aryloxy, arylthio, cycloalkyl, cycloalkylalkyl, cycloalkyloxy, cycloalkylthio, haloalkoxy, haloalkyl, haloalkylsulfonyl, haloalkylthio, halogen, heteroaryl, heteroarylalkyl, heteroaryloxy, heteroarylthio, heterocycle, heterocyclealkyl, hydroxy, hydroxyalkyl, $R_C R_D N$, $(R_A R_B N)$carbonyl, or $(R_A R_B N)$sulfonyl; $R_6$ and $R_8$ are independently hydrogen, lower alkenyl, lower alkoxy, lower alkyl, lower alkylthio, lower alkynyl, lower haloalkoxy, lower haloalkyl, lower haloalkylthio, halogen, hydroxy, mercapto, or $R_A R_B N$—; $R_A$ and $R_B$ are independently hydrogen or alkyl; $R_C$ and $R_D$ are independently hydrogen, alkenyl, alkoxycarbonyl, alkyl, alkylcarbonyl, alkynyl, or $(R_A R_B N)$carbonyl; and $R_{11}$, $R_{12}$, $R_{13}$, and $R_{14}$ are independently hydrogen, alkoxy, alkyl, or hydroxy.

Another embodiment of the present invention relates to compounds of formula (II) wherein —is a single bond; $X_1$ is $CR_1$; $X_2$ is $CR_2$; $R_1$ is lower haloalkyl or halogen; $R_2$, $R_3$, and $R_4$ are hydrogen; $R_7$ is alkoxy, alkyl, alkylthio, alkylcarbonyl, hydroxyalkyl, alkylcarbonylalkyl, cycloalkyl, haloalkoxy, haloalkyl, haloalkylsulfonyl, haloalkylthio, halogen, $R_C R_D N$—; or $R_A S(O)_2$—; $R_{11}$, $R_{12}$, $R_{13}$, and $R_{14}$ are hydrogen; $R_C$ and $R_D$ are independently hydrogen or alkyl; and $R_6$ and $R_8$ are as defined in formula (II).

Another embodiment of the present invention relates to compounds of formula (II) wherein —is a single bond; $X_1$ is $CR_1$; $X_2$ is $CR_2$; $R_1$ is lower haloalkyl or halogen wherein the halogen or haloalkyl is —Cl or trifluoromethyl; $R_2$, $R_3$, and $R_4$ are hydrogen; $R_6$ is hydrogen, lower alkyl, lower haloalkyl, or halogen; $R_7$ is alkoxy, alkyl, alkylthio, haloalkoxy, haloalkylsulfonyl, haloalkyl, haloalkylthio, halogen, or $R_C R_D N$—; $R_8$, $R_{11}$, $R_{12}$, $R_{13}$, and $R_{14}$ are hydrogen; and $R_C$ and $R_D$ are independently hydrogen or alkyl.

Another embodiment of the present invention relates to compounds of formula (II) wherein —is a single bond; $X_1$ is $CR_1$; $X_2$ is $CR_2$; $R_1$ is lower haloalkyl or halogen wherein the halogen or haloalkyl is —Cl or trifluoromethyl; $R_2$, $R_3$, and $R_4$ are hydrogen; $R_7$ is halogen wherein the halogen is —Cl; and $R_6$, $R_8$, $R_{11}$, $R_{12}$, $R_{13}$, and $R_{14}$ are hydrogen.

Another embodiment of the present invention relates to compounds of formula (II) wherein —is a single bond; $X_1$ is $CR_1$; $X_2$ is $CR_2$; $R_1$ is lower haloalkyl or halogen; $R_2$, $R_3$, and $R_4$ are hydrogen; $R_7$ is aryl or aryloxy; $R_{11}$, $R_{12}$, $R_{13}$, and $R_{14}$ are hydrogen; and $R_6$, and $R_8$ are as defined in formula (II).

Another embodiment of the present invention relates to compounds of formula (II) wherein —is a single bond; $X_1$ is $CR_1$; $X_2$ is $CR_2$; $R_1$ is lower haloalkyl or halogen wherein the halogen or haloalkyl is —Cl or trifluoromethyl; $R_2$, $R_3$, and $R_4$ are hydrogen; $R_6$ is hydrogen, lower alkyl, lower haloalkyl, or halogen; $R_7$ is aryl wherein the aryl is phenyl; and $R_8$, $R_{11}$, $R_{12}$, $R_{13}$, and $R_{14}$ are hydrogen.

Another embodiment of the present invention relates to compounds of formula (II) wherein —is a single bond; $X_1$ is $CR_1$; $X_2$ is $CR_2$; $R_1$ is lower haloalkyl or halogen wherein the halogen or haloalkyl is —Cl or trifluoromethyl; $R_2$, $R_3$, and $R_4$ are hydrogen; $R_6$ is hydrogen, lower alkyl, lower haloalkyl, or halogen; $R_7$ is aryloxy wherein the aryl of the aryloxy is phenyl; and $R_8$, $R_{11}$, $R_{12}$, $R_{13}$, and $R_{14}$ are hydrogen.

Another embodiment of the present invention relates to compounds of formula (II) wherein wherein —is a single bond; $X_1$ is $CR_1$; $X_2$ is $CR_2$; $R_1$ is lower haloalkyl or halogen; $R_2$, $R_3$, and $R_4$ are hydrogen; $R_7$ is heterocycle; $R_{11}$, $R_{12}$, $R_{13}$, and $R_{14}$ are hydrogen; and $R_6$, and $R_8$ are as defined in formula (II).

Another embodiment of the present invention relates to compounds of formula (II) wherein wherein —is a single bond; $X_1$ is $CR_1$; $X_2$ is $CR_2$; $R_1$ is lower haloalkyl or halogen wherein the halogen or haloalkyl is —Cl or trifluoromethyl; $R_2$, $R_3$, and $R_4$ are hydrogen; $R_6$ is hydrogen, lower alkyl, lower haloalkyl, or halogen; $R_7$ is heterocycle wherein the heterocycle is azepanyl, morpholinyl, or piperidinyl; and $R_8$, $R_{11}$, $R_{12}$, $R_{13}$, and $R_{14}$ are hydrogen.

Another embodiment of the present invention relates to compounds of formula (II) in which $R_7$ and $R_6$ taken together with the atoms they are attached can form a ring selected from the group consisting of 2,2,3,3-tetrafluoro-2,3-dihydro-benzo[1,4]dioxinyl; 2,3-tetrahydro-benzo[1,4]dioxinyl; 2,2-difluoro-benzo[1,3]dioxolyl; and 2,2-dihydro-benzo[1,3]dioxolyl. Preferred embodiments include compounds in which $R_7$ and $R_6$ taken together with the atoms they are attached can form 2,2,3,3-tetrafluoro-2,3-dihydro-benzo[1,4]dioxinyl and 2,2-difluoro-benzo[1,3]dioxolyl.

Another embodiment of the present invention relates to compounds of formula (II) wherein —is a single bond; $X_1$ is $CR_1$; $X_2$ is $CR_2$; $R_1$ is lower haloalkyl or halogen wherein the halogen or haloalkyl is —Cl or trifluoromethyl; $R_2$, $R_3$, and $R_4$ are hydrogen; $R_6$ is lower alkyl, lower haloalkyl, or halogen; and $R_7$, $R_8$, $R_{11}$, $R_{12}$, $R_{13}$, and $R_{14}$ are hydrogen.

Another embodiment of the present invention relates to compounds of formula (II) wherein wherein —is a single bond; $X_1$ is $CR_1$; $X_2$ is $CR_2$; $R_1$ is lower haloalkyl or halogen wherein the halogen or haloalkyl is —Cl or trifluoromethyl; $R_2$, $R_3$, and $R_4$ are hydrogen; $R_6$ is lower alkyl, lower haloalkyl, or halogen; and $R_7$, $R_8$, $R_{11}$, $R_{12}$, $R_{13}$, and $R_{14}$ are hydrogen.

Another embodiment of the present invention relates to compounds of formula (II) wherein —is a single bond; $X_1$ is N; $X_2$ is $CR_2$; $R_2$, $R_3$, and $R_4$ are hydrogen; $R_7$ is alkoxy, alkyl, alkylthio, haloalkoxy, haloalkyl, haloalkylsulfonyl, haloalkylthio, halogen, or $R_CR_DN$—; $R_{11}$, $R_{12}$, $R_{13}$, and $R_{14}$ are hydrogen; $R_C$ and $R_D$ are independently hydrogen or alkyl; and $R_6$ and $R_8$ are as defined in formula (II).

Another embodiment of the present invention relates to compounds of formula (II) wherein —is a single bond; $X_1$ is N; $X_2$ is $CR_2$; $R_2$, $R_3$, $R_4$, and $R_8$ are hydrogen; $R_6$ is hydrogen, lower alkyl, lower haloalkyl, or halogen; $R_7$ is alkoxy, alkyl, alkylthio, haloalkoxy, haloalkyl, haloalkylsulfonyl, haloalkylthio, halogen, or $R_CR_DN$—; $R_{11}$, $R_{12}$, $R_{13}$, and $R_{14}$ are hydrogen; and $R_C$ and $R_D$ are independently hydrogen or alkyl.

Another embodiment of the present invention relates to compounds of formula (II) wherein —is a single bond; $X_1$ is N; $X_2$ is $CR_2$; $R_2$, $R_3$, and $R_4$ are hydrogen; $R_7$ is heterocycle; $R_{11}$, $R_{12}$, $R_{13}$, and $R_{14}$ are hydrogen; $R_C$ and $R_D$ are independently hydrogen or alkyl; and $R_6$ and $R_8$ are as defined in formula (II).

Another embodiment of the present invention relates to compounds of formula (III)

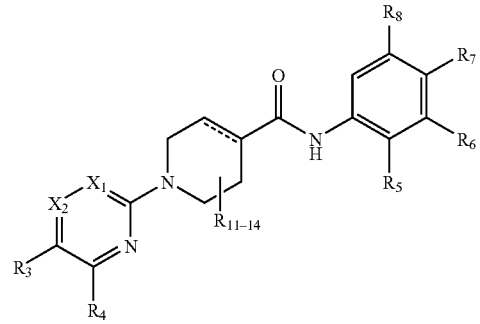

or a pharmaceutically acceptable salt or prodrug thereof, in which —is a single bond; $X_1$ is $CR_1$; $X_2$ is $CR_2$; $R_1$ is hydrogen, lower haloalkyl or halogen; $R_2$, $R_3$, $R_4$, and $R_6$, are hydrogen; $R_5$ is alkyl, hydrogen, halogen, alkoxy, or haloalkoxy; $R_7$ is alkoxy, alkyl, alkylthio, cycloalkyl, haloalkoxy, haloalkyl, haloalkylsulfonyl, haloalkylthio, halogen, $R_CR_DN$—; or $R_AS(O)_2$—; $R_{11}$, $R_{12}$, $R_{13}$, and $R_{14}$ are hydrogen; and $R_A$, $R_C$ and $R_D$ are independently hydrogen or alkyl.

Another embodiment of the present invention relates to compounds of formula (IV)

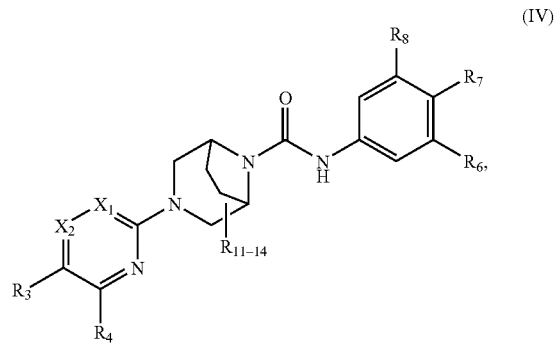

or a pharmaceutically acceptable salt or prodrug thereof wherein $X_1$ is N or $CR_1$; $X_2$ is N or $CR_2$; $R_1$ is hydrogen, lower alkoxy, lower alkenyl, lower alkyl, lower alkylthio, lower alkynyl, lower haloalkoxy, lower haloalkyl, lower haloalkylthio, halogen, hydroxy, mercapto, nitro, or $R_AR_BN$—; $R_2$, $R_3$, and $R_4$ are independently hydrogen or halogen; $R_7$ is hydrogen, alkenyl, alkoxy, alkoxycarbonyl, alkoxysulfonyl, alkyl, alkylcarbonyl, alkylsulfonyl, alkylthio, alkynyl, aryl, arylalkyl, aryloxy, arylthio, cycloalkyl, cycloalkylalkyl, cycloalkyloxy, cycloalkylthio, haloalkoxy, haloalkyl, haloalkylsulfonyl, haloalkylthio, halogen, heteroaryl, heteroarylalkyl, heteroaryloxy, heteroarylthio, heterocycle, heterocyclealkyl, hydroxy, hydroxyalkyl, $R_CR_DN$—, $(R_AR_BN)$carbonyl-, or $(R_AR_BN)$sulfonyl-; $R_6$ and $R_8$ are independently hydrogen, lower alkenyl, lower alkoxy, lower alkyl, lower alkylthio, lower alkynyl, lower haloalkoxy, lower haloalkyl, lower haloalkylthio, halogen, hydroxy, mercapto, or $R_AR_BN$—; $R_A$ and $R_B$ are independently hydrogen or alkyl; and $R_C$ and $R_D$ are independently hydrogen, alkenyl, alkoxycarbonyl, alkyl, alkylcarbonyl, alkynyl, or $(R_AR_BN)$carbonyl-.

Another embodiment of the present invention relates to compounds of formula (IV) wherein $X_1$ is $CR_1$; $X_2$ is $CR_2$; $R_1$ is lower haloalkyl or halogen; $R_2$, $R_3$, and $R_4$ are hydrogen; $R_7$ is alkoxy, alkyl, alkylthio, haloalkoxy, haloalkyl, haloalkylthio, halogen, or $R_CR_DN$—; $R_{11}$, $R_{12}$, $R_{13}$, and $R_{14}$ are hydrogen; $R_C$ and $R_D$ are independently hydrogen or alkyl; and $R_6$ and $R_8$ are as defined in formula (IV).

Another embodiment of the present invention relates to compounds of formula (IV) wherein $X_1$ is $CR_1$; $X_2$ is $CR_2$; $R_1$ is lower haloalkyl or halogen wherein the halogen or haloalkyl is —Cl or trifluoromethyl; $R_2$, $R_3$, and $R_4$ are hydrogen; $R_6$ is hydrogen, lower alkyl, lower haloalkyl, or halogen; $R_7$ is alkoxy, alkyl, alkylthio, haloalkoxy, haloalkyl, haloalkylthio, halogen, or $R_CR_DN$—; $R_8$, $R_{11}$, $R_{12}$, $R_{13}$, and $R_{14}$ are hydrogen; and $R_C$ and $R_D$ are independently hydrogen or alkyl.

Another embodiment of the present invention relates to compounds of formula (V)

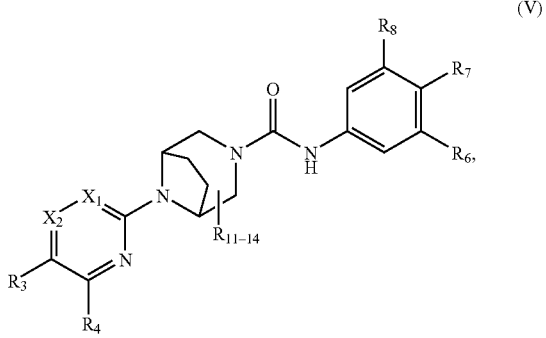

(V)

or a pharmaceutically acceptable salt or prodrug wherein $X_1$ is N or $CR_1$; $X_2$ is N or $CR_2$; $R_1$ is hydrogen, lower alkoxy, lower alkenyl, lower alkyl, lower alkylthio, lower alkynyl, lower haloalkoxy, lower haloalkyl, lower haloalkylthio, halogen, hydroxy, mercapto, nitro, or $R_AR_BN$—; $R_2$, $R_3$, and $R_4$ are independently hydrogen or halogen; $R_7$ is hydrogen, alkenyl, alkoxy, alkoxycarbonyl, alkoxysulfonyl, alkyl, alkylcarbonyl, alkylsulfonyl, alkylthio, alkynyl, aryl, arylalkyl, aryloxy, arylthio, cycloalkyl, cycloalkylalkyl, cycloalkyloxy, cycloalkylthio, haloalkoxy, haloalkyl, haloalkylsulfonyl, haloalkylthio, halogen, heteroaryl, heteroarylalkyl, heteroaryloxy, heteroarylthio, heterocycle, heterocyclealkyl, hydroxy, hydroxyalkyl, $R_CR_DN$—, $(R_AR_BN)$carbonyl-, or $(R_AR_BN)$sulfonyl-; $R_6$ and $R_8$ are independently hydrogen, lower alkenyl, lower alkoxy, lower alkyl, lower alkylthio, lower alkynyl, lower haloalkoxy, lower haloalkyl, lower haloalkylthio, halogen, hydroxy, mercapto, or $R_AR_BN$—; $R_A$ and $R_B$ are independently hydrogen or alkyl; and $R_C$ and $R_D$ are independently hydrogen, alkenyl, alkoxycarbonyl, alkyl, alkylcarbonyl, alkynyl, or $(R_AR_BN)$carbonyl-.

Another embodiment of the present invention relates to compounds of formula (IV) wherein $X_1$ is $CR_1$; $X_2$ is $CR_2$; $R_1$ is lower haloalkyl or halogen wherein the halogen or haloalkyl is —Cl or trifluoromethyl; $R_2$, $R_3$, and $R_4$ are hydrogen; $R_7$ is alkoxy, alkyl, alkylthio, haloalkoxy, haloalkyl, haloalkylthio, halogen, or $R_CR_DN$—; $R_6$, $R_8$, $R_{11}$, $R_{12}$, $R_{13}$, and $R_{14}$ are hydrogen; and $R_C$ and $R_D$ are independently hydrogen or alkyl.

Another embodiment of the present invention relates to compounds of formula (VI)

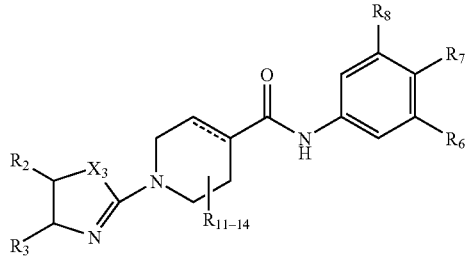

or a pharmaceutically acceptable salt or prodrug wherein $X_3$ is S; $R_2$, and $R_3$ are independently hydrogen or halogen; $R_7$ is hydrogen, alkenyl, alkoxy, alkoxycarbonyl, alkoxysulfonyl, alkyl, alkylcarbonyl, alkoxycarbonylalkyl, alkylsulfonyl, alkylthio, alkynyl, aryl, arylalkyl, aryloxy, arylthio, cyanoalkyl, cycloalkyl, cycloalkylalkyl, cycloalkyloxy, cycloalkylthio, haloalkoxy, haloalkyl, haloalkylsulfonyl, haloalkylthio, halogen, heteroaryl, heteroarylalkyl, heteroaryloxy, heteroarylthio, heterocycle, heterocyclealkyl, hydroxy, hydroxyalkyl, $R_CR_DN$—, $(R_AR_BN)$carbonyl-, $(R_AR_BN)$sulfonyl-; or $R_AS(O)_2$—; $R_6$ and $R_8$ are independently hydrogen, lower alkenyl, lower alkoxy, lower alkyl, lower alkylthio, lower alkynyl, lower haloalkoxy, lower haloalkyl, lower haloalkylthio, halogen, hydroxy, mercapto, or $R_AR_BN$—; and $R_A$ and $R_B$ are independently alkyl, hydrogen, haloalkyl, or heterocycle.

Another embodiment of the present invention relates to compounds of formula (VII)

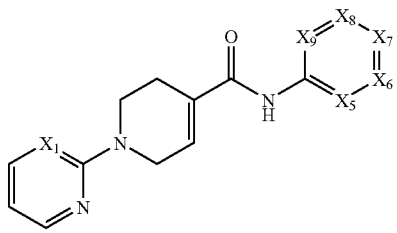

or a pharmaceutically acceptable salt or prodrug wherein $X_1$ is N or $CR_1$; $X_5$ is N or $CR_5$;

$X_6$ is a bond or $CR_6$; $X_7$ is N or $CR_7$; $X_8$ is N or $CR_8$; $X_9$ is N or $CR_9$; $R_1$, $R_5$, and $R_9$ are independently selected from the group consisting of hydrogen, alkyl, alkoxy, halogen, haloalkyl and heterocycle; $R_7$ is hydrogen, alkenyl, alkoxy, alkoxycarbonyl, alkoxysulfonyl, alkyl, alkylcarbonyl, alkoxycarbonylalkyl, alkylsulfonyl, alkylthio, alkynyl, aryl, arylalkyl, aryloxy, arylthio, cyanoalkyl, cycloalkyl, cycloalkylalkyl, cycloalkyloxy, cycloalkylthio, haloalkoxy, haloalkyl, haloalkylsulfonyl, haloalkylthio, halogen, heteroaryl, heteroarylalkyl, heteroaryloxy, heteroarylthio, heterocycle, heterocyclealkyl, hydroxy, hydroxyalkyl, $R_CR_DN$—, $(R_AR_BN)$carbonyl-, $(R_AR_BN)$sulfonyl-; or $R_AS(O)_2$—; $R_6$ and $R_8$ are independently hydrogen, lower alkenyl, lower alkoxy, lower alkyl, lower alkylthio, lower alkynyl, lower haloalkoxy, lower haloalkyl, lower haloalkylthio, halogen, hydroxy, mercapto, or $R_AR_BN$—;

$R_A$ and $R_B$ are independently alkyl, hydrogen, haloalkyl, or heterocycle; and $R_C$ and $R_D$ are independently hydrogen, alkenyl, alkoxycarbonyl, alkyl, alkylcarbonyl, alkynyl, or $(R_A R_B N)$carbonyl-.

Another embodiment of the present invention relates to compounds of formula (VII) wherein $X_1$ is $CR_1$; $X_5$ is $CR_5$; $X_6$ is $CR_6$; $X_7$ is $CR_7$; $X_8$ is $CR_8$; $X_9$ is N or $CR_9$; $R_7$ and $R_8$ are independently selected from the group consisting of hydrogen, alkyl, and halogen.

Another embodiment of the present invention relates to compounds of formula (VII) wherein $X_1$ is $CR_1$; $X_5$ is $CR_5$; $X_6$ is $CR_6$; $X_7$ is $CR_7$; $X_8$ is N; $X_9$ is $CR_9$; $R_5$, $R_6$, $R_9$ and $R_1$ are independently selected from the group consisting of hydrogen, alkyl, haloalkyl, and halogen; $R_7$ is hydrogen, alkenyl, alkoxy, alkoxycarbonyl, alkoxysulfonyl, alkyl, alkylcarbonyl, alkoxycarbonylalkyl, alkylsulfonyl, alkylthio, alkynyl, aryl, arylalkyl, aryloxy, arylthio, cyanoalkyl, cycloalkyl, cycloalkylalkyl, cycloalkyloxy, cycloalkylthio, haloalkoxy, haloalkyl, haloalkylsulfonyl, haloalkylthio, halogen, heteroaryl, heteroarylalkyl, heteroaryloxy, heteroarylthio, heterocycle, heterocyclealkyl, hydroxy, hydroxyalkyl, $R_C R_D N$—, $(R_A R_B N)$carbonyl-, $(R_A R_B N)$sulfonyl-; or $R_A S(O)_2$—; $R_A$ and $R_B$ are independently alkyl, hydrogen, halogen, haloalkyl, or heterocycle; and $R_C$ and $R_D$ are independently hydrogen, alkenyl, alkoxycarbonyl, alkyl, alkylcarbonyl, alkynyl, or $(R_A R_B N)$carbonyl.

Another embodiment of the present invention relates to compounds of formula (VII) wherein $X_1$ is $CR_1$; $X_5$ is $CR_5$; $X_6$ is a bond; $X_7$ is N; $X_8$ is N; $X_9$ is $CR_9$; $R_1$, $R_9$ and $R_5$, are independently selected from the group consisting of hydrogen, alkyl, haloalkyl, and halogen.

Another embodiment of the present invention relates to compounds of formula (VII) wherein $X_1$ is N; $X_5$ is $CR_5$; $X_6$ is $CR_6$; $X_7$ is $CR_7$; $X_8$ is N; $X_9$ is $CR_9$; $R_6$, $R_7$, $R_9$ and $R_5$, are independently selected from the group consisting of hydrogen, alkyl, haloalkyl, and halogen.

Another embodiment of the present invention relates to pharmaceutical compositions comprising a therapeutically effective amount of a compound of formula (I-VII) or a pharmaceutically acceptable salt thereof.

Another embodiment of the present invention relates to a method for treating pain in a mammal, comprising administering a therapeutically effective amount of a compound of formula (I-VII) or a pharmaceutically acceptable salt thereof.

(2) Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means a monocyclic-ring system, a bicyclic-fused ring system, or a tricyclic-fused ring system wherein one or more of the fused rings are aromatic. Representative examples of aryl include, but are not limited to, anthracenyl, azulenyl, fluorenyl, 2,3-dihydroindenyl, indenyl, naphthyl, phenyl, and tetrahydronaphthyl.

The aryl groups of this invention can be optionally substituted with 1, 2, 3, or 4 substituents independently selected from alkenyl, alkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, haloalkylsulfonyl, haloalkylthio, halogen, hydroxy, hydroxyalkyl, mercapto, nitro, $R_A R_B N$—, $(R_A R_B N)$carbonyl-, and $(R_A R_B N)$sulfonyl-.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "arylthio" as used herein, means an aryl group, as defined herein, appended to the parent molecular moiety through a sulfur atom. Representative examples of arylthio include, but are not limited to, phenylthio and 2-naphthylthio.

The term "carbonyl" as used herein, means a —C(O)— group.

The term "carboxy" as used herein, means a —CO$_2$H group.

The term "cyano" as used herein, means a —CN group.

The term "cycloalkyl" as used herein, means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The cycoalkyl groups of the present invention are optionally substituted with 1, 2, 3, or 4 substituents selected from alkenyl, alkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, haloalkylsulfonyl, haloalkylthio, halogen, hydroxy, hydroxyalkyl, mercapto, $R_AR_BN$—, $(R_AR_B N)$carbonyl-, and $(R_AR_BN)$sulfonyl-.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkyloxy" as used herein, means cycloalkyl group, as defined herein, appended to the parent molecular moiety through an oxygen atom, as defined herein. Representative examples of cycloalkyloxy include, but are not limited to, cyclopropyloxy, cyclobutyloxy, cyclopentyloxy, cyclohexyloxy, cycloheptyloxy, and cyclooctyloxy.

The term "cycloalkylthio" as used herein, means cycloalkyl group, as defined herein, appended to the parent molecular moiety through a sulfur atom, as defined herein. Representative examples of cycloalkylthio include, but are not limited to, cyclopropylthio, cyclobutylthio, cyclopentylthio, cyclohexylthio, cycloheptylthio, and cyclooctylthio.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkylsulfonyl" as used herein, means a haloalkyl group, as defined herein, appended to the parent molecular moiety through a sulfonyl group. Representative examples of haloalkylsulfonyl include, but are not limited to, trifluoromethylsulfonyl and (pentafluoroethyl)sulfonyl.

The term "haloalkylthio" as used herein, means a haloalkyl group, as defined herein, appended to the parent molecular moiety through a sulfur atom. Representative examples of haloalkylthio include, but are not limited to, trifluoromethylthio and (pentafluoroethyl)thio.

The term "heteroaryl," as used herein, refers to an aromatic five- or six-membered ring wherein 1, 2, 3, or 4 heteroatoms are independently selected from N, O, or S. The five membered rings have two double bonds and the six membered rings have three double bonds. The heteroaryl groups are connected to the parent molecular moiety through a carbon or nitrogen atom. Representative examples of heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetraazolyl, thiadiazolyl, thiazolyl, thienyl, triazolyl, and triazinyl.

The heteroaryl groups of the present invention are optionally substituted 1, 2, 3, or 4 substituents independently selected from alkenyl, alkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, haloalkylthio, halogen, hydroxy, hydroxyalkyl, mercapto, nitro, $R_AR_BN$—, $(R_AR_BN)$carbonyl-, and $(R_AR_BN)$sulfonyl.

The term "heteroarylalkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-pyrimidin-2-ylpropyl.

The term "heteroaryloxy" as used herein, means a heteroaryl group, as defined herein, appended to the parent molecular moiety through an oxygen atom. Representative examples of heteroaryloxy include, but are not limited to, pyridin-3-yloxy, pyridin-4-yloxy, and quinolin-3-yloxy.

The term "heteroarylthio" as used herein, means a heteroaryl group, as defined herein, appended to the parent molecular moiety through a sulfur atom. Representative examples of heteroarylthio include, but are not limited to, pyridin-3-ylthio, pyridin-4-ylthio, and quinolin-3-ylthio.

The term "heterocycle," as used herein, refers to a three, four, five, six, seven or eight membered ring containing one or two heteroatoms independently selected from the group consisting of nitrogen, oxygen, and sulfur. The three membered ring has zero double bonds. The four and five membered ring has zero or one double bond. The six membered ring has zero, one, or two double bonds. The seven and eight membered rings have zero, one, two, or three double bonds. The heterocycle groups of the present invention can be attached to the parent molecular moiety through a carbon atom or a nitrogen atom. The heterocycle groups of the present invention can be a monocyclic-ring system, a bicyclic-fused ring system, or a tricyclic-fused ring system. Representative examples of heterocycle include, but are not limited to, azabycyclooctyl, azetidinyl, azepanyl, aziridinyl, azocanyl, morpholinyl, piperazinyl, piperidinyl, pyrrolidinyl, and thiomorpholinyl.

The heterocycles of the present invention are optionally substituted with 1, 2, 3, or 4 substituents independently selected from alkenyl, alkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, haloalkylthio, halogen, hydroxy, hydroxyalkyl, mercapto, $R_AR_BN$, $(R_AR_BN)$carbonyl, and $(R_AR_BN)$sulfonyl.

The term "heterocyclealkyl" as used herein, means a heterocycle, as defined herein, appended to the parent molecular moiety through an alkyl group, as defined herein. Representative examples of heterocyclealkyl include, but are not limited to, piperidin-1-ylmethyl and 2-piperidin-1-ylethyl.

The term "hydroxy" as used herein, means an —OH group.

The term "hydroxyalkyl" as used herein, means at least one hydroxy group, as defined herein, is appended to the parent molecular moiety through an alkyl group, as defined herein.

Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "lower alkenyl" as used herein, is a subset of alkenyl, as defined herein, and means an alkenyl group containing from 2 to 4 carbon atoms. Examples of lower alkenyl are ethenyl, propenyl, and butenyl.

The term "lower alkoxy" as used herein, is a subset of alkoxy, as defined herein, and means a lower alkyl group, as defined herein, appended to the parent molecular moiety through an oxygen atom, as defined herein. Representative examples of lower alkoxy include, but are not limited to, methoxy, ethoxy, propoxy, 2-propoxy, butoxy, and tert-butoxy.

The term "lower alkyl" as used herein, is a subset of alkyl, as defined herein, and means a straight or branched chain hydrocarbon group containing from 1 to 4 carbon atoms. Representative examples of lower alkyl are methyl, ethyl, n-propyl, iso-propyl, n-butyl, iso-butyl, sec-butyl, and tert-butyl.

The term "lower alkylthio" as used herein, is a subset of alkylthio, and means a lower alkyl group, as defined herein, appended to the parent molecular moiety through a sulfur atom. Representative examples of lower alkylthio include, but are not limited, methylthio, ethylthio, and tert-butylthio.

The term "lower alkynyl" as used herein, is a subset of alkynyl, as defined herein, and means an alkynyl group containing from 2 to 4 carbon atoms. Examples of lower alkynyl are ethynyl, propynyl, and butynyl.

The term "lower haloalkoxy" as used herein, is a subset of haloalkoxy, as defined herein, and means a straight or branched chain haloalkoxy group containing from 1 to 4 carbon atoms. Representative examples of lower haloalkoxy include, but are not limited to, trifluoromethoxy, trichloromethoxy, dichloromethoxy, fluoromethoxy, and pentafluoroethoxy.

The term "lower haloalkyl" as used herein, is a subset of haloalkyl, as defined herein, and means a straight or branched chain haloalkyl group containing from 1 to 4 carbon atoms. Representative examples of lower haloalkyl include, but are not limited to, trifluoromethyl, trichloromethyl, dichloromethyl, fluoromethyl, and pentafluoroethyl.

The term "lower haloalkylthio" as used herein, is a subset of haloalkylthio, as defined herein, and means a straight or branched chain haloalkylthio group containing from 1 to 4 carbon atoms. Representative examples of lower haloalkylthio include, but are not limited to, trifluoromethylthio, trichloromethylthio, fluoromethylthio, and (pentafluoroethyl)thio.

The term "mercapto" as used herein, means a —SH group.

The term "nitro" as used herein, means a —NO$_2$ group.

The term "$R_AR_BN$—" as used herein, means two groups, $R_A$ and $R_B$, which are appended to the parent molecular moiety through a nitrogen atom. $R_A$ and $R_B$ are each independently hydrogen or alkyl. Representative examples of $R_AR_BN$ include, but are not limited to, amino, methylamino, dimethylamino, and diethylamino.

The term "($R_AR_BN$)carbonyl" as used herein, means a $R_AR_BN$— group, as defined herein, appended to the parent molecular moiety through a carbonyl group, as defined herein. Representative examples of ($R_AR_BN$)carbonyl include, but are not limited to, aminocarbonyl, (methylamino)carbonyl, (dimethylamino)carbonyl, and (ethylmethylamino)carbonyl.

The term "($R_AR_BN$)sulfonyl" as used herein, means a $R_AR_BN$— group, as defined herein, appended to the parent molecular moiety through a sulfonyl group, as defined herein. Representative examples of ($R_AR_BN$)sulfonyl include, but are not limited to, aminosulfonyl, (methylamino)sulfonyl, (dimethylamino)sulfonyl, and (ethylmethylamino)sulfonyl.

The term "$R_CR_DN$—" as used herein, means two groups, $R_C$ and $R_D$, which are appended to the parent molecular moiety through a nitrogen atom. $R_C$ and $R_D$ are each independently hydrogen, alkenyl, alkoxycarbonyl, alkyl, alkylcarbonyl, alkynyl, aryl, arylalkyl, cycloalkyl, cycloalkylalkyl, heteroaryl, heteroarylalkyl, or ($R_AR_BN$)carbonyl. Representative examples of $R_CR_DN$ include, but are not limited to, amino, methylamino, dimethylamino, and ethylmethylamino.

The term "sulfonyl" as used herein, means a —S(O)$_2$— group.

Compounds of the present invention can exist as stereoisomers, wherein asymmetric or chiral centers are present. Stereoisomers are designated (R) or (S), depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution, a technique well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) direct separation of the mixture of optical enantiomers on chiral chromatographic columns, or (3) formation of a diastereomeric salt followed by selective recrystallization of one of the diastereomeric salts.

Compounds of the present invention were named by ACD/ChemSketch version 5.0 (developed by Advanced Chemistry Development, Inc., Toronto, ON, Canada) or were given names consistent with ACD nomenclature.

(3) Abbreviations

Abbreviations which have been used in the descriptions of the Schemes and the Examples that follow are: Ac for acetyl; Bu for butyl; DCC for 1,3-dicyclohexylcarbodiimide; DIEA for diisopropylethylamine; DMAP for 4-dimethylaminopyridine; DME for 1,2-dimethoxyethane; DMF for N,N-dimethylformamide; DMSO for dimethylsulfoxide; EDCI or EDC for 1-ethyl-3-[3-(dimethylamino)propyl]-carbodiimide hydrochloride; Ph for phenyl; TFA for trifluoroacetic acid; THF for tetrahydrofuran; and Tf for —S(O)$_2$CF$_3$.

(4) Schemes and Examples

The compounds and processes of the present invention will be better understood in connection with the following synthetic Schemes and Examples, which illustrate a means by which the compounds of the present invention can be prepared. Further, all citations herein are incorporated by reference.

4(a) Preparation of Compounds of the Present Invention

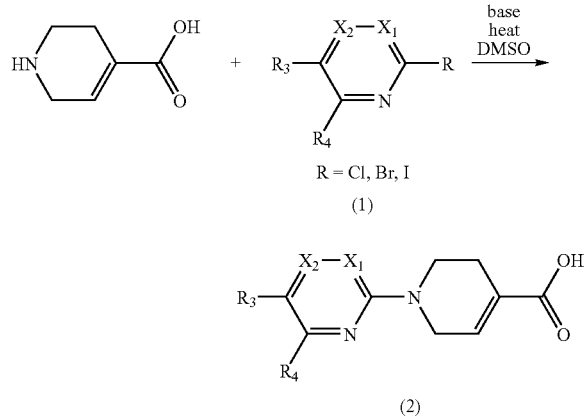

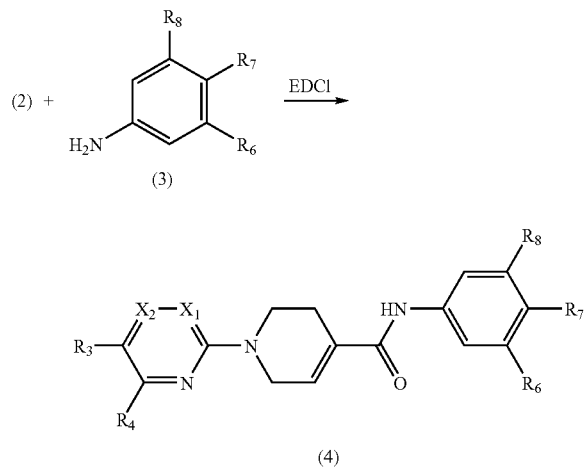

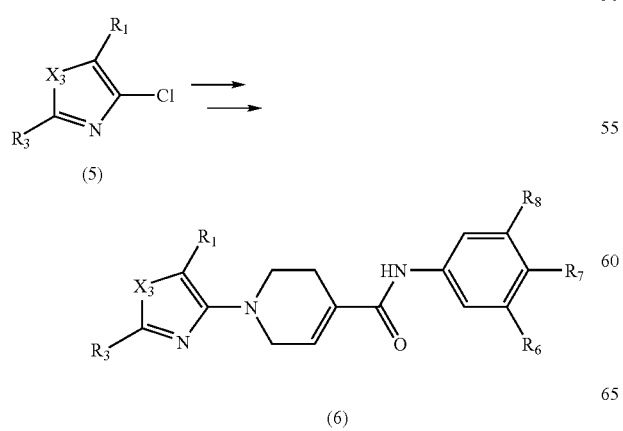

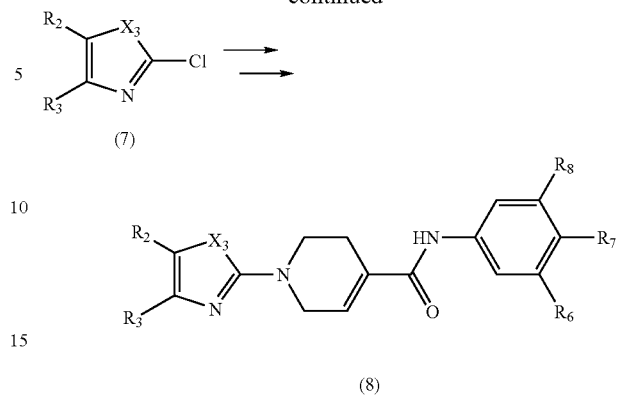

Amides of general formula (4), wherein $X_1$, $X_2$, $X_3$, $R_3$, $R_4$, $R_6$, $R_7$, and $R_8$ are as defined in formula (I-IV), can be prepared as described in Scheme 1. 1,2,3,6-Tetrahydropyridine-4-carboxylic acid, prepared as described in Examples 1A-1C herein, can be treated with 2-halo compounds of general formula (1) and a base including, but not limited to potassium carbonate, in a solvent including, but not limited to, DMSO or DMF and heated until reaction is complete to provide acids of general formula (2). Acids of general formula (2) can be coupled to anilines of general formula (3) using EDCI or DCC to provide amides of general formula (4).

Amides of general formula (6) and general formula (8), wherein $X_3$, $R_1$, $R_2$, $R_3$, $R_6$, $R_7$, and $R_8$ are as defined in formula (I-IV), can be prepared as described in Scheme 1. Oxazoles or thiazoles of general formula (5) or general formula (7) can be processed in a similar manner as compounds of general formula (1) in Scheme 1 to provide amides of general formula (6) or amides of general formula (8) both of which are representative of the compounds of the present invention.

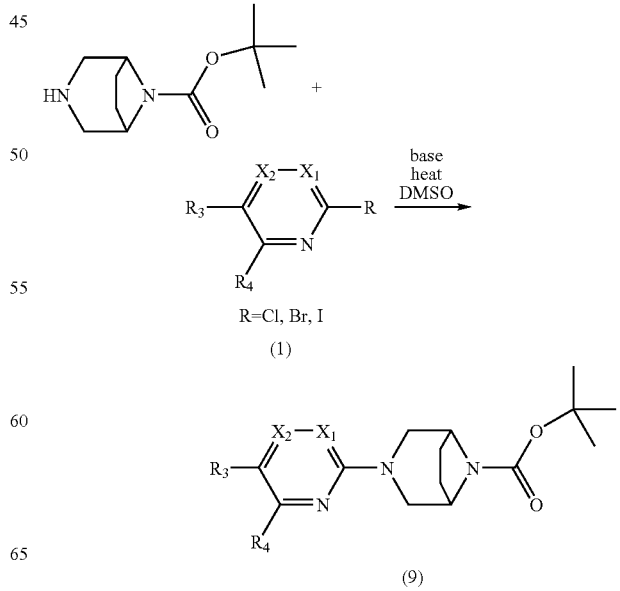

-continued

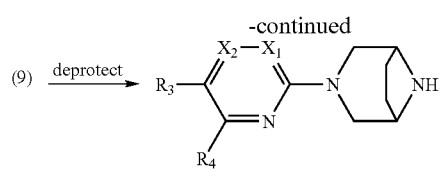
(9) →deprotect (10)

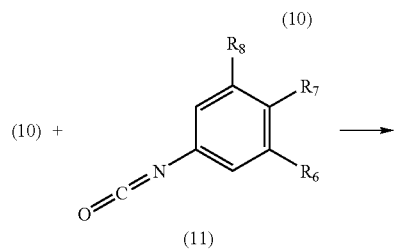
(10) + (11) →

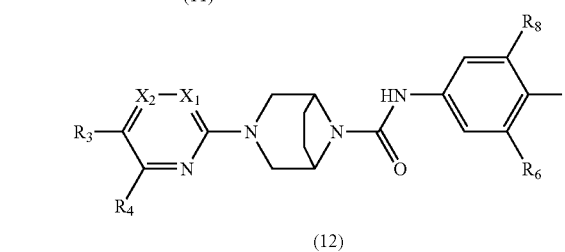
(12)

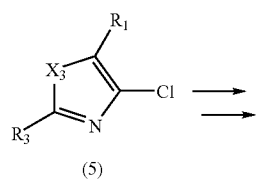
(5) →→

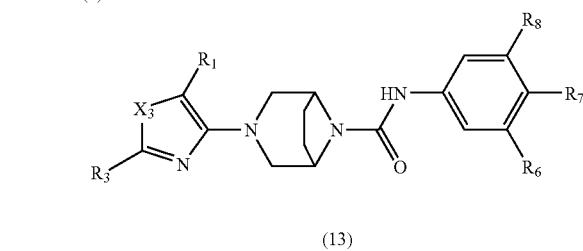
(13)

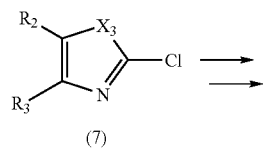
(7) →

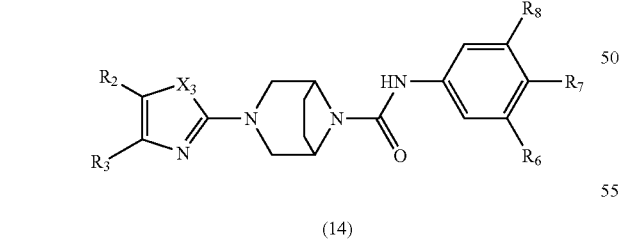
(14)

Amides of general formula (12), wherein $X_1$, $X_2$, $X_3$, $R_3$, $R_4$, $R_6$, $R_7$, and $R_8$ are as defined in formula (I-IV), can be prepared as described in Scheme 2. tert-Butyl 3,8-diazabicyclo[3.2.1]octane-8-carboxylate, prepared as described in Examples 23A-23I herein, can be treated with 2-halo compounds of general formula (1) as described in Scheme 1 to provide compounds of general formula (9). Compounds of general formula (9) can be deprotected with trifluoroacetic acid in methylene chloride (1:1) or with 4.5N hydrochloric acid in 1,4-dioxane to provide compounds of general formula (10). Compounds of general formula (10) can be treated with isocyanates of general formula (11) to provide amides of general formula (12), which are representative of compounds of the present invention.

Amides of general formula (13) and amides of general formula (14), wherein $X_3$, $R_1$, $R_2$, $R_3$, $R_6$, $R_7$, and $R_8$ are as defined in formula (I-IV), can be prepared as described in Scheme 2. Oxazoles or thiazoles of general formula (5) or general formula (7) can be processed in a similar manner as compounds of general formula (1) in Scheme 2 to provide amides of general formula (13) or amides of general formula (14) which are both representative of compounds of the present invention.

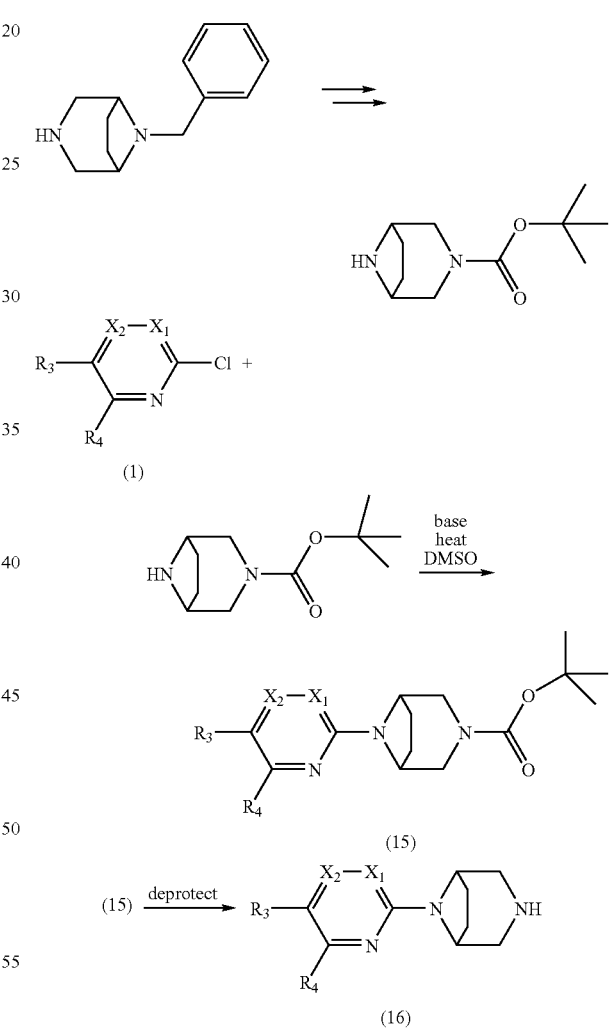

Scheme 3

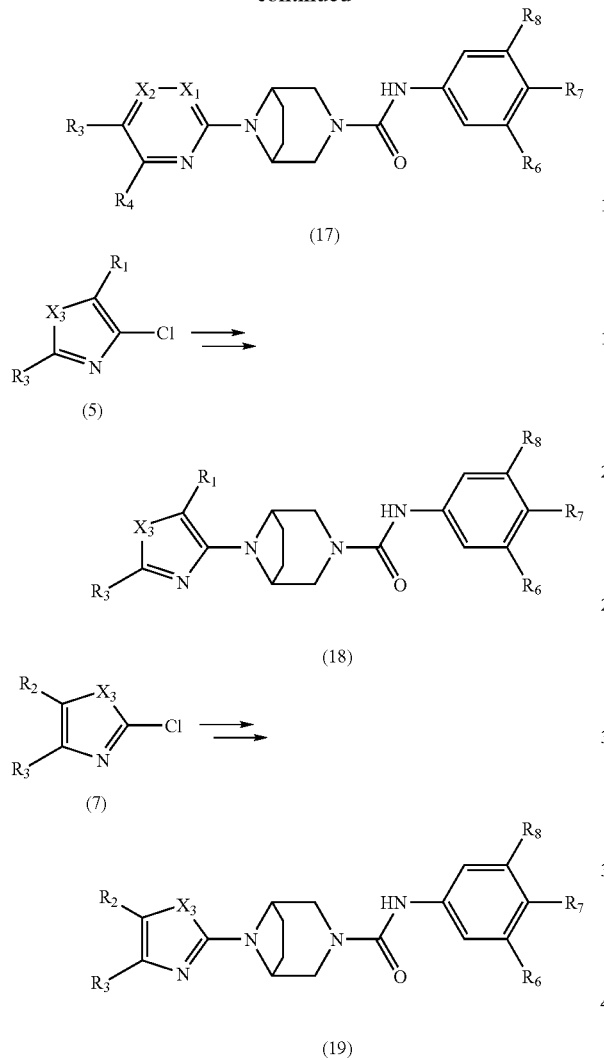

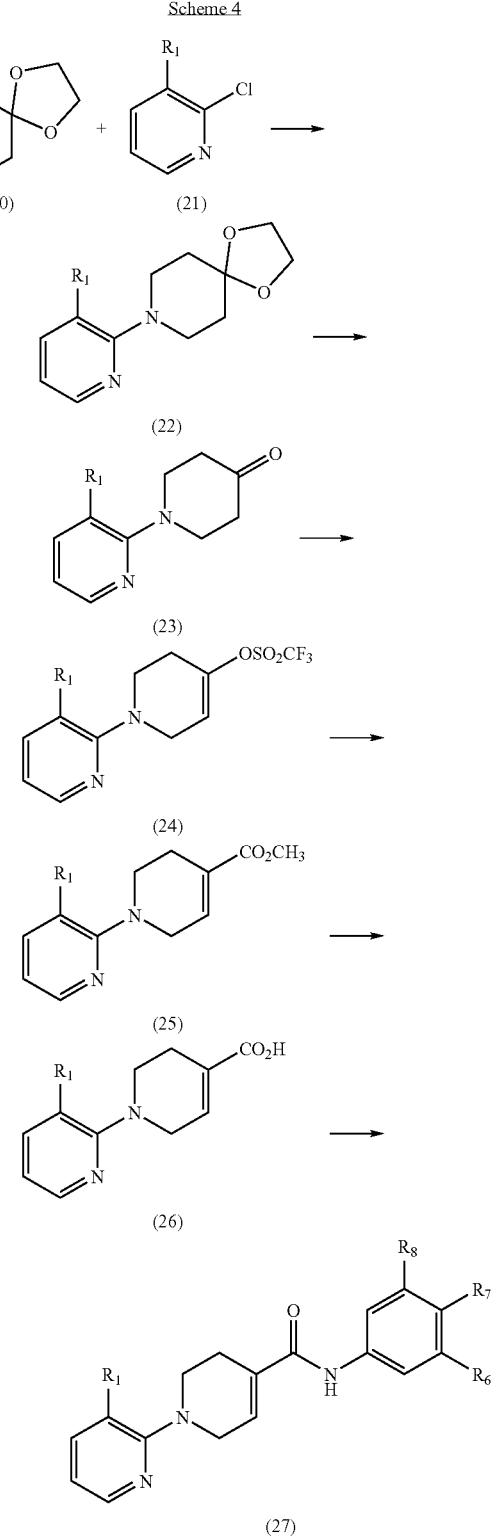

Amides of general formula (17), wherein $X_1$, $X_2$, $X_3$, $R_3$, $R_4$, $R_6$, $R_7$, and $R_8$ are as defined in formula (I-IV), can be prepared as described in Scheme 3. 8-Benzyl-3,8-diazabicyclo[3.2.1]octane, prepared as described in Examples 23A-23F herein, can be processed as described in Examples 34A-34C to provide tert-butyl 3,8-diazabicyclo[3.2.1]octane-3-carboxylate. tert-Butyl 3,8-diazabicyclo[3.2.1]octane-3-carboxylate can be treated with 2-halo compounds of general formula (1) as described in Scheme 1 to provide compounds of general formula (15). Compounds of general formula (15) can be deprotected with trifluoroacetic acid in methylene chloride (1:1) or with 4.5N hydrochloric acid in 1,4-dioxane to provide compounds of general formula (16). Compounds of general formula (16) can be treated with isocyanates of general formula (11) to provide amides of general formula (17) which are representative of compounds of the present invention.

Amides of general formula (18) and amides of general formula (19), wherein $X_3$, $R_1$, $R_2$, $R_3$, $R_6$, $R_7$, and $R_8$ are as defined in formula (I-IV), can be prepared as described in Scheme 3. Oxazoles or thiazoles of general formula (5) or general formula (7) can be processed in a similar manner as compounds of general formula (1) in Scheme 3 to provide amides of general formula (18) or amides of general formula (19) which are representative of compounds of the present invention.

Amines of formula (20) when treated with chloropyridines of formula (21), wherein $R_1$ is lower haloalkyl or halogen, in the presence of potassium carbonate in DMSO will provide compounds of formula (22). Compounds of formula (22) when treated with hydrochloric acid will provide compounds of formula (23). Compounds of formula (23) when treated with lithium diisopropylamine and N-phenyltrifluoromethanesulfonimide will provide compounds of formula (24). Compounds of formula (24) when treated with PdCl$_2$(PPh$_3$)$_2$, carbon dioxide, triethylamine in methanol will provide compounds of formula (25). Compounds of formula (25) when treated with sodium hydroxide or lithium hydroxide in alcoholic solvents will provide compounds of formula (26). Compounds of formula (26) when treated with anilines of formula (3) and EDCI will provide compounds of formula (27). Alternatively, compounds of formula (26) when treated with oxalyl chloride followed by treatment with an aniline of formula (3) wherein R$_8$, R$_7$, and R$_6$ are defined in formula 1-IV and a base such as triethylamine will provide compounds of formula (27). The preparation of compounds of formula (27) wherein R$_1$ is lower haloalkyl or halogen, particularly trifluoromethane or chloride are representative of compounds of the present invention.

Scheme 5

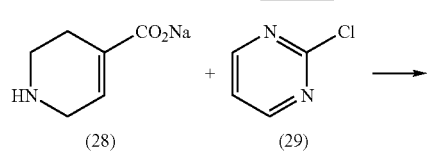

(28)    (29)

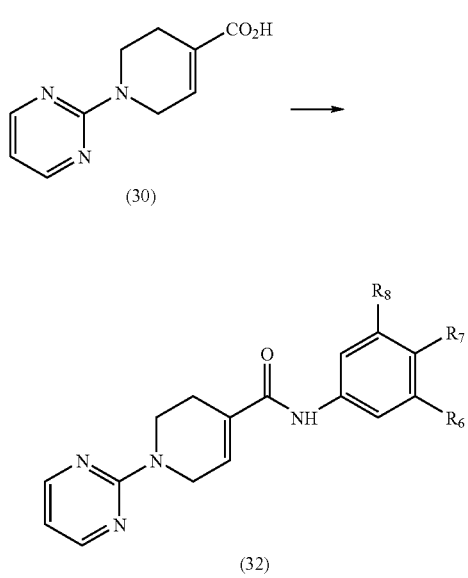

Compounds of formula (28) and compounds of formula (29) when treated with potassium carbonate in DMSO will provide compounds of formula (30). Compounds of formula (30) when treated with compounds of formula (3) wherein R$_8$, R$_7$, and R$_6$ are as defined in formula (I-IV) and EDCI will provide compounds of formula (32) which are representative of the compounds of the present invention.

4(b) EXAMPLES

Example 1

N-(4-tert-butylphenyl)-3'-chloro-3,6-dihydro-2H-1, 2'-bipyridine-4-carboxamide

Example 1A 1-(1-chloroethyl) 4-ethyl 3,6-dihydro-1,4(2H)-pyridinedicarboxylate

Ethyl 1-methyl-1,2,3,6-tetrahydro-4-pyridinecarboxylate (47 g, 278 mmol) in dichloroethane (800 mL) was treated with α-chloroethyl chloroformate (50 g, 350 mmol) dropwise at 0° C. The mixture was warmed to room temperature, refluxed for 2 hours, and then allowed to cool to room temperature. The mixture was concentrated under reduced pressure and the residue was purified via column chromatography (SiO$_2$, ethyl acetate) to provide the title compound. $^1$H NMR (300 MHz, CDCl$_3$) δ 6.88 (m, 1H), 6.61 (q, 1H), 4.22 (q, 2H), 4.16 (m, 2H), 7.35 (d, 2H), 3.58 (m, 2H), 2.44 (m, 2H), 1.82 (d, 3H), 1.30 (t, 3H).

Example 1B ethyl 1,2,3,6-tetrahydro-4-pyridinecarboxylate 1-(1-Chloroethyl) 4-ethyl 3,6-dihydro-1,4(2H)-pyridinedicarboxylate (61.8 g, 236 mmol) in methanol (500 mL) was heated at reflux for 30 minutes. The mixture was allowed to cool to room temperature and concentrated to provide the title compound. $^1$H NMR (300 MHz, CDCl$_3$) δ 6.86 (m, 1H), 4.22 (q, 2H), 3.85 (m, 2H), 3.34 (m, 2H), 2.75 (m, 2H), 1.30 (t, 3H).

Example 1C 1,2,3,6-tetrahydropyridine-4-carboxylic acid

Ethyl 1,2,3,6-tetrahydro-4-pyridinecarboxylate (44.7 g, 234 mmol) in dichloromethane (200 mL) was treated with aqueous K$_2$CO$_3$ (saturated) and the phases were separated. The aqueous layer was dried under reduced pressure and the residue was triturated with dichloromethane (100×3 mL) and dissolved in methanol (100 mL). The solution was treated with a saturated solution of NaOH (10 g, 250 mmol) in methanol (250 mL) and sodium methoxide in methanol (0.5M, 200 mL, 100 mmol). After stirring at room temperature for two days, the mixture was concentrated under reduced pressure. The residue was triturated with methanol (200×5 mL) and dried under reduced pressure to provide the title compound. $^1$H NMR (300 MHz, CD$_3$OD) δ 6.60 (m, 1H), 3.38 (m, 2H), 2.88 (m, 2H), 2.30 (m, 2H).

Example 1D

3'-chloro-3,6-dihydro-2H-1,2'-bipyridine-4-carboxylic acid 1,2,3,6-Tetrahydro-4-pyridinecarboxylic acid (7.0 g, 47 mmol) and 2-bromo-3-chloropyridine (11.0 g, 57 mmol) were combined in DMSO (100 mL) and treated with anhydrous K$_2$CO$_3$ (8.0 g, 58 mmol). The mixture was heated at 90° C. overnight, allowed to cool to room temperature, and then concentrated under reduced pressure. The residue in dichloromethane (200 mL) was cooled to −78° C. and treated with an excess of TFA (10 mL, 130 mmol) dropwise. The mixture was allowed to warm to room temperature and the layers were separated. The organic layer was washed with brine, dried over $Na_2SO_4$, filtered, and the filtrate concentrated under reduced pressure to provide the title compound which was used in the next step without further purification.

Example 1E

N-(4-tert-butylphenyl)-3'-chloro-3,6-dihydro-2H-1,2'-bipyridine-4-carboxamide 3'-Chloro-3,6-dihydro-2H-1,2'-bipyridine-4-carboxylic acid (120 mg, 0.35 mmol), 4-tert-butylaniline (90.0 mg, 0.6 mmol), and EDCI (145 mg, 0.75 mmol) were combined in dichloromethane (3 mL) under $N_2$ and stirred at room temperature overnight. The mixture was treated with water and the layers were separated. The organic layer was concentrated and the residue was purified via column chromatography ($SiO_2$, ethyl acetate:hexanes, 1:4) to provide the title compound. $^1$H NMR (500 MHz, $CDCl_3$) δ 8.18 (dd, 1H), 7.61 (dd, 1H), 7.46 (d, 2H), 7.38 (s(br), 1H), 7.35 (d, 2H), 6.85 (dd, 1H), 6.75 (m, 1H), 4.10 (dd, 2H), 3.58 (dd, 2H), 2.68 (m, 2H), 1.30 (s, 9H); MS (ESI) 370 (M+H)$^+$.

Example 2

3'-chloro-N-(4-methylphenyl)-3,6-dihydro-2H-1,2'-bipyridine-4-carboxamide

The title compound was prepared using the procedure described in Example 1E using 4-methylaniline instead of 4-tert-butylaniline. $^1$H NMR (500 MHz, $CDCl_3$) δ 8.18 (dd, 1H), 7.62 (dd, 1H), 7.43 (d, 2H), 7.10 (1H, NH), 7.15 (d, 2H), 6.84 (dd, 1H), 6.76 (m, 1H), 4.08 (dd, 2H), 3.58 (dd, 2H), 2.66 (m, 2H), 2.32 (s, 3H); MS (ESI) 328 (M+H)$^+$.

Example 3

3'-chloro-N-(4-methylphenyl-3,6-dihydro-2H-1,2'-bipyridine-4-carboxamide

The title compound was prepared using the procedure described in Example 1E using 4-methoxyaniline instead of 4-tert-butylaniline. $^1$H NMR (500 MHz, $CDCl_3$) δ 8.21 (dd, 1H), 7.64 (dd, 1H), 7.55 (s(br), 1H), 7.45 (m, 2H), 6.90 (m, 3H), 6.76 (m, 1H), 4.15 (dd, 2H), 3.80 (s, 3H), 3.65 (dd, 2H), 2.68 (m, 2H); MS (ESI) 343 (M+H)$^+$.

Example 4

3'-chloro-N-(4-fluorophenyl)-3,6-dihydro-2H-1,2'-bipyridine-4-carboxamide

The title compound was prepared using the procedure described in Example 1E using 4-fluoroaniline instead of 4-tert-butylaniline. $^1$H NMR (500 MHz, $CDCl_3$) δ 8.20 (dd, 1H), 7.66 (dd, 1H), 7.58 (s(br), 1H), 7.54 (m, 2H), 7.02 (m, 2H), 6.90 (dd, 1H), 6.76 (m, 1H), 4.15 (dd, 2H), 3.62 (dd, 2H), 2.68 (m, 2H); MS (ESI) 331 (M+H)$^+$.

Example 5

3'-chloro-N-(4-chlorophenyl)-3,6-dihydro-2H-1,2'-bipyridine-4-carboxamide

4-Chloroaniline (13.2 g, 103 mmol), 3'-chloro-3,6-dihydro-2H-1,2'-bipyridine-4-carboxylic acid (16.49 g, 69.1 mmol), 1-[3-(dimethylamino)propyl]-3-ethylcarbodiimide hydrochloride (26.5 g, 138 mmol) were combined in dichloromethane (150 mL) and stirred overnight at ambient temperature. The mixture was diluted with dichloromethane (200 mL), washed with water (400 mL), 400 mL brine, dried with sodium sulfate, filtered, and the filtrate was concentrated under reduced pressure. The residue was purified by chromatography on silica gel using hexane:ethyl acetate (7:3) to provide the title compound. $^1$H NMR (500 MHz, $CDCl_3$) δ 8.20 (dd, 1H), 7.70 (dd, 1H), 7.62 (s(br) 1H), 7.54 (d, 2H), 7.30 (d, 2H), 6.92 (dd, 1H), 6.76 (m, 1H), 4.16 (dd, 2H), 3.64 (dd, 2H), 2.66 (m, 2H); MS (ESI) 349 (M+H)$^+$.

Example 6

N-(4-bromophenyl)-3'-chloro-3,6-dihydro-2H-1,2'-bipyridine-4-carboxamide

The title compound was prepared using the procedure described in Example 1E using 4-bromoaniline instead of 4-tert-butylaniline. $^1$H NMR (500 MHz, $CDCl_3$) δ 8.20 (dd, 1H), 7.65 (dd, 1H), 7.55 (s(br) 1H), 7.48 (d, 2H), 7.44 (d, 2H), 6.88 (dd, 1H), 6.78 (m, 1H), 4.15 (dd, 2H), 3.61 (dd, 2H), 2.66 (m, 2H); MS (ESI) 393 (M+H)$^+$.

Example 7

3'-chloro-N-[4-(trifluoromethoxy)phenyl]-3,6-dihydro-2H-1,2'-bipyridine-4-carboxamide The title compound was prepared using the procedure described in Example 1E using 4-(trifluoromethoxy)aniline instead of 4-tert-butylaniline. $^1$H NMR (500 MHz, $CDCl_3$) δ 8.20 (dd, 1H), 7.65 (dd, 1H), 7.55 (s(br) 1H), 7.48 (d, 2H), 7.44 (d, 2H), 6.88 (dd, 1H), 6.78 (m, 1H), 4.15 (dd, 2H), 3.61 (dd, 2H), 2.66 (m, 2H); MS (ESI) 393 (M+H)$^+$.

Example 8

3'-chloro-N-(4-phenoxyphenyl)-3,6-dihydro-2H-1,2'-bipyridine-4-carboxamide

The title compound was prepared using the procedure described in Example 1E using 4-phenoxyaniline instead of 4-tert-butylaniline. $^1$H NMR (500 MHz, $CDCl_3$) δ 8.19 (dd, 1H), 7.62 (dd, 1H), 7.54 (d, 2H), 7.54 (s(br) 1H), 7.32 (dd. 2H), 7.08 (t, 1H), 7.00 (m, 4H), 6.85 (dd, 1H), 6.78 (m, 1H), 4.12 (dd, 2H), 3.59 (dd, 2H), 2.68 (m, 2H); MS (ESI) 406 (M+H)$^+$.

Example 9

3'-chloro-N-(4-ethylphenyl)-3,6-dihydro-2H-1,2'-bipyridine-4-carboxamide

The title compound was prepared using the procedure described in Example 1E using 4-ethylaniline instead of 4-tert-butylaniline. $^1$H NMR (500 MHz, $CDCl_3$) δ 8.19 (dd, 1H), 7.62 (dd, 1H), 7.45 (d, 2H), 7.43 (s(br) 1H), 7.18 (dd.

2H), 6.84 (dd, 1H), 6.75 (m, 1H), 4.12 (dd, 2H), 3.78 (dd, 2H), 2.69 (m, 2H), 2.62 (q, 2H), 1.22 (t, 3H); MS (ESI) 342 (M+H)⁺.

Example 10

3'-chloro-N-(4-isopropylphenyl)-3,6-dihydro-2H-1,2'-bipyridine-4-carboxamide

The title compound was prepared using the procedure described in Example 1E using 4-isopropylaniline instead of 4-tert-butylaniline. ¹H NMR (500 MHz, CDCl₃) δ 8.19 (dd, 1H), 7.61 (dd, 1H), 7.50 (s(br), 1H), 7.46 (d, 2H), 7.18 (dd. 2H), 6.84 (dd, 1H), 6.76 (m, 1H), 4.08 (dd, 2H), 3.56 (dd, 2H), 2.85 (m, 1H), 2.68 (m, 2H), 1.22 (d, 6H); MS (ESI) 356 (M+H)⁺.

Example 11

N-(3-tert-butylphenyl)-3'-chloro-3,6-dihydro-2H-1,2'-bipyridine-4-carboxamide

The title compound was prepared using the procedure described in Example 1E using 3-tert-butylaniline instead of 4-tert-butylaniline. ¹H NMR (500 MHz, CDCl₃) δ 8.19 (dd, 1H), 7.64 (dd, 1H), 7.54 (m, 1H), 7.49 (s(br), 1H), 7.43 (m, 1H), 7.28 (d, 1H), 7.16 (m, 1H), 6.86 (dd, 1H), 6.77 (m, 1H), 4.12 (dd, 2H), 3.60 (dd, 2H), 2.70 (m, 2H), 1.32 (s, 9H); MS (ESI) 369 (M+H)⁺.

Example 12

N-1,1'-biphenyl-4-yl-3'-chloro-3,6-dihydro-2H-1,2'-bipyridine-4-carboxamide

The title compound was prepared using the procedure described in Example 1E using 1,1'-biphenyl-4-ylamine instead of 4-tert-butylaniline. ¹H NMR (500 MHz, CDCl₃) δ 8.19 (dd, 1H), 7.62 (m, 3H), 7.58 (m, 5H), 7.42 (dd, 2H), 7.32 (t, 1H), 6.86 (dd, 1H), 6.77 (m, 1H), 4.12 (dd, 2H), 3.60 (dd, 2H), 2.70 (m, 2H); MS (ESI) 390 (M+H)⁺.

Example 13

3'-chloro-N-(4-propoxyphenyl)-3,6-dihydro-2H-1,2'-bipyridine-4-carboxamide

The title compound was prepared using the procedure described in Example 1E using 4-propoxyaniline instead of 4-tert-butylaniline. ¹H NMR (500 MHz, CDCl₃) δ 8.19 (dd, 1H), 7.60 (dd, 1H), 7.42 (m, 2H), 7.40 (s(br), 1H), 6.85 (m, 3H), 6.75 (m, 1H), 4.08 (dd, 2H), 3.90 (m, 2H), 3.58 (dd, 2H), 2.65 (m, 2H), 1.80 (m, 2H), 1.02 (m, 3H); MS (ESI) 372 (M+H)⁺.

Example 14

3'-chloro-N-[4-(methylthio)phenyl]-3,6-dihydro-2H-1,2'-bipyridine-4-carboxamide

The title compound was prepared using the procedure described in Example 1E using 4-(methylthio)aniline instead of 4-tert-butylaniline. ¹H NMR (500 MHz, CDCl₃) δ 8.20 (dd, 1H), 7.64 (dd, 1H), 7.52 (m, 3H), 7.25 (d, 2H), 6.86 (dd, 1H), 6.76 (m, 1H), 4.12 (dd, 2H), 3.60 (dd, 2H), 2.68 (m, 2H), 2.46 (s, 3H); MS (ESI) 360 (M+H)⁺.

Example 15

3'-chloro-N-(3-fluoro-4-methylphenyl)-3,6-dihydro-2H-1,2'-bipyridine-4-carboxamide The title compound was prepared using the procedure described in Example 1E using 3-fluoro-4-methylaniline instead of 4-tert-butylaniline. ¹H NMR (500 MHz, CDCl₃) δ 8.19 (dd, 1H), 7.62 (dd, 1H), 7.48 (m, 2H), 7.10 (m, 2H), 6.85 (dd, 1H), 6.77 (m, 1H), 4.12 (dd, 2H), 3.58 (dd, 2H), 2.65 (m, 2H), 2.22 (s, 3H); MS (ESI) 346 (M+H)⁺.

Example 16

3'-chloro-N-[4-(trifluoromethyl)phenyl]-3,6-dihydro-2H-1,2'-bipyridine-4-carboxamide The title compound was prepared using the procedure described in Example 1E using 4-(trifluoromethyl)aniline instead of 4-tert-butylaniline. ¹H NMR (500 MHz, CDCl₃) δ 8.19 (dd, 1H), 7.72 (d, 2H), 7.64 (dd, 1H), 7.60 (d, 2H), 7.58 (s(br), 1H), 6.86 (dd, 1H), 6.82 (m, 1H), 4.14 (dd, 2H), 3.59 (dd, 2H), 2.68 (m, 2H); MS (ESI) 382 (M+H)⁺.

Example 17

3'-chloro-N-(3-fluorophenyl)-3,6-dihydro-2H-1,2'-bipyridine-4-carboxamide

The title compound was prepared using the procedure described in Example 1E using 3-fluoroaniline instead of 4-tert-butylaniline. ¹H NMR (500 MHz, CDCl₃) δ 8.19 (dd, 1H), 7.65 (d, 2H), 7.59 (s(br), 1H), 7.54 (m, 1H), 7.24 (m, 1H), 7.19 (m, 1H), 6.86 (dd, 1H), 6.82 (m, 1H), 6.78 (m, 1H), 4.14 (dd, 2H), 3.60 (dd, 2H), 2.66 (m, 2H); MS (ESI) 332 (M+H)⁺.

Example 18

3'-chloro-N-[4-(dimethylamino)phenyl]-3,6-dihydro-2H-1,2'-bipyridine-4-carboxamide The title compound was prepared using the procedure described in Example 1E using N,N-dimethyl-1,4-benzenediamine instead of 4-tert-butylaniline. ¹H NMR (500 MHz, CDCl₃) δ 8.24 (br s, 1H), 8.20 (dd, 1H), 7.76 (m, 3H), 7.48 (d, 2H), 6.85 (dd, 1H), 6.82 (m, 1H), 4.19 (dd, 2H), 3.68 (dd, 2H), 3.17 (s, 6H), 2.68 (m, 2H); MS (ESI) 357 (M+H)⁺.

Example 19

3'-chloro-N-[4-(diethylamino)phenyl]-3,6-dihydro-2H-1,2'-bipyridine-4-carboxamide The title compound was prepared using the procedure described in Example 1E using N,N-diethyl-1,4-benzenediamine instead of 4-tert-butylaniline. ¹H NMR (500 MHz, CDCl₃) δ 8.21 (dd, 1H), 8.04 (s(br), 1H), 7.81 (d, 2H), 7.74 (dd, 1H), 7.51 (d, 2H), 6.92 (dd, 1H), 6.82 (m, 1H), 4.20 (dd, 2H), 3.68 (dd, 2H), 3.52 (m, 4H), 2.69 (m, 2H), 1.15 (t, 6H); MS (ESI) 385 (M+H)⁺.

Example 20

3'-chloro-N-[4-(1-piperidinyl)phenyl]-3,6-dihydro-2H-1,2'-bipyridine-4-carboxamide The title compound was prepared using the procedure described in Example 1E using 4-(1-piperidinyl)aniline instead of 4-tert-butylaniline. $^1$H NMR (500 MHz, CDCl$_3$) δ 8.41 (br s, 1H), 8.20 (dd, 1H), 7.75 (d, 2H), 7.72 (dd, 1H), 7.50 (d, 2H), 6.92 (dd, 1H), 6.82 (m, 1H), 4.16 (dd, 2H), 3.64 (dd, 2H), 3.44 (m, 4H), 2.69 (m, 2H), 2.08 (m, 4H), 1.72 (m, 2H); MS (ESI) 397 (M+H)$^+$.

Example 21

3'-chloro-N-[4-(4-morpholinyl)phenyl]-3,6-dihydro-2H-1,2'-bipyridine-4-carboxamide The title compound was prepared using the procedure described in Example 1E using 4-(4-morpholinyl)aniline instead of 4-tert-butylaniline. $^1$H NMR (500 MHz, CDCl$_3$) δ 8.42 (s(br), 1H), 8.20 (dd, 1H), 7.92 (dd, 1H), 7.76 (d, 2H), 7.44 (d, 2H), 7.04 (dd, 1H), 6.76 (m, 1H), 4.28 (m, 2H), 4.10 (m, 4H), 3.81 (dd, 2H), 3.52 (m, 4H), 2.71 (m, 2H); MS (ESI) 399 (M+H)$^+$.

Example 22

N-[4-(1-azepanyl)phenyl]-3'-chloro-3,6-dihydro-2H-1,2'-bipyridine-4-carboxamide

The title compound was prepared using the procedure described in Example 1E using 4-(1-azepanyl)aniline instead of 4-tert-butylaniline. $^1$H NMR (500 MHz, CDCl$_3$) δ 8.58 (s(br), 1H), 8.20 (dd, 1H), 7.86 (dd, 1H), 7.74 (d, 2H), 7.45 (d, 2H), 7.01 (dd, 1H), 6.78 (m, 1H), 4.24 (m, 2H), 3.75 (dd, 2H), 3.62 (m, 4H), 2.70 (m, 2H), 2.08 (m, 4H), 1.82 (m, 4H); MS (ESI) 411 (M+H)$^+$.

Example 23

N-(4-tert-butylphenyl)-3-(3-chloro-2-pyridinyl)-3,8-diazabicyclo[3.2.1]octane-8-carboxamide

Example 23A methyl 1-benzyl-5-oxo-2-pyrrolidinecarboxylate

1-Benzyl-5-oxo-2-pyrrolidinecarboxylic acid (9.69 g, 44.2 mmol) in methanol (75 mL) was treated with sulfuric acid (0.5 mL) and refluxed for 2.5 hours. The mixture was allowed to cool to room temperature and concentrated under reduced pressure. The residue was dissolved in ethyl acetate and washed with saturated sodium bicarbonate solution. The ethyl acetate phase was concentrated under reduced pressure to provide the title compound which was used in the next step without further purification.

MS (ESI) m/z: 234 (M+H)$^+$; $^1$H NMR (CDCl$_3$) δ 2.08 (m, 1H), 2.25 (m, 1H), 2.43 (m, 1H), 2.55 (m, 1H), 3.68 (s, 3H), 3.99 (dd, 1H), 4.01 (d, 1H), 5.02 (d, 1H), 7.22 (m, 2H), 7.30 (m, 3H).

Example 23B methyl 1-benzyl-5-thioxo-2-pyrrolidinecarboxylate

Methyl 1-benzyl-5-oxo-2-pyrrolidinecarboxylate (18.15 g, 77.8 mmol) and Lawesson's reagent (31.5 g, 77.9 mmol) were combined in dry tetrahydrofuran (100 mL) and stirred overnight at room temperature. The mixture was filtered, the filter cake was rinsed with tetrahydrofuran, and the filtrate was concentrated under reduced pressure. The residue was dissolved in ethyl acetate and washed with saturated sodium bicarbonate solution. The organic phase was concentrated under reduced pressure and the residue was purified by chromatography on silica gel (3:1, hexanes:ethyl acetate) to provide the title compound. MS (ESI) m/z: 250 (M+H)$^+$; $^1$H NMR (CDCl$_3$) δ 2.17 (m, 1H), 2.27 (m, 1H), 3.15 (m, 2H), 3.69 (s, 3H), 4.30 (dd, 1H), 4.37 (d, 1H), 5.73 (d, 1H), 7.32 (m, 5H).

Example 23C 1-benzyl-2-(methoxycarbonyl)-5-(methylthio)-3,4-dihydro-2H-pyrrolium iodide Methyl 1-benzyl-5-thioxo-2-pyrrolidinecarboxylate (16.5 g, 66.2 mmol) in iodomethane (70 mL) was stirred overnight at room temperature. The mixture was concentrated under reduced pressure to provide the title compound which was used in the next step without further purification. $^1$H NMR (CDCl$_3$) δ 2.24 (m, 1H), 3.04 (s, 3H), 3.16 (m, 1H), 3.25 (m, 1H), 3.63 (s, 3H), 4.29 (dd, 1H), 4.72 (d, 1H), 4.89 (dd, 1H), 5.14 (d, 1H), 7.43 (m, 3H), 7.51 (m, 2H).

Example 23D methyl 1-benzyl-5-(nitromethylene)-2-pyrrolidinecarboxylate

1-Benzyl-2-(methoxycarbonyl)-5-(methylthio)-3,4-dihydro-2H-pyrrolium iodide (25.68 g, 65.6 mmol) in dry N,N-dimethylformamide (80 mL) was treated with nitromethane (17.8 mL, 328 mmol) and diisopropylethyl amine (12.6 mL, 72.2 mmol) and stirred overnight at room temperature. The mixture was heated at 60° C. for 5 hours, allowed to cool to room temperature, and concentrated under reduce pressure. The residue was purified by chromatography on silica gel (3:2 hexanes:ethyl acetate) to provide the title compound. MS (ESI) m/z: 277 (M+H)$^+$; $^1$H NMR (CDCl$_3$) δ 2.22 (m, 1H), 2.34 (m, 1H), 3.39 (5, 1H), 3.69 & 3.75 (dd & dd, 1H), 3.72 (s, 3H), 4.24 (dd, 1H), 4.30 (d, 1H), 4.51 (d, 1H), 6.87 (s, 1H), 7.16 (dd, 2H), 7.35 (m, 3H).

Example 23E 8-benzyl-3,8-diazabicyclo[3.2.1]octan-2-one

Methyl 1-benzyl-5-(nitromethylene)-2-pyrrolidinecarboxylate (9.92 g, 35.9 mmol) and 5% platinum on activated carbon (11.25 g) were combined in methanol (100 mL) and shaken for 56 hours at ambient temperature under a hydrogen atmosphere (60 psi). The moisture was filtered and the filtrate concentrated to provide the title compound. MS (DCI/NH$_3$) m/z: 217 (M+H)$^+$.

Example 23F

8-benzyl-3,8-diazabicyclo[3.2.1]octane

8-Benzyl-3,8-diazabicyclo[3.2.1]octan-2-one (5.87 g, 27.1 mmol) in dry tetrahydrofuran (40 mL) was treated with 1M lithium aluminum hydride in THF (81.4 mL), heated at 60° C. for 2 hours, and then allowed to cool to room temperature and stir overnight. The mixture was cooled to 0° C. and treated in succession with water (4.4 mL), tetrahydrofuran (200 mL), 15% sodium hydroxide solution (4.4 mL), and water (13.3 mL). The mixture was filtered and the filter cake was rinsed with ethyl acetate. The filtrate was concentrated under reduced pressure to provide the title compound. MS (DCI/NH$_3$) m/z: 203 (M+H)$^+$.

Example 23G

8-benzyl-3-(trifluoroacetyl)-3,8-diazabicyclo[3.2.1]octane

8-Benzyl-3,8-diazabicyclo[3.2.1]octane (5.18 g, 25.6 mmol) and triethylamine (17.8 mL, 128 mmol) were combined in dry dichloromethane (50 mL) at 0° C., treated with trifluoroacetic anhydride in 1 mL portions (8.9 mL, 64 mmol), and stirred overnight at room temperature. The mixture was concentrated under reduced pressure and the residue was purified by chromatography on silica gel (9:1 hexanes:ethyl acetate) to provide the title compound. MS (DCI/NH$_3$) m/z: 299 (M+H)$^+$; $^1$H NMR (CDCl$_3$) δ 1.66 (m, 2H), 2.06 (br, 2H), 3.08 (d, 1H), 3.25 (d, 2H), 3.53 (m, 4H), 4.12 (d, 1H), 7.34 (m, 5H).

Example 23H tert-butyl 3-(trifluoroacetyl)-3,8-diazabicyclo[3.2.1]octane-8-carboxylate

8-Benzyl-3-(trifluoroacetyl)-3,8-diazabicyclo[3.2.1]octane (1.95 g, 6.54 mmol) and di-tert-butyl dicarbonate (2.14 g, 9.81 mmol) were combined in ethyl acetate (75 mL) and treated with Pearlman's catalyst (216 mg) under a hydrogen atmosphere (1 atmosphere) with stirring for 48 hours at room temperature. The mixture was filtered and the filtrate was concentrated under reduced pressure. The residue in ethyl acetate (150 mL) was treated with L-aspartic acid and stirred for 2 hours. The mixture was washed with saturated sodium bicarbonate solution and concentrated under reduced pressure to provide the title compound. $^1$H NMR (CDCl$_3$) δ 1.48 (s, 9H), 1.70 (m, 2H), 1.98 (m, 2H), 3.06 (d, 1H), 3.45 (d, 1H), 3.70 (d, 1H), 4.23 (d, 1H), 4.30 (br, 2H).

Example 23I tert-butyl 3,8-diazabicyclo[3.2.1]octane-8-carboxylate tert-Butyl 3-(trifluoroacetyl)-3,8-diazabicyclo[3.2.1]octane-8-carboxylate (6.54 mmol) in methanol (85 mL) was treated with ammonium hydroxide (8.5 mL) and stirred overnight at room temperature. The mixture was concentrated under reduced pressure and purified by chromatography on silica gel (5% MeOH, 0.5% NH$_4$OH in CH$_2$Cl$_2$; then 10% MeOH, 1% NH$_4$OH in CH$_2$Cl$_2$) to provide the title compound. MS (DCI/NH$_3$) m/z: 213 (M+H)$^+$; $^1$H NMR (CDCl$_3$) δ 1.47 (s, 9H), 1.81 (m, 2H), 1.94 (m, 2H), 2.65 (dd, 2H), 3.00 (br, 2H), 4.11 (br, 2H).

Example 23J tert-butyl 3-(3-chloro-2-pyridinyl)-3,8-diazabicyclo[3.2.1]octane-8-carboxylate tert-Butyl 3,8-diazabicyclo[3.2.1]octane-8-carboxylate (435 mg, 2.26 mmol), 2-bromo-3-chloropyridine (400 mg, 1.88 mmol), and potassium carbonate (390 mg, 2.83 mmol) were combined in dry dimethylformamide (10 mL) and stirred at 120° C. for 48 hours. The mixture was allowed to cool room temperature, diluted with ethyl acetate, filtered, and the filtrate was concentrated under reduced pressure. The residue was purified by chromatography on silica gel (85:15 hexanes:ethyl acetate) to provide the title compound. MS (ESI) m/z: 268 (100%), 324.0 (M+H)$^+$; $^1$H NMR (CDCl$_3$) δ 1.48 (s, 9H), 1.92 (m, 2H), 2.07 (m, 2H), 3.13 (d, 2H), 3.59 (br, 2H), 4.30 (br, 2H), 6.84 (dd, 1H), 7.58 (dd, 1H), 8.17 (dd, 1H).

Example 23K

3-(3-chloro-2-pyridinyl)-3,8-diazabicyclo[3.2.1]octane tert-Butyl 3-(3-chloro-2-pyridinyl)-3,8-diazabicyclo[3.2.1]octane-8-carboxylate (419 mg, 1.29 mmol) in dry dichloromethane (5 mL) was treated with trifluoroacetic acid and stirred at room temperature for an hour. The mixture was concentrated under reduced pressure and the residue was treated with 1N sodium hydroxide solution. The mixture was extracted with ethyl acetate and the organic phase was concentrated under reduced pressure to provide the title compound. MS (ESI) m/z: 224 (M+H)$^+$; $^1$H NMR (CDCl$_3$) δ 1.86 (m, 2H), 2.09 (m, 2H), 3.09 (d, 2H), 3.63 (m, 4H), 6.81 (dd, 1H), 7.56 (dd, 1H), 8.16 (dd, 1H).

Example 23L

N-(4-tert-butylphenyl)-3-(3-chloro-2-pyridinyl)-3,8-diazabicyclo[3.2.1]octane-8-carboxamide 3-(3-Chloro-2-pyridinyl)-3,8-diazabicyclo[3.2.1]octane (129 mg, 577 µmol) in dry dichloromethane (5 mL) was treated with 1-tert-butyl-4-isocyanatobenzene (101 mg, 577 µmol) and allowed to stir overnight at room temperature. The mixture was concentrated under reduced pressure and the residue was purified by chromatography on silica gel (3:1, hexanes:ethyl acetate) to provide the title compound. MS (DCI/NH$_3$) m/z: 399 (M+H)$^+$; $^1$H NMR (CDCl$_3$) δ 1.30 (s, 9H), 2.01 (m, 2H), 2.17 (m, 2H), 3.25 (d, 2H), 3.64 (dd, 2H), 4.38 (dd, 2H), 6.32 (s, 1H), 6.86 (dd, 1H), 7.32 (s, 4H), 7.59 (dd, 1H), 8.17 (dd, 1H).

Example 24

3-(3-chloro-2-pyridinyl)-N-(3,4-dichlorophenyl)-3,8-diazabicyclo[3.2.1]octane-8-carboxamide The title compound was prepared using the procedure described in Example 23L using 1,2-dichloro-4-isocyanatobenzene instead of 1-tert-butyl-4-isocyanatobenzene. MS (ESI) m/z: 413 (M+H)$^+$; $^1$H NMR (DMSO-d$_6$) δ 1.87 (m, 2H), 2.01 (m, 2H), 3.06 (d, 2H), 3.55 (dd, 2H), 4.53 (s, 2H), 7.01 (dd, 1H), 7.47 (m, 2H), 7.79 (dd, 1H), 7.90 (dd, 1H), 8.21 (dd, 1H), 8.90 (s, 1H).

Example 25

3-(3-chloro-2-pyridinyl)-N-[3-(trifluoromethyl)phenyl]-3,8-diazabicyclo[3.2.1]octane-8-carboxamide The title compound was prepared using the procedure described in Example 23L using 1-isocyanato-3-(trifluoromethyl)benzene instead of 1-tert-butyl-4-isocyanatobenzene. MS (ESI) m/z: 411 (M+H)$^+$; $^1$H NMR (DMSO-d$_6$) δ 1.88 (m, 2H), 2.02 (m, 2H), 3.07 (d, 2H), 3.53 (dd, 2H), 4.55 (dd, 2H), 7.00 (dd, 1H), 7.27 (dd, 1H), 7.48 (t, 1H), 7.80 (dd, 1H), 7.99 (t, 1H), 8.21 (dd, 1H), 8.95 (s, 1H).

Example 26

3-(3-chloro-2-pyridinyl)-N-[4-(trifluoromethyl)phenyl]-3,8-diazabicyclo[3.2.1]octane-8-carboxamide The title compound was prepared using the procedure described in Example 23L using 1-isocyanato-4-(trifluoromethyl)benzene instead of 1-tert-butyl-4-isocyanatobenzene. MS (ESI) m/z: 411 (M+H)$^+$; $^1$H NMR (DMSO-d$_6$) δ 1.88 (m, 2H), 2.02 (m, 2H), 3.07 (d, 2H), 3.55 (dd, 2H), 4.56 (dd, 2H), 7.00 (dd, 1H), 7.60 (d, 2H), 7.75 (d, 2H), 7.80 (dd, 1H), 8.21 (dd, 1H), 9.00 (s, 1H).

Example 27

3-(3-chloro-2-pyridinyl)-N-(4-fluorophenyl)-3,8-diazabicyclo[3.2.1]octane-8-carboxamide The title compound was prepared using the procedure described in Example 23L using 1-fluoro-4-isocyanatobenzene instead of 1-tert-butyl-4-isocyanatobenzene. MS (ESI) m/z: 361 (M+H)$^+$; $^1$H NMR (DMSO-d$_6$) δ 1.86 (m, 2H), 2.00 (m, 2H), 3.06 (d, 2H), 3.53 (dd, 2H), 4.51 (dd, 2H), 7.01 (dd, 1H), 7.08 (t, 2H), 7.51 (dd, 2H), 7.79 (dd, 1H), 8.21 (dd, 1H), 8.65 (s, 1H).

Example 28

N-(4-chlorophenyl)-3-(3-chloro-2-pyridinyl)-3,8-diazabicyclo[3.2.1]octane-8-carboxamide The title compound was prepared using the procedure described in Example 23L using 1-chloro-4-isocyanatobenzene instead of 1-tert-butyl-4-isocyanatobenzene. MS (ESI) m/z: 377 (M+H)$^+$; $^1$H NMR (DMSO-d$_6$) δ 1.86 (m, 2H), 2.00 (m, 2H), 3.06 (d, 2H), 3.54 (dd, 2H), 4.52 (s, 2H), 7.01 (dd, 1H), 7.29 (d, 2H), 7.55 (d, 2H), 7.79 (dd, 1H), 8.21 (dd, 1H), 8.74 (s, 1H).

Example 29

N-(4-bromophenyl)-3-(3-chloro-2-pyridinyl)-3,8-diazabicyclo[3.2.1]octane-8-carboxamide The title compound was prepared using the procedure described in Example 23L using 1-bromo-4-isocyanatobenzene instead of 1-tert-butyl-4-isocyanatobenzene. MS (ESI) m/z: 423 (M+H)$^+$; $^1$H NMR (DMSO-d$_6$) δ 1.86 (m, 2H), 2.00 (m, 2H), 3.06 (d, 2H), 3.54 (dd, 2H), 4.53 (s, 2H), 7.01 (dd, 1H), 7.41 (d, 2H), 7.51 (d, 2H), 7.79 (dd, 1H), 8.21 (dd, 1H), 8.75 (s, 1H).

Example 30

3-(3-chloro-2-pyridinyl)-N-(4-iodophenyl)-3,8-diazabicyclo[3.2.1]octane-8-carboxamide The title compound was prepared using the procedure described in Example 23L using 1-iodo-4-isocyanatobenzene instead of 1-tert-butyl-4-isocyanatobenzene. MS (ESI) m/z: 469 (M+H)$^+$; $^1$H NMR (DMSO-d$_6$) δ 1.86 (m, 2H), 2.00 (m, 2H), 3.05 (d, 2H), 3.53 (dd, 2H), 4.52 (d, 2H), 7.01 (dd, 1H), 7.38 (d, 2H), 7.56 (d, 2H), 7.79 (dd, 1H), 8.21 (dd, 1H), 8.72 (s, 1H).

Example 31

N-(4-butylphenyl)-3-(3-chloro-2-pyridinyl)-3,8-diazabicyclo[3.2.1]octane-8-carboxamide The title compound was prepared using the procedure described in Example 23L using 1-butyl-4-isocyanatobenzene instead of 1-tert-butyl-4-isocyanatobenzene. MS (ESI) m/z: 399 (M+H)$^+$; $^1$H NMR (DMSO-d$_6$) δ 0.89 (t, 3H), 1.29 (6, 2H), 1.52 (5, 2H), 1.86 (m, 2H), 1.99 (m, 2H), 2.50 (t, 2H), 3.06 (d, 2H), 3.52 (dd, 2H), 4.51 (s, 2H), 7.00 (dd, 1H), 7.05 (d, 2H), 7.39 (d, 2H), 7.79 (dd, 1H), 8.21 (dd, 1H), 8.52 (s, 1H).

Example 32

3-(3-chloro-2-pyridinyl)-N-(4-isopropylphenyl)-3,8-diazabicyclo[3.2.1]octane-8-carboxamide The title compound was prepared using the procedure described in Example 23L using 1-isocyanato-4-isopropylbenzene instead of 1-tert-butyl-4-isocyanatobenzene. MS (ESI) m/z: 385 (M+H)$^+$; $^1$H NMR (DMSO-d$_6$) δ 1.17 (d, 6H), 1.86 (m, 2H), 1.99 (m, 2H), 2.81 (7, 2H), 3.06 (d, 2H), 3.52 (dd, 2H), 4.51 (s, 2H), 7.00 (dd, 1H), 7.11 (d, 2H), 7.41 (d, 2H), 7.79 (dd, 1H), 8.21 (dd, 1H), 8.54 (s, 1H).

Example 33

3-(3-chloro-2-pyridinyl)-N-{4-[(trifluoromethyl)thio]phenyl}-3,8-diazabicyclo[3.2.1]octane-8-carboxamide The title compound was prepared using the procedure described in Example 23L using 1-isocyanato-4-[(trifluoromethyl)thio]benzene instead of 1-tert-butyl-4-isocyanatobenzene. MS (ESI) m/z: 443 (M+H)$^+$; $^1$H NMR (DMSO-d$_6$) δ 1.88 (m, 2H), 2.01 (m, 2H), 3.07 (d, 2H), 3.55 (dd, 2H), 4.55 (s, 2H), 7.01 (dd, 1H), 7.58 (d, 2H), 7.70 (d, 2H), 7.80 (dd, 1H), 8.21 (dd, 1H), 8.98 (s, 1H).

Example 34

N-(4-tert-butylphenyl)-8-(3-chloro-2-pyridinyl)-3,8-diazabicyclo[3.2.1]octane-3-carboxamide

Example 34A 8-benzyl-3,8-diazabicyclo[3.2.1]octane tert-Butyl 3-(trifluoroacetyl)-3,8-diazabicyclo[3.2.1]octane-8-carboxylate (1.63 g, 5.46 mmol) in methanol (50 mL) was treated with ammonium hydroxide (7.5 mL) and stirred overnight at room temperature.

Example 34B tert-butyl 8-benzyl-3,8-diazabicyclo[3.2.1]octane-3-carboxylate

8-Benzyl-3,8-diazabicyclo[3.2.1]octane (5.46 mmol) and di-tert-butyl dicarbonate (1.79 g, 8.20 mmol) were combined in ethyl acetate (25 mL) and stirred overnight at room temperature. The mixture was concentrated under reduced pressure, dissolved in ethyl acetate (150 mL), treated with L-aspartic acid (2.18 g, 16.4 mmol), and stirred overnight. The mixture was washed with saturated sodium bicarbonate solution and concentrated under reduced pressure to provide the title compound.

Example 34C tert-butyl 3,8-diazabicyclo[3.2.1]octane-3-carboxylate tert-Butyl 8-benzyl-3,8-diazabicyclo[3.2.1]octane-3-carboxylate (5.46 mmol, 203 mg) and Pearlman's catalyst were combined in methanol under a hydrogen atmosphere (1 atmosphere) stirred overnight at room temperature. Purged with nitrogen, filtered off the catalyst, and concentrated the filtrate to a yellow liquid. The mixture was filtered and the filtrate was concentrated under reduced pressure. The residue was purified by chromatography on silica gel (5% MeOH, 0.5% $NH_4OH$ in $CH_2Cl_2$, then 10% MeOH, 1% $NH_4OH$ in $CH_2Cl_2$) to provide the title compound. MS (DCI/$NH_3$) m/z: 213 (M+H)$^+$; $^1$H NMR (CDCl$_3$) δ 1.45 (s, 9H), 1.75 (br, 4H), 2.93 (d, 1H), 3.01 (d, 1H), 3.47 (d, 2H), 3.68 (d, 1H), 3.81 (d, 1H).

Example 34D tert-butyl 8-(3-chloro-2-pyridinyl)-3,8-diazabicyclo[3.2.1]octane-3-carboxylate tert-Butyl 3,8-diazabicyclo[3.2.1]octane-3-carboxylate (454 mg, 2.36 mmol) and 2-bromo-3-chloropyridine (418 mg, 1.97 mmol) were combined in dry N,N-dimethylformamide (10 mL) and treated with potassium carbonate (408 mg, 2.95 mmol). After stirring at 120° C. for 48 hours, the mixture was allowed to cool to room temperature, diluted with ethyl acetate, filtered, and the filtrate was concentrated under reduced pressure. The residue was purified by chromatography on silica gel (4:1, hexanes:ethyl acetate) to provide the title compound. MS (ESI) m/z: 324 (M+H)$^+$; $^1$H NMR (CDCl$_3$) δ 1.47 (s, 9H), 1.77 (m, 2H), 1.93 (m, 2H), 3.22 (d, 1H), 3.31 (d, 1H), 3.76 (d, 1H), 3.90 (d, 1H), 4.53 (d, 2H), 6.76 (dd, 1H), 7.56 (dd, 1H), 8.09 (dd, 1H).

Example 34E 8-(3-chloro-2-pyridinyl)-3,8-diazabicyclo[3.2.1]octane tert-Butyl 8-(3-chloro-2-pyridinyl)-3,8-diazabicyclo[3.2.1]octane-3-carboxylate (285 mg, 880 µmol) in dry dichloromethane (2 mL) was treated with trifluoroacetic acid (2 mL). After stirring at ambient temperature for 30 minutes, the mixture was concentrated under reduced pressure and the residue was treated with 1N sodium hydroxide solution. The mixture was extracted with ethyl acetate and the organic phase was concentrated under reduced pressure to provide the title compound. MS (DCI/$NH_3$) m/z: 224 (M+H)$^+$; $^1$H NMR (CDCl$_3$) δ 1.87 (m, 2H), 1.97 (m, 2H), 2.75 (dd, 2H), 3.24 (dd, 2H), 4.44 (dd, 2H), 6.73 (dd, 1H), 7.54 (dd, 1H), 8.08 (dd, 1H).

Example 34F

N-(4-tert-butylphenyl)-8-(3-chloro-2-pyridinyl)-3,8-diazabicyclo[3.2.1]octane-3-carboxamide 8-(3-Chloro-2-pyridinyl)-3,8-diazabicyclo[3.2.1]octane (102 mg, 456 µmol) and 1-tert-butyl-4-isocyanatobenzene (80 mg, 456 µmol) were combined in dry dichloromethane (4.5 mL) and stirred overnight at room temperature. The mixture was concentrated and the residue was purified by chromatography on silica gel (7:3, hexanes:ethyl acetate) to provide the title compound. MS (ESI) m/z: 399 (M+H)$^+$; $^1$H NMR (DMSO-d$_6$) δ 1.25 (s, 9H), 1.73 (m, 2H), 1.85 (m, 2H), 3.20 (dd, 2H), 3.92 (dd, 2H), 4.51 (dd, 2H), 6.94 (dd, 1H), 7.24 (d, 2H), 7.37 (d, 2H), 7.79 (dd, 1H), 8.17 (dd, 1H), 8.30 (s, 1H).

Example 35

8-(3-chloro-2-pyridinyl)-N-[4-(trifluoromethyl)phenyl]-3,8-diazabicyclo[3.2.1]octane-3-carboxamide The title compound was prepared using the procedure described in Example 34F using 1-isocyanato-4-(trifluoromethyl)benzene instead of 1-tert-butyl-4-isocyanatobenzene. MS (ESI) m/z: 411 (M+H)$^+$; $^1$H NMR (DMSO-d$_6$) δ 1.74 (m, 2H), 1.87 (m, 2H), 3.25 (d, 2H), 3.95 (dd, 2H), 4.53 (dd, 2H), 6.95 (dd, 1H), 7.58 (d, 2H), 7.70 (d, 2H), 7.80 (dd, 1H), 8.17 (dd, 1H), 8.78 (s, 1H).

Example 37

N-(4-tert-butylphenyl)-1-(3-chloro-2-pyridinyl)-(cis)-3-hydroxy-4-piperidinecarboxamide

Example 37A ethyl 1-benzyl-3-hydroxy-4-piperidinecarboxylate

Ethyl 1-benzyl-3-oxo-4-piperidinecarboxylate (1.0 g, 3.8 mmol) in diethyl ether (50 mL) was treated with lithium aluminumhydride (150 mg, 3.9 mmol) at and −78° C. After stirring at −78° C. for 30 minutes, the mixture was allowed to warm to room temperature over 2 hours. The mixture was quenched with saturated ammonium chloride. Standard work-up gave a crude product which was purified via chromatography (SiO$_2$, ethyl acetate:hexanes, 1:6) to provide the title compound. MS (EI, M+H)$^+$ 264.

Example 37B ethyl 3-hydroxy-4-piperidinecarboxylate

Ethyl 1-benzyl-3-hydroxy-4-piperidinecarboxylate in ethanol (10 mL) was treated with Pd(OH)$_2$ (20% on carbon, 50 mg) under a hydrogen atmosphere (1 atm) and stirred for 5 hours. The reaction mixture was filtered and the filtrate was concentrated under reduced pressure.

Example 37C ethyl 1-(3-chloro-2-pyridinyl)-3-hydroxy-4-piperidinecarboxylate Ethyl 3-hydroxy-4-piperidinecarboxylate, 2-bromo-3-chloropyridine (700 mg, 3.6 mmol), and potassium carbonate (1.0 g, 7.2 mmol) were and heated at 90° C. for 2 days. Standard work-up gave the title compound.

Example 37D 1-(3-chloro-2-pyridinyl)-3-hydroxy-4-piperidinecarboxylic acid

Ethyl 1-(3-chloro-2-pyridinyl)-3-hydroxy-4-piperidinecarboxylate in water (55 mL) was treated with sodium methoxide (0.5 M, 8 mL, 4.0 mmol) at room temperature. After 2 hours, the mixture was concentrated under reduced pressure and the residue was purified by column chromatography to provide the title compound. MS (EI, M+H)$^+$257.

Example 37E

N-(4-tert-butylphenyl)-1-(3-chloro-2-pyridinyl)-(cis)-3-hydroxy-4-piperidinecarboxamide 1-(3-Chloro-2-pyridinyl)-3-hydroxy-4-piperidinecarboxylic acid, tert-butylanaline (255 mg, 1.7 mmol), and EDCI (380 mg, 2.0 mmol) were combined at room temperature. The mixture was allowed to stir for 8 hours and standard work-up provided crude product which was purified by column chromatography to provide the cis and trans analogues. $^1$H NMR (500 MHz, CDCl$_3$) δ 8.15 (dd, 1H), 7.68 (dd, 1H), 7.46 (m, 2H), 7.32 (m, 2H), 6.95 (dd, 1H), 4.32 (m, 1H), 4.08 (m, 1H), 3.95 (m, 1H), 3.25 (m, 2H), 2.56 (m, 1H), 1.92 (m, 2H), 1.28 (s, 9H); MS (ESI, M+H)$^+$ 388.

Example 38

N-(4-tert-butylphenyl)-1-(3-chloro-2-pyridinyl)-(trans)-3-hydroxy-4-piperidinecarboxamide The title compound was isolated from the purification step in Example 37E. $^1$H NMR (500 MHz, CDCl$_3$) δ 8.26 (dd, 1H), 7.96 (s(br), 1H), 7.64 (dd, 1H), 7.45 (m, 2H), 7.34 (m, 2H), 6.86 (dd, 1H), 4.22 (ddd, 1H), 4.05 (m, 1H), 3.96 (m, 1H), 3.02 (m, 1H), 2.94 (m, 1H), 2.42 (m, 1H), 2.14 (m, 1H), 1.96 (m, 1H), 1.30 (s, 9H); MS (ESI, M+H)$^+$ 388.

Example 39

1-(3-chloro-2-pyridinyl)-4-hydroxy-N-[4-(trifluoromethyl)phenyl]-4-piperidinecarboxamide

Example 39A methyl 1-benzyl-4-hydroxy-4-piperidinecarboxylate

1-Benzyl-4-hydroxy-4-piperidinecarbonitrile (30.0 g, 118 mmol) in methanol (590 mL) and concentrated HCl (590 mL) was heated at reflux for 18 hours. The product was obtained following chromatography (SiO$_2$, ethyl acetate:hexane, 1:4). MS (EI, M+H)$^+$ 250.

Example 39B methyl 4-hydroxy-4-piperidinecarboxylate

Methyl 1-benzyl-4-hydroxy-4-piperidinecarboxylate in methanol was treated with Pd(OH)$_2$ (20% on carbon, 500 mg) under a hydrogen atmosphere. The mixture was allowed to stir at room temperature for 12 hours, filtered, and the filtrate was concentrated under reduced pressure.

Example 39C methyl 1-(3-chloro-2-pyridinyl)-4-hydroxy-4-piperidinecarboxylate Methyl 1-benzyl-4-hydroxy-4-piperidinecarboxylate (15.0 g, 77 mmol), 2,3-dichloropyridine (12.0 g, 81 mmol), and potassium carbonate (15.0 g, 108.7 mmol) were combined in DMF (200 mL) and heated at 90° C. for 2 days. The mixture was allowed to cool to room temperature, concentrated, and standard work-up provided a residue that was purified via chromatography (SiO$_2$, ethyl acetate:hexanes, 1:6) to provide the title compound MS (EI, M+H)$^+$ 271.

Example 39D 1-(3-chloro-2-pyridinyl)-4-hydroxy-4-piperidinecarboxylic acid

The title compound was prepared using the procedure described in Example 37D substituting methyl 1-(3-chloro-2-pyridinyl)-4-hydroxy-4-piperidinecarboxylate for ethyl 1-(3-chloro-2-pyridinyl)-3-hydroxy-4-piperidinecarboxylate.

Example 39E 1-(3-chloro-2-pyridinyl)-4-hydroxy-N-[4-(trifluoromethyl)phenyl]-4-piperidinecarboxamide 1-(3-Chloro-2-pyridinyl)-4-hydroxy-4-piperidinecarboxylic acid, EDCI (525 mg, 2.7 mmol), and 4-(trifluoromethyl)aniline in dichloromethane (10 mL) were combined at room temperature and stirred overnight. Standard work-up gave a crude product which was purified via chromatography (SiO$_2$, ethyl acetate:hexanes, 1:9). $^1$H NMR (500 MHz, CDCl$_3$) δ 8.90 (s(br), 1H), 8.20 (dd, 1H), 7.74 (d, 2H), 7.61 (m, 3H), 6.86 (dd, 1H), 3.80 (m, 2H), 3.18 (m, 2H), 2.50 (m, 2H), 1.78 (m, 2H); MS (ESI, M+H)$^+$ 400.

Example 40

N-(4-tert-butylphenyl)-3'-(trifluoromethyl)-3,6-dihydro-2H-1,2'-bipyridine-4-carboxamide

Example 40A

1-[3-(trifluoromethyl)pyridin-2-yl]piperidin-4-one

2-Chloro-3-(trifluoromethyl)pyridine (11.92 g, 65.7 mmol)), K$_2$CO$_3$(19.10 g, 138 mmol), and 1,4-dioxa-8-azaspiro[4.5]decane (8.85 mL, 69.0 mmol) were combined in DMSO (65 mL) and stirred at 100° C. for 3 hours. The mixture was treated with additional 1,4-dioxa-8-azaspiro [4.5]decane (2.0 mL, 16 mmol), stirred for 2 hours, treated with additional 1,4-dioxa-8-azaspiro[4.5]decane (1.0 mL, 7.8 mmol), and stirred for 1 hour. The mixture was diluted with diethyl ether (200 mL), washed with water (250 mL), washed with brine (100 mL), dried (Na$_2$SO$_4$), filtered, and the filtrate was concentrated under reduced pressure. The residue was dissolved in concentrated HCl (25 mL), stirred for 3 hours, basified with concentrated NH$_4$OH, extracted with CH$_2$Cl$_2$, and the phases separated. The organic phase was dried (Na$_2$SO$_4$), filtered, and the filtrate concentrated under reduced pressure. The residue was purified via flash chromatography (20% to 40% diethyl ether/hexanes) to provide the title compound.

Example 40B methyl 3'-(trifluoromethyl)-3,6-dihydro-2H-1,2'-bipyridine-4-carboxylate Lithium diisopropyl amide (37.3 mmol) in THF (75 mL) at −78° C. was treated with 1-[3-(trifluoromethyl)pyridin-2-yl]piperidin-4-one (8.30 g, 34.0 mmol) in THF (25 mL) and stirred for 45 minutes. The mixture was treated with solid PhNTf$_2$ (14.0 g, 39.1 mmol), stirred for 1 hour, and concentrated under reduced pressure. The residue was diluted with ethyl acetate:hexanes (1:1), washed with 1N NaOH, dried (Na$_2$SO$_4$), filtered through a silica plug, and the filtrate was concentrated under reduced pressure. The residue, triethylamine (14.2 mL, 102 mmol), and PdCl$_2$(PPh$_3$)$_2$ (0.944 g, 1.34 mmol) were combined in methanol (7.00 mL, 173 mmol) and DMF (100 mL) and saturated with carbon monoxide gas (bubbling 15 minutes). The mixture was heated at 80° C. under a carbon monoxide atmosphere (1 atm) overnight. The mixture was concentrated to half volume, diluted with diethyl ether, washed with water, brine, dried (Na$_2$SO$_4$), filtered, and the filtrate was concentrated under reduced pressure. The residue was purified by flash chromatography (6% ethyl acetate/hexanes) to provide the title compound.

Example 40C

3'-(trifluoromethyl)-3,6-dihydro-2H-1,2'-bipyridine-4-carboxylic acid

Methyl 3'-(trifluoromethyl)-3,6-dihydro-2H-1,2'-bipyridine-4-carboxylate (15 mL) in THF (30 mL) was treated with 1N NaOH (27 mL) and stirred for 2 hours. The mixture was treated with additional 1N NaOH (16 mL), stirred for 1 hour, treated with 1N NaOH (14.5 mL), and stirred for 1 hour. The mixture was diluted with water and extracted with CH$_2$Cl$_2$. The aqueous layer was then acidified with concentrated HCl and extracted with CHCl$_3$. The organic layer was dried (Na$_2$SO$_4$), filtered, and the filtrate was concentrated under reduced pressure to provide the title compound.

Example 40D

N-(4-tert-butylphenyl)-3'-(trifluoromethyl)-3,6-dihydro-2H-1,2'-bipyridine-4-carboxamide 3'-(Trifluoromethyl)-3,6-dihydro-2H-1,2'-bipyridine-4-carboxylic acid (0.300 g, 1.10 mmol) and a catalytic amount of DMF were combined in CH$_2$Cl$_2$ (4.0 mL) and treated with (COCl)$_2$ (0.14 mL, 1.6 mmol). The mixture was stirred for 90 minutes, diluted with toluene (0.5 mL) and concentrated to dryness. The residue was dissolved in CH$_2$Cl$_2$ (4.0 mL) treated with pyridine (0.14 mL, 1.7 mmol), a catalytic amount of DMAP, and 4-tert-butylaniline (0.21 mL, 1.3 mmol). After 1 hour, the mixture was diluted with water and extracted with CH$_2$Cl$_2$. The organic phase was dried (Na$_2$SO$_4$), filtered, and the filtrate was concentrated under reduced pressure. The residue was purified by flash chromatography (2.5% ethyl acetate/CH$_2$Cl$_2$) to provide the title compound. $^1$H NMR (300 MHz, CDCl$_3$) δ 8.42 (dd, 1H), 7.89 (dd, 1H), 7.47 (d, 3H), 6.98 (dd, 1H), 6.76 (s, 1H), 4.06 (q, 2H), 3.53 (t, 2H), 2.67 (m, 2H); MS (m/z) 404.

Example 41

N-(4-chlorophenyl)-3'-(trifluoromethyl)-3,6-dihydro-2H-1,2'-bipyridine-4-carboxamide The title compound was prepared using the procedure described in Example 40D using 4-chloroaniline instead of 4-tert-butylaniline. $^1$H NMR (300 MHz, CDCl$_3$) δ 8.42 (dd, 1H), 7.89 (dd, 1H), 7.51 (dd, 2H), 7.43 (brs, 1H), 7.30 (d, 2H), 6.99 (dd, 1H), 6.77 (sept, 1H), 4.05 (q, 2H), 3.51 (t, 2H), 2.65 (m, 2H); MS (m/z) 382.

Example 42

N-[4-(trifluoromethoxy)phenyl]-3'-(trifluoromethyl)-3,6-dihydro-2H-1,2'-bipyridine-4-carboxamide The title compound was prepared using the procedure described in Example 40D using 4-(trifluoromethoxy)aniline instead of 4-tert-butylaniline. $^1$H NMR (300 MHz, CDCl$_3$) δ 8.44 (dd, 1H), 7.90 (dd, 1H), 7.59 (d, 2H), 7.48 (brs, 1H), 7.20 (d, 2H), 7.00 (dd, 1H), 6.79 (m, 1H), 4.07 (q, 2H), 3.53 (t, 2H), 2.67 (m, 2H); MS (m/z) 432.

Example 43

3'-(trifluoromethyl)-N-{4-[(trifluoromethyl)thio]phenyl}-3,6-dihydro-2H-1,2'-bipyridine-4-carboxamide The title compound was prepared using the procedure described in Example 40D using 4-[(trifluoromethyl)thio]aniline instead of 4-tert-butylaniline. $^1$H NMR (300 MHz, CDCl$_3$) δ 8.43 (dd, 1H), 7.90 (dd, 1H), 7.66 (d, 2H), 7.62 (d, 2H), 7.53 (brs, 1H), 7.00 (dd, 1H), 6.79 (m, 1H), 4.07 (q, 2H), 3.52 (t, 2H), 2.67 (m, 2H); MS (m/z) 448.

Example 44

3'-(trifluoromethyl)-N-{4-[(trifluoromethyl)sulfonyl]phenyl}-3,6-dihydro-2H-1,2'-bipyridine-4-carboxamide The title compound was prepared using the procedure described in Example 40D using 4-[(trifluoromethyl)sulfonyl]aniline instead of 4-tert-butylaniline. $^1$H NMR (300 MHz, CDCl$_3$) δ 8.43 (dd, 1H), 8.00 (dd, 1H), 7.88-7.92 (m, 3H), 7.75 (brs, 1H), 7.02 (dd, 1H), 6.85 (m, 1H), 4.09 (q, 2H), 3.52 (t, 2H), 2.68 (m, 2H); MS (m/z) 480.

Example 45

N-(3-fluoro-4-methylphenyl)-3'-(trifluoromethyl)-3,6-dihydro-2H-1,2'-bipyridine-4-carboxamide The title compound was prepared using the procedure described in Example 40D using 3-fluoro-4-methylaniline instead of 4-tert-butylaniline. $^1$H NMR (300 MHz, CDCl$_3$) δ 8.42 (dd, 1H), 7.88 (dd, 1H), 7.47 (dd, 1H), 7.40 (brs, 1H), 7.05-7.15 (m, 2H), 6.98 (dd, 1H), 6.76 (sept, 1H), 4.05 (q, 2H), 3.51 (t, 2H), 2.66 (m, 2H); MS (m/z) 380.

Example 46

N-(4-chlorophenyl)-1-pyrimidin-2-yl-1,2,3,6-tetrahydropyridine-4-carboxamide

Example 46A 1-pyrimidin-2-yl-1,2,3,6-tetrahydropyridine-4-carboxylic acid

2-Chloropyrimidine (0.570 g, 4.98 mmol) and 1,2,3,6-tetrahydro-4-pyridinecarboxylic acid (1.22 g) were combined in water (7 mL) and heated at 90° C. After 4 hours, the mixture was treated with additional 1,2,3,6-tetrahydro-4-pyridinecarboxylic acid (0.52 g) and stirred overnight. The mixture was diluted with water and extracted with $CH_2Cl_2$. The aqueous layer was acidified with concentrated HCl (pH~3) and extracted with $CHCl_3$. The organic layer was dried ($Na_2SO_4$), filtered, and the filtrate was concentrated under reduced pressure to provide the title.

Example 46B

N-(4-chlorophenyl)-1-pyrimidin-2-yl-1,2,3,6-tetrahydropyridine-4-carboxamide

1-Pyrimidin-2-yl-1,2,3,6-tetrahydropyridine-4-carboxylic acid (55.0 mg, 0.27 mmol) and a catalytic amount of DMF were combined in $CH_2Cl_2$ (1.5 mL) and treated with $(COCl)_2$ (0.033 mL, 0.38 mmol). The mixture was stirred for 90 minutes, diluted with toluene (0.5 mL), and concentrated to dryness under reduced pressure. The residue in $CH_2Cl_2$ (1.5 mL) was treated with pyridine (0.033 mL, 0.41 mmol), catalytic amount of DMAP, and 4-chloroaniline (41.0 mg, 0.32 mmol). The mixture was stirred for 1 hour, diluted with water, and extracted with $CH_2Cl_2$. The organic phase was dried ($Na_2SO_4$), filtered, and the filtrate was concentrated under reduced pressure. The residue was purified by flash chromatography (15% ethyl acetate/$CH_2Cl_2$) to provide the title compound. $^1$H NMR (300 MHz, $CDCl_3$) δ 8.35 (d, 2H), 7.51 (d, 2H), 7.39 (brs, 1H), 7.31 (d, 2H), 6.77 (sept, 1H), 6.54 (t, 1H), 4.43 (q, 2H), 4.03 (t, 2H), 2.58 (m, 2H); MS (m/z) 315.

Example 47

1-pyrimidin-2-yl-N-{4-[(trifluoromethyl)thio]phenyl}-1,2,3,6-tetrahydropyridine-4-carboxamide The title compound was prepared using the procedure described in Example 46B using 4-[(trifluoromethyl)thio] aniline instead of 4-chloroaniline. $^1$H NMR (300 MHz, $CDCl_3$) δ 8.35 (d, 2H), 7.64 (s, 4H), 7.50 brs, 1H), 6.78 (sept, 1H), 6.56 (t, 1H), 4.45 (q, 2H), 4.05 (t, 2H), 2.59 (m, 2H); MS (m/z) 381.

Example 48

1-pyrimidin-2-yl-N-{4-[(trifluoromethyl)sulfonyl] phenyl}-1,2,3,6-tetrahydropyridine-4-carboxamide The title compound was prepared using the procedure described in Example 46B using 4-[(trifluoromethyl)sulfonyl]aniline instead of 4-chloroaniline. $^1$H NMR (300 MHz, $CDCl_3$) δ 8.36 (d, 2H), 8.00 (d, 2H), 7.90 (d, 2H), 7.72 (brs, 1H), 6.84 (m, 1H), 6.57 (t, 1H), 4.48 (q, 2H), 4.06 (t, 2H), 2.61 (m, 2H); MS (m/z) 413.

The foregoing is merely illustrative and is not intended to limit the invention to the disclosed compounds. Variations and changes which are obvious to one skilled in the art are to be within the scope and nature of the invention which are defined in the appended claims.

Example 49

3'-Trifluoromethyl-3,6-dihydro-2H-[1,2']bipyridinyl-4-carboxylic acid (4-tert-butyl-phenyl)-amide

Example 49A

3'-Trifluoromethyl-2,3,5,6-tetrahydro-[1,2']bipyridinyl-4-one

A suspension of $K_2CO_3$ (19.10 g, 138 mmol), 2-chloro-3-(trifluoromethyl)pyridine (11.92 g, 65.7 mmol)) and 1,4-Dioxa-8-aza-spiro[4.5]decane (8.85 mL, 69.0 mmol) in DMSO (65 mL) was stirred at 100° C. for 3 hour. Additional 1,4-Dioxa-8-aza-spiro[4.5]decane (2.0 mL, 16 mmol) was added and stirred for an additional 2 hour, followed by another aliquot (1.0 mL, 7.8 mmol) and stirring for 1 hour. The mixture was diluted with $Et_2O$ (200 mL), and washed with water (250 mL), washed with brine (100 mL), and the organic layer dried ($Na_2SO_4$), filtered and concentrated under reduced pressure. The residue was then dissolved in conc HCl (25 mL), stirred 3 hour, basified with conc $NH_4OH$, extracted with $CH_2Cl_2$, and dried ($Na_2SO_4$), and concentrated. Flash chromatographic purification (20 to 40% $Et_2O$/Hex gradient elution) provided the substituted piperidone as a yellow solid (8.35 g, 34.2 mmol, 52%): $^1$H NMR (300 MHz, $CDCl_3$) δ 8.46 (d, J=4.6 Hz, 1H), 7.92 (d, J=7.6 Hz, 1H), 7.07 (dd, J=4.6, 7.6 Hz, 1H), 3.59 (t, J=5.9 Hz, 4H), 2.61 (t, J=5.9 Hz, 4H).

Example 49B

3'-Trifluoromethyl-3,6-dihydro-2H-[1,2']bipyridinyl-4-carboxylic acid methyl ester A solution of the piperidone (8.30 g, 34.0 mmol) in THF (25 mL) was added to a solution of LDA (lithium diisopropylamine) (37.3 mmol) in THF (75 mL) at −78° C., and stirred 45 minutes. Solid $PhNTf_2$ (14.0 g, 39.1 mmol) was then added, and stirred for 1 hour. The mixture was concentrated under reduced pressure and diluted with 1:1 EtOAc:hexane, and washed with 1 N NaOH. The organic layer was dried ($Na_2SO_4$), and filtered through a silica plug, and concentrated under reduced pressure to provide 14.4 g of a red oil. This residue and $Et_3N$ (14.2 mL, 102 mmol) and MeOH (7.00 mL, 173 mmol) were dissolved in DMF (100 mL), and saturated with CO (bubbling 15 minutes). Solid $PdCl_2(PPh_3)_2$ (0.944 g, 1.34 mmol) was added, and the mixture was heated to 80° C. under CO (1 atm) overnight. The mixture was then concentrated under reduced pressure to half volume, diluted with $Et_2O$, washed with water, brine, dried ($Na_2SO_4$), concentrated under reduced pressure and purified by flash chromatography (6% EtOAc/hexane) to provide the methyl ester as a yellow solid (3.90 g, 13.6 mmol, 40%): $^1$H NMR (300 MHz, $CDCl_3$) δ 8.40 (dd, J=1.7, 4.8 Hz, 1H), 7.87 (dd, J=1.7, 7.8 Hz, 1H), 7.01 (sept, J=1.7 Hz, 1H), 6.96 (ddd, J=1.0, 4.8, 7.8 Hz, 1H), 4.03 (q, J=3.0 Hz, 2H), 3.77 (s, 3H), 3.44 (t, J=5.4 Hz, 2H).

Example 49C

3'-Trifluoromethyl-3,6-dihydro-2H-[1,2']bipyridinyl-4-carboxylic acid

The ester was dissolved in MeOH (15 mL) and THF (30 mL), and stirred with 1 N NaOH (27 mL) for 2 hour. Additional 1 N NaOH (16 mL) was added and stirred for 1 hour, followed by another aliquot (14.5 mL) for 1 hour. The mixture was then diluted with water, and extracted with $CH_2Cl_2$. The aqueous layer was then acidified with conc HCl and extracted with $CHCl_3$. The organic layer was dried ($Na_2SO_4$) and concentrated under reduced pressure to provide 13c a tan solid (3.00 g, 11.0 mmol, 81%): $^1$H NMR (300 MHz, $CD_3OD$) δ 8.45 (m, 1H), 7.99 (dd, J=2.4, 7.8 Hz, 1H), 7.11 (m, 1H), 7.02 (sept, J=1.7 Hz, 1H), 3.99 (q, J=3.1 Hz, 2H), 3.39 (t, J=5.6 Hz, 2H), 2.49 (m, 2H).

Example 49D

3'-Trifluoromethyl-3,6-dihydro-2H-[1,2']bipyridinyl-4-carboxylic acid (4-tert-butyl-phenyl)-amide To a suspension of 3'-trifluoromethyl-3,6-dihydro-2H-[1,2']bipyridinyl-4-carboxylic acid (60.4 mg, 0.194 mmol) and DMF (cat) in $CH_2Cl_2$ (1 mL) was added $(COCl)_2$ (0.027 mL, 0.31 mmol). The mixture was stirred for 90 minutes, diluted with PhMe (0.5 mL), concentrated under reduced pressure to dryness, and dissolved in $CH_2Cl_2$ (1.5 mL). To the solution were added pyridine (0.027 mL, 0.33 mmol), DMAP (cat), and 4-tert-butylaniline (0.037 mL, 0.023 mmol). The mixture was stirred 1 hour, diluted with water and extracted with $CH_2Cl_2$, dried ($Na_2SO_4$), and purified by flash chromatography (7% $EtOAc/CH_2Cl_2$) to provide as a white solid (54.2 mg, 0.123 mmol, 63%): MS (ESI+) m/z 404 $(M+H)^+$, m/z 402 $(M-H)^-$; 1H NMR (300 MHz, CHLOROFORM-D) δ ppm 1.31 (s, 9 H), 2.67 (m, 2 H), 3.53 (t, J=5.4 Hz, 2 H), 4.07 (q, J=2.9 Hz, 2 H), 6.76 (m, 1 H), 6.98 (dd, J=7.5, 4.4 Hz, 1 H), 7.36 (m, 3 H), 7.48 (m, 2 H), 7.89 (dd, J=7.8, 1.7 Hz, 1 H), 8.42 (dd, J=4.7, 1.4 Hz, 1 H).

Example 50

3'-Chloro-3,6-dihydro-2H-[1,2']bipyridinyl-4-carboxylic acid (4-azepan-1-yl-phenyl)-amide The title compound was prepared using the procedure described in Example 49D using 4-Azepan-1-yl-phenylamine instead of 4-tert-butylaniline. MS (ESI+) m/z 411 $(M+H)^+$, m/z 409 $(M-H)^-$; 1H NMR (500 MHz, CHLOROFORM-D) δ ppm 1.82 (s, 4 H), 2.09 (s, 4 H), 2.71 (d, J=1.6 Hz, 2 H), 3.63 (m, 4 H), 3.76 (t, J=5.6 Hz, 2 H), 4.25 (d, J=2.8 Hz, 2 H), 6.77 (s, 1 H), 7.01 (dd, J=7.8, 5.3 Hz, 1 H), 7.46 (d, J=9.0 Hz, 2 H), 7.74 (d, J=9.0 Hz, 2 H), 7.87 (dd, J=7.8, 1.6 Hz, 1 H), 8.20 (dd, J=5.3, 1.6 Hz, 1 H), 8.59 (s, 1 H).

Example 51

3'-Chloro-3,6-dihydro-2H-[1,2']bipyridinyl-4-carboxylic acid (1-tert-butyl-1H-pyrazol-4-yl)-amide The title compound was prepared using the procedure described in Example 49D using 4-1-tert-butyl-1H-pyrazol-4-ylamine instead of 4-tert-butylaniline. $^1$H NMR (300 MHz, DMSO-D6) δ ppm 1.50 (s, 9 H), 2.53 (s, 2 H), 3.45 (t, J=5.6 Hz, 2 H), 3.99 (q, J=2.7 Hz, 2 H), 6.74 (s, 1 H), 7.00 (dd, J=7.8, 4.7 Hz, 1 H), 7.53 (s, 1 H), 7.82 (dd, J=7.8, 1.7 Hz, 1 H), 7.99 (s, 1 H), 8.22 (m, 1 H), 9.85 (s, 1 H).

Example 52

1-Pyrimidin-2-yl-1,2,3,6-tetrahydro-pyridine-4-carboxylic acid (4-tert-butyl-phenyl)-amide

Example 52A

1-Pyrimidin-2-yl-1,2,3,6-tetrahydro-pyridine-4-carboxylic acid

A mixture of 2-chloropyrimidine (0.570 g, 4.98 mmol), and isoguvacine, sodium salt (1.2 g, 8.2 mmol) in water (7 mL) was heated to 90° C. and stirred for 4 hour. Additional isoguvacine, sodium salt (0.52 g, 3.3 mmol) was then added and stirred overnight. The mixture was diluted with water and extracted with $CH_2Cl_2$. The aqueous layer was acidified with conc HCl (pH~3) and extracted with $CHCl_3$. The organic layer was dried ($Na_2SO_4$), filtered and concentrated under reduced pressure to provide 1-Pyrimidin-2-yl-1,2,3,6-tetrahydro-pyridine-4-carboxylic acid a white solid (0.564 g, 2.75 mmol, 55%): $^1$H NMR (300 MHz, $CD_3OD$) δ 8.43 (d, J=4.8 Hz, 2H), 7.02 (sept, J=1.7 Hz, 1H), 6.74 (t, J=4.8 Hz, 1H), 4.39 (q, J=3.0 Hz, 2H), 3.97 (t, J=5.8 Hz, 2H), 2.49 (m, 2H).

Example 52B

1-Pyrimidin-2-yl-1,2,3,6-tetrahydro-pyridine-4-carboxylic acid (4-tert-butyl-phenyl)-amide To a suspension of 1-Pyrimidin-2-yl-1,2,3,6-tetrahydro-pyridine-4-carboxylic acid (60.4 mg, 0.194 mmol) and DMF (cat) in $CH_2Cl_2$ (1 mL) was added $(COCl)_2$ (0.027 mL, 0.31 mmol). The mixture was stirred for 90 minutes, diluted with PhMe (0.5 mL), concentrated under reduced pressure to dryness, and dissolved in $CH_2Cl_2$ (1.5 mL). To the solution were added pyridine (0.027 mL, 0.33 mmol), DMAP (cat), and 4-tert-butylaniline (0.037 mL, 0.023 mmol). The mixture was stirred 1 hour, diluted with water and extracted with $CH_2Cl_2$, dried ($Na_2SO_4$), and purified by flash chromatography (7% $EtOAc/CH_2Cl_2$) to provide 1-Pyrimidin-2-yl-1,2,3,6-tetrahydro-pyridine-4-carboxylic acid (4-tert-butyl-phenyl)-amide as a white solid (54.2 mg, 0.123 mmol, 63%): MS (ESI+) m/z 337 $(M+H)^+$, m/z 334 $(M-H)^-$; 1H NMR (300 MHz, CHLOROFORM-D) δ ppm 1.31 (s, 9 H), 2.59 (m, 2 H), 4.04 (t, J=5.6 Hz, 2 H), 4.44 (q, J=3.1 Hz, 2 H), 6.54 (t, J=4.7 Hz, 1 H), 6.75 (m, 1 H), 7.36 (m, 3 H), 7.47 (m, 2 H), 8.35 (d, J=4.7 Hz, 2 H).

Example 53

1-Pyrimidin-2-yl-1,2,3,6-tetrahydro-pyridine-4-carboxylic acid (4-chloro-phenyl)-amide The title compound was prepared using the procedure described in Example 52B using 4-chloro-aniline instead of 4-ter-butylaniline. MS (ESI+) m/z 315 $(M+H)^+$; 1H NMR (300 MHz, CHLOROFORM-D) δ ppm 2.58 (m, 2 H), 4.03 (t, J=5.6 Hz, 2 H), 4.44 (q, J=3.1 Hz, 2 H), 6.54 (t, J=4.7 Hz, 1 H), 6.77 (m, 1 H), 7.30 (d, J=9.2 Hz, 2 H), 7.39 (s, 1 H), 7.52 (d, J=8.8 Hz, 2 H), 8.35 (d, J=4.7 Hz, 2 H).

Example 54

1-Pyrimidin-2-yl-1,2,3,6-tetrahydro-pyridine-4-carboxylic acid (4-trifluoromethyoxy-phenyl)-amide

The title compound was prepared using the procedure described in Example 52B using 4-trifluoromethoxy-aniline instead of 4-ter-butylaniline. MS (ESI+) m/z 365 (M+H)$^+$, m/z 363 (M−H)$^-$; 1H NMR (300 MHz, CHLOROFORM-D) δ ppm 2.59 (m, 2 H), 4.04 (t, J=5.6 Hz, 2 H), 4.44 (q, J=3.1 Hz, 2 H), 6.55 (t, J=4.7 Hz, 1 H), 6.77 (m, 1 H), 7.19 (d, J=9.2 Hz, 2 H), 7.44 (s, 1 H), 7.59 (d, J=9.2 Hz, 2 H), 8.35 (d, J=4.7 Hz, 2 H).

Example 55

1-Pyrimidin-2-yl-1,2,3,6-tetrahydro-pyridine-4-carboxylic acid (4-trifluoromethylsulfanyl-phenyl)-amide

The title compound was prepared using the procedure described in Example 52B using 4-trifluoromethylsulfanyl-aniline instead of 4-ter-butylaniline. MS (ESI+) m/z 381 (M+H)$^+$, m/z 379 (M−H)$^-$; 1H NMR (300 MHz, DMSO-D6) δ ppm 2.47 (s, 2 H), 3.93 (t, J=5.8 Hz, 2 H), 4.38 (q, J=2.7 Hz, 2 H), 6.69 (t, J=4.7 Hz, 1 H), 6.84 (m, 1 H), 7.66 (d, J=8.8 Hz, 2 H), 7.86 (d, J=8.8 Hz, 2 H), 8.42 (d, J=5.1 Hz, 2 H), 10.09 (s, 1 H).

Example 56

1-Pyrimidin-2-yl-1,2,3,6-tetrahydro-pyridine-4-carboxylic acid (4-trifluoromethanesulfonyl-phenyl)-amide

The title compound was prepared using the procedure described in Example 52B using 4-trifluoromethylsulfonyl-aniline instead of 4-ter-butylaniline. MS (ESI+) m/z 413 (M+H)$^+$, m/z 411 (M−H)$^-$; 1H NMR (300 MHz, CHLOROFORM-D) δ ppm 2.61 (s, 2 H), 4.06 (t, J=5.6 Hz, 2 H), 4.49 (q, J=2.9 Hz, 2 H), 6.57 (t, J=4.7 Hz, 1 H), 6.84 (s, 1 H), 7.72 (s, 1 H), 7.89 (d, J=8.8 Hz, 2 H), 8.01 (d, J=8.8 Hz, 2 H), 8.36 (d, J=4.7 Hz, 2 H).

Example 57

3'-Chloro-3,6-dihydro-2H-[1,2']bipyridinyl-4-carboxylic acid (4-bromo-3-fluoro-phenyl)-amide

The title compound was prepared using the procedure described in Example 52B using 4-bromo-3-fluoro-aniline instead of 4-ter-butylaniline. MS (ESI+) m/z 411 (M+H)$^+$, m/z 409 (M−H)$^-$; 1H NMR (300 MHz, DMSO-D6) δ ppm 2.55 (d, J=1.7 Hz, 2 H), 3.45 (t, J=5.6 Hz, 2 H), 4.02 (q, J=2.9 Hz, 2 H), 6.82 (s, 1 H), 7.01 (dd, J=7.8, 4.7 Hz, 1 H), 7.47 (dd, J=8.8, 2.4 Hz, 1 H), 7.63 (t, J=8.8 Hz, 1 H), 7.82 (d, J=1.4 Hz, 1 H), 7.85 (dd, J=4.9, 1.9 Hz, 1 H), 8.22 (dd, J=4.7, 1.7 Hz, 1 H), 10.05 (s, 1 H).

Example 58

3'-Chloro-3,6-dihydro-2H-[1,2']bipyridinyl-4-carboxylic acid (4-bromo-3-methyl-phenyl)-amide

The title compound was prepared using the procedure described in Example 49D using 4-bromo-3-methyl-aniline instead of 4-ter-butylaniline. MS (ESI+) m/z 407 (M+H)$^+$, m/z 405 (M−H)[31]; 1H NMR (300 MHz, DMSO-D6) δ ppm 2.32 (s, 3 H), 2.56 (s, 2 H), 3.44 (t, J=5.4 Hz, 2 H), 4.01 (q, J=2.7 Hz, 2 H), 6.79 (s, 1 H), 7.00 (dd, J=7.8, 4.7 Hz, 1 H), 7.49 (s, 2 H), 7.71 (s, 1 H), 7.83 (dd, J=7.6, 1.5 Hz, 1 H), 8.22 (dd, J=4.7, 1.7 Hz, 1 H), 9.78 (s, 1 H).

Example 59

3'-Trifluoromethyl-3,6-dihydro-2H-[1,2']bipyridinyl-4-carboxylic acid (4-chloro-phenyl)-amide

The title compound was prepared using the procedure described in Example 49D using 4-chloro-aniline instead of 4-ter-butylaniline. MS (ESI+) m/z 382 (M+H)$^+$, m/z 380 (M−H)$^-$; 1H NMR (300 MHz, CHLOROFORM-D) δ ppm 2.66 (m, 2 H), 3.51 (t, J=5.6 Hz, 2 H), 4.06 (q, J=3.1 Hz, 2 H), 6.77 (m, 1 H), 6.99 (dd, J=8.1, 4.4 Hz, 1 H), 7.30 (m, 2 H), 7.43 (s, 1 H), 7.52 (m, 2 H), 7.89 (dd, J=7.8, 1.7 Hz, 1 H), 8.42 (dd, J=4.7, 1.4 Hz, 1 H).

Example 60

3'-Trifluoromethyl-3,6-dihydro-2H-[1,2']bipyridinyl-4-carboxylic acid (4-trifluoromethoxy-phenyl)-amide

The title compound was prepared using the procedure described in Example 49D using 4-trifluoromethoxy-aniline instead of 4-ter-butylaniline. MS (ESI+) m/z 432 (M+H)$^+$, m/z 430 (M−H)$^-$; 1H NMR (300 MHz, CHLOROFORM-D) δ ppm 2.67 (m, 2 H), 3.53 (t, J=5.4 Hz, 2 H), 4.08 (q, J=2.7 Hz, 2 H), 6.79 (s, 1 H), 7.00 (dd, J=7.8, 4.7 Hz, 1 H), 7.20 (d, J=8.1 Hz, 2 H), 7.48 (s, 1 H), 7.60 (d, J=9.2 Hz, 2 H), 7.90 (dd, J=7.8, 1.7 Hz, 1 H), 8.43 (dd, J=4.9, 1.2 Hz, 1 H).

Example 61

3'-Trifluoromethyl-3,6-dihydro-2H-[1,2']bipyridinyl-4-carboxylic acid (4-trifluoromethylsulfanyl-phenyl)-amide

The title compound was prepared using the procedure described in Example 49D using 4-trifluoromethylsulfanyl-aniline instead of 4-ter-butylaniline. MS (ESI+) m/z 448 (M+H)$^+$, m/z 446 (M−H)$^-$; 1H NMR (300 MHz, CHLOROFORM-D) δ ppm 2.66 (m, 2 H), 3.52 (t, J=5.6 Hz, 2 H), 4.08 (q, J=2.8 Hz, 2 H), 6.79 (m, 1 H), 7.01 (dd, J=7.8, 4.7 Hz, 1 H), 7.53 (s, 1 H), 7.64 (d, J=2.4 Hz, 4 H), 7.90 (dd, J=7.8, 1.7 Hz, 1 H), 8.43 (d, J=3.4 Hz, 1 H).

Example 62

3'-Chloro-3,6-dihydro-2H-[1,2']bipyridinyl-4-carboxylic acid (4-bromo-3-chloro-phenyl)-amide

The title compound was prepared using the procedure described in Example 49D using 4-bromo-3-chloro-aniline instead of 4-ter-butylaniline. MS (ESI+) m/z 427 (M+H)$^+$, m/z 425 (M−H)$^-$; 1H NMR (300 MHz, DMSO-D6) δ ppm 2.55 (m, 2 H), 3.45 (t, J=5.6 Hz, 2 H), 4.02 (q, J=2.7 Hz, 2 H), 6.83 (m, 1 H), 7.01 (dd, J=7.8, 4.7 Hz, 1 H), 7.60 (m, 1 H), 7.70 (m, 1 H), 7.83 (dd, J=7.8, 1.7 Hz, 1 H), 8.07 (d, J=2.4 Hz, 1 H), 8.22 (dd, J=4.7, 1.7 Hz, 1 H), 10.00 (s, 1 H).

Example 63

3'-Trifluoromethyl-3,6-dihydro-2H-[1,2']bipyridinyl-4-carboxylic acid (4-azepan-1-yl-phenyl)-amide The title compound was prepared using the procedure described in Example 49D using 4-azepan-1-yl-aniline instead of 4-ter-butylaniline. MS (ESI+) m/z 445 (M+H)$^+$, m/z 443 (M−H)$^-$; 1H NMR (300 MHz, CHLOROFORM-D) δ ppm 1.54 (m, 4 H), 1.78 (s, 4 H), 2.65 (m, 2 H), 3.44 (s, 4 H), 3.52 (t, J=5.4 Hz, 2 H), 4.05 (d, J=2.4 Hz, 2 H), 6.65 (d, J=5.8 Hz, 2 H), 6.73 (s, 1 H), 6.97 (dd, J=7.8, 4.7 Hz, 1 H), 7.22 (m, 1 H), 7.35 (d, J=8.5 Hz, 2 H), 7.87 (dd, J=7.8, 2.0 Hz, 1 H), 8.41 (dd, J=4.7, 1.7 Hz, 1 H).

Example 64

3'-Chloro-3,6-dihydro-2H-[1,2']bipyridinyl-4-carboxylic acid (4-bromo-3-trifluoromethyl-phenyl)-amide The title compound was prepared using the procedure described in Example 49D using 4-bromo-3-trifluoromethyl-aniline instead of 4-ter-butylaniline. MS (ESI+) m/z 461 (M+H)$^+$, m/z 459 (M−H)$^-$; 1H NMR (300 MHz, DMSO-D6) δ ppm 2.56 (br. s, 2 H), 3.46 (t, J=5.6 Hz, 2 H), 4.03 (q, J=2.7 Hz, 2 H), 6.86 (m, 1 H), 7.01 (dd, J=7.8, 4.7 Hz, 1 H), 7.82 (d, J=1.7 Hz, 1 H), 7.84 (m, 1 H), 7.95 (dd, J=8.8, 2.4 Hz, 1 H), 8.23 (dd, J=4.7, 1.7 Hz, 1 H), 8.28 (d, J=2.4 Hz, 1 H), 10.14 (s, 1 H).

Example 65

3'-Chloro-3,6-dihydro-2H-[1,2']bipyridinyl-4-carboxylic acid (4-chloro-3-fluoro-phenyl)-amide The title compound was prepared using the procedure described in Example 49D using 4-chloro-3-fluoro-aniline instead of 4-ter-butylaniline. MS (ESI+) m/z 365 (M+H)$^+$, m/z 363 (M−H)$^-$; 1H NMR (300 MHz, DMSO-D6) δ ppm 2.55 (br. s, 2 H), 4.02 (q, J=2.9 Hz, 2 H), 6.82 (m, 1 H), 7.01 (dd, J=7.8, 4.7 Hz, 1 H), 7.52 (m, 2 H), 7.84 (m, 2 H), 8.22 (dd, J=4.7, 1.7 Hz, 1 H), 10.05 (s, 1 H).

Example 66

3'-Chloro-3,6-dihydro-2H-[1,2']bipyridinyl-4-carboxylic acid (3,4-dichloro-phenyl)-amide The title compound was prepared using the procedure described in Example 49D using 3,4-dichloro-aniline instead of 4-ter-butylaniline. MS (ESI+) m/z 381 (M+H)$^+$; 1H NMR (300 MHz, DMSO-D6) δ ppm 2.55 (m, 2 H), 3.45 (t, J=5.4 Hz, 2 H), 4.02 (q, J=2.8 Hz, 2 H), 6.82 (m, 1 H), 7.01 (dd, J=7.8, 4.7 Hz, 1 H), 7.57 (d, J=8.8 Hz, 1 H), 7.67 (dd, J=8.8, 2.4 Hz, 1 H), 7.83 (dd, J=7.8, 1.7 Hz, 1 H), 8.07 (d, J=2.4 Hz, 1 H), 8.22 (dd, J=4.7, 1.7 Hz, 1 H), 10.01 (s, 1 H).

Example 67

3'-Chloro-3,6-dihydro-2H-[1,2']bipyridinyl-4-carboxylic acid (4-chloro-3-methyl-phenyl)-amide The title compound was prepared using the procedure described in Example 49D using 4-chloro-3-methyl-aniline instead of 4-ter-butylaniline. MS (ESI+) m/z 361 (M+H)$^+$, m/z 360 (M−H)$^-$; 1H NMR (300 MHz, DMSO-D6) δ ppm 2.30 (s, 3 H), 2.55 (m, 2 H), 3.46 (t, J=5.4 Hz, 2 H), 4.01 (q, J=2.7 Hz, 2 H), 6.79 (m, 1 H), 7.00 (dd, J=7.8, 4.7 Hz, 1 H), 7.33 (d, J=8.8 Hz, 1 H), 7.55 (dd, J=8.6, 2.5 Hz, 1 H), 7.70 (d, J=2.7 Hz, 1 H), 7.83 (dd, J=7.8, 1.4 Hz, 1 H), 8.22 (dd, J=4.7, 1.7 Hz, 1 H), 9.78 (s, 1 H).

Example 68

3'-Chloro-3,6-dihydro-2H-[1,2']bipyridinyl-4-carboxylic acid (4-chloro-3-trifluoromethyl-phenyl)-amide The title compound was prepared using the procedure described in Example 49D using 4-chloro-3-trifluoromethyl-aniline instead of 4-ter-butylaniline. MS (ESI+) m/z 415 (M+H)$^+$, m/z 413 (M−H)$^-$; 1H NMR (300 MHz, DMSO-D6) δ ppm 2.56 (m, 2 H), 3.46 (t, J=5.6 Hz, 2 H), 4.03 (q, J=2.7 Hz, 2 H), 6.86 (m, 1 H), 7.01 (dd, J=7.8, 4.7 Hz, 1 H), 7.67 (d, J=8.8 Hz, 1 H), 7.83 (dd, J=7.8, 1.7 Hz, 1 H), 8.02 (dd, J=8.8, 2.7 Hz, 1 H), 8.22 (dd, J=4.6, 1.5 Hz, 1H), 8.28 (d, J=2.7 Hz, 1 H), 10.14 (s, 1 H).

Example 69

3'-Chloro-3,6-dihydro-2H-[1,2']bipyridinyl-4-carboxylic acid (4-difluoromethyoxy-phenyl)-amide The title compound was prepared using the procedure described in Example 49D using 4-difluoromethyoxy-aniline instead of 4-ter-butylaniline. MS (ESI+) m/z 379 (M+H)$^+$, m/z 377 (M−H)$^-$; 1H NMR (300 MHz, DMSO-D6) δ ppm 2.56 (m, 2 H), 3.45 (t, J=5.8 Hz, 2 H), 4.02 (q, J=2.7 Hz, 2 H), 6.79 (m, 1 H), 7.00 (dd, J=7.8, 4.7 Hz, 1 H), 7.13 (d, J=8.1 Hz, 2 H), 7.15 (t, J=45 Hz, 1 H), 7.72 (d, J=9.2 Hz, 2 H), 7.83 (dd, J=7.8, 1.7 Hz, 1 H), 8.22 (dd, J=4.7, 1.4 Hz, 1 H), 9.82 (s, 1 H).

Example 70

3'-Chloro-3,6-dihydro-2H-[1,2']bipyridinyl-4-carboxylic acid [4-(1,1,2,2-tetrafluoro-ethoxy)-phenyl]-amide The title compound was prepared using the procedure described in Example 49D using 4-(1,1,2,2-tetrafluoro-ethoxy)-aniline instead of 4-ter-butylaniline. MS (ESI+) m/z 429 (M+H)$^+$, m/z 427 (M−H)$^-$; 1H NMR (300 MHz, DMSO-D6) δ ppm 2.56 (m, 2 H), 3.46 (t, J=5.6 Hz, 2 H), 4.02 (q, J=2.7 Hz, 2 H), 6.79 (m, 1 H), 6.80 (tt, J=52, 3.1 Hz, 1 H), 7.01 (dd, J=7.6, 4.6 Hz, 1 H), 7.23 (d, J=9.2 Hz, 2 H), 7.78 (d, J=9.2 Hz, 2 H), 7.83 (dd, J=7.8, 1.7 Hz, 1 H), 8.23 (dd, J=4.7, 1.7 Hz, 1 H), 9.90 (s, 1 H).

Example 71

3'-Chloro-3,6-dihydro-2H-[1,2']bipyridinyl-4-carboxylic acid (3-chloro-4-methyl-phenyl)-amide The title compound was prepared using the procedure described in Example 49D using 3-chloro-4-methyl-aniline instead of 4-ter-butylaniline. MS (ESI+) m/z 361 (M+H)$^+$, m/z 360 (M−H)$^-$; 1H NMR (300 MHz, DMSO-D6) δ ppm 2.28 (s, 3 H), 2.55 (m, 2 H), 3.45 (t, J=5.6 Hz, 2 H), 4.01 (q, J=2.8 Hz, 2 H), 6.79 (m, 1 H), 7.00 (dd, J=7.8, 4.7 Hz, 1 H), 7.27 (d, J=8.5 Hz, 1 H), 7.52 (dd, J=8.3, 2.2 Hz, 1 H), 7.83

(dd, J=7.5, 1.4 Hz, 1 H), 7.86 (d, J=2.0 Hz, 1 H), 8.22 (dd, J=4.7, 1.7 Hz, 1 H), 9.81 (s, 1 H).

Example 72

3'-Chloro-3,6-dihydro-2H-[1,2']bipyridinyl-4-carboxylic acid (3-bromo-4-methyl-phenyl)-amide The title compound was prepared using the procedure described in Example 49D using 3-bromo-4-methyl-aniline instead of 4-ter-butylaniline. MS (ESI+) m/z 407 (M+H)$^+$, m/z 405 (M–H)$^-$; 1H NMR (300 MHz, DMSO-D6) δ ppm 2.29 (s, 3 H), 2.55 (m, 2 H), 3.45 (t, J=5.4 Hz, 2 H), 4.01 (q, J=2.7 Hz, 2 H), 6.79 (m, 1 H), 7.00 (dd, J=7.8, 4.7 Hz, 1 H), 7.28 (d, J=9.2 Hz, 1 H), 7.58 (dd, J=8.3, 2.2 Hz, 1 H), 7.82 (dd, J=7.8, 1.4 Hz, 1 H), 8.03 (d, J=2.0 Hz, 1 H), 8.22 (dd, J=4.7, 1.4 Hz, 1 H), 9.80 (s, 1 H).

Example 73

3'-Chloro-3,6-dihydro-2H-[1,2']bipyridinyl-4-carboxylic acid (4-methyl-3-trifluoromethyl-phenyl)-amide The title compound was prepared using the procedure described in Example 49D using 3-trifluoromethyl-4-methyl-aniline instead of 4-ter-butylaniline. MS (ESI+) m/z 396 (M+H)$^+$, m/z 394 (M–H)$^-$; 1H NMR (300 MHz, DMSO-D6) δ ppm 2.39 (d, J=1.7 Hz, 3 H), 2.56 (m, 2 H), 3.46 (t, J=5.6 Hz, 2 H), 4.02 (q, J=2.7 Hz, 2 H), 6.83 (m, 1 H), 7.00 (dd, J=7.8, 4.7 Hz, 1 H), 7.37 (d, J=8.5 Hz, 1 H), 7.84 (m, 2 H), 8.09 (d, J=2.4 Hz, 1 H), 8.22 (dd, J=4.6, 1.5 Hz, 1 H), 9.94 (s, 1 H).

Example 74

3'-Chloro-3,6-dihydro-2H-[1,2']bipyridinyl-4-carboxylic acid (5-fluoro-pyridin-2-yl)-amide The title compound was prepared using the procedure described in Example 49D using 5-fluoro-pyridin-2-ylamine instead of 4-ter-butylaniline. MS (ESI+) m/z 330 (M–H)$^-$ (20%) m/z 212 (M-120)$^-$ (100%); 1 H NMR (300 MHz, DMSO-D6) δ ppm 2.57 (m, 2 H), 4.00 (q, J=2.8 Hz, 3 H), 6.92 (m, 1 H), 7.00 (dd, J=7.8, 4.7 Hz, 1 H), 7.75 (m, 1 H), 7.82 (dd, J=7.8, 1.7 Hz, 1 H), 8.11 (dd, J=9.3, 4.2 Hz, 1 H), 8.22 (dd, J=4.7, 1.7 Hz, 1 H), 8.35 (d, J=3.4 Hz, 1 H), 10.30 (s, 1 H).

Example 75

3'-Chloro-3,6-dihydro-2H-[1,2']bipyridinyl-4-carboxylic acid (5-chloro-pyridin-2-yl)-amide The title compound was prepared using the procedure described in Example 49D using 5-chloro-pyridin-2-ylamine instead of 4-ter-butylaniline. MS (ESI+) m/z 348 (M+H)$^+$, m/z 346 (M–H)$^-$ (80%) m/z 212 (M-137)$^-$ (100%); 1H NMR (300 MHz, DMSO-D6) δ ppm 2.57 (m, 2 H), 3.44 (t, J=5.4 Hz, 2 H), 4.00 (q, J=2.9 Hz, 2 H), 6.94 (m, 1 H), 7.00 (dd, J=7.8, 4.7 Hz, 1H), 7.82 (dd, J=7.8, 1.7 Hz, 1 H), 7.91 (dd, J=9.0, 2.9 Hz, 1 H), 8.11 (d, J=0.7 Hz, 1 H), 8.22 (dd, J=4.7, 1.4 Hz, 1 H), 8.40 (dd, J=2.5, 0.8 Hz, 1 H), 10.39 (s, 1 H).

Example 76

3'-Chloro-3,6-dihydro-2H-[1,2']bipyridinyl-4-carboxylic acid (5-bromo-pyridin-2-yl)-amide The title compound was prepared using the procedure described in Example 49D using 5-bromo-pyridin-2-ylamine instead of 4-ter-butylaniline. MS (ESI+) m/z 395 (M+H)$^+$ (60%), m/z 392 (M–H)$^+$ (100%), m/z 392 (M–H)$^-$; 1H NMR (300 MHz, DMSO-D6) δ ppm 2.56 (m, 2 H), 3.44 (t, J=5.6 Hz, 2 H), 4.00 (q, J=2.7 Hz, 2 H), 6.95 (m, 1 H), 7.00 (dd, J=7.8, 4.7 Hz, 1 H), 7.82 (dd, J=7.8, 1.7 Hz, 1 H), 8.04 (m, 2 H), 8.22 (dd, J=4.7, 1.7 Hz, 1 H), 8.47 (dd, J=2.4, 0.7 Hz, 1 H), 10.39 (s, 1H).

Example 77

3'-Chloro-3,6-dihydro-2H-[1,2']bipyridinyl-4-carboxylic acid (5-iodo-pyridin-2-yl)-amide The title compound was prepared using the procedure described in Example 49D using 5-iodo-pyridin-2-ylamine instead of 4-ter-butylaniline. MS (ESI+) m/z 441 (M+H)$^+$ (95%), m/z 436 (M-4)$^+$ (100%), m/z 438 (M–H)$^-$ (25%), m/z 211 (M-229)$^-$ (100%); 1H NMR (300 MHz, DMSO-D6) δ ppm 2.56 (m, 2 H), 3.99 (q, J=2.7 Hz, 2 H), 6.94 (m, 1 H), 7.00 (dd, J=7.6, 4.6 Hz, 1 H), 7.82 (dd, J=7.8, 1.7 Hz, 1 H), 7.97 (dd, J=8.8, 1.0 Hz, 1 H), 8.12 (dd, J=8.6, 2.2 Hz, 1 H), 8.21 (dd, J=4.6, 1.5 Hz, 1 H), 8.56 (dd, J=2.4, 0.7 Hz, 1 H), 10.33 (s, 1 H).

Example 78

3'-Chloro-3,6-dihydro-2H-[1,2']bipyridinyl-4-carboxylic acid (4-trifluoromethylsulfanyl-phenyl)-amide The title compound was prepared using the procedure described in Example 49D using 5-fluoro-pyridin-2-ylamine instead of 4-ter-butylaniline. MS (ESI+) m/z 413 (M+H)$^+$, m/z 411 (M–H)$^-$; 1H NMR (400 MHz, DMSO-D6) δ ppm 2.57 (m, 2 H), 3.46 (t, J=5.5 Hz, 2 H), 4.03 (q, J=2.9 Hz, 2 H), 6.84 (m, 1 H), 7.00 (dd, J=7.7, 4.6 Hz, 1 H), 7.66 (d, J=8.6 Hz, 2 H), 7.82 (dd, J=7.8, 1.7 Hz, 1 H), 7.87 (m, 2 H), 8.23 (dd, J=4.8, 1.7 Hz, 1 H), 10.04 (s, 1 H).

Example 79

3'-Chloro-3,6-dihydro-2H-[1,2']bipyridinyl-4-carboxylic acid (3-fluoro-4-trifluoromethyl-phenyl)-amide The title compound was prepared using the procedure described in Example 49D using 3-fluoro-4-trifluoromethyl-aniline instead of 4-ter-butylaniline. MS (DCI+) m/z 400 (M+H)$^+$; 1H NMR (300 MHz, DMSO-D6) δ ppm 2.57 (m, 2 H), 3.46 (t, J=5.4 Hz, 2 H), 4.04 (q, J=3.1 Hz, 2 H), 6.88 (m, 1 H), 7.01 (dd, J=7.6, 4.6 Hz, 1 H), 7.70 (m, 2 H), 7.83 (dd, J=7.8, 1.7 Hz, 1 H), 7.91 (d, J=13.6 Hz, 1 H), 8.23 (dd, J=4.7, 1.4 Hz, 1 H), 10.28 (s, 1 H).

Example 80

3'-Chloro-3,6-dihydro-2H-[1,2']bipyridinyl-4-carboxylic acid (4-bromo-2-chloro-phenyl)-amide The title compound was prepared using the procedure described in Example 49D using 2-chloro-4-bromo-aniline instead of 4-ter-butylaniline. MS (ESI+) m/z 427 (M+H)$^+$ (80%), m/z 459 (M+32)$^+$ (100%), m/z 426 (M−H)$^−$ (90%), m/z 305 (M-122)$^−$ (100%); 1H NMR (400 MHz, DMSO-D6) δ ppm 2.56 (m, 2 H), 3.46 (t, J=5.5 Hz, 2 H), 4.03 (q, J=2.8 Hz, 2 H), 6.89 (m, 1 H), 7.00 (dd, J=7.8, 4.8 Hz, 1 H), 7.55 (m, 2 H), 7.79 (d, J=1.8 Hz, 1 H), 7.82 (dd, J=7.7, 1.8 Hz, 1 H), 8.22 (dd, J=4.8, 1.4 Hz, 1 H), 9.45 (s, 1 H).

Example 81

3'-Chloro-3,6-dihydro-2H-[1,2']bipyridinyl-4-carboxylic acid (4-bromo-2-fluoro-phenyl)-amide The title compound was prepared using the procedure described in Example 49D using 2-fluoro-4-bromo-aniline instead of 4-ter-butylaniline. MS (ESI+) m/z 410 (M+H)$^+$ (80%), m/z 407 (M-3)$^+$ (100%), m/z 409 (M−H)$^−$; 1H NMR (400 MHz, DMSO-D6) δ ppm 2.55 (m, 2 H), 3.46 (t, J=5.5 Hz, 2 H), 4.02 (q, J=3.0 Hz, 2 H), 6.86 (m, 1 H), 7.00 (dd, J=7.8, 4.8 Hz, 1 H), 7.40 (dd, J=8.6, 1.2 Hz, 1 H), 7.54 (t, J=8.4 Hz, 1 H), 7.59 (dd, J=10.1, 2.1 Hz, 1 H), 7.82 (dd, J=7.8, 1.7 Hz, 1 H), 8.22 (dd, J=4.6, 1.5 Hz, 1 H), 9.60 (s, 1 H).

Example 82

3'-Chloro-3,6-dihydro-2H-[1,2']bipyridinyl-4-carboxylic acid (4-bromo-2-methyl-phenyl)-amide The title compound was prepared using the procedure described in Example 49D using 2-methyl-4-bromo-aniline instead of 4-ter-butylaniline. MS (ESI+) m/z 407 (M+H)$^+$, m/z 405 (M−H)$^−$; 1H NMR (400 MHz, DMSO-D6) δ ppm 2.19 (s, 3 H), 2.57 (m, 2 H), 3.46 (t, J=5.5 Hz, 2 H), 4.02 (q, J=2.9 Hz, 2 H), 6.83 (m, 1 H), 7.00 (dd, J=7.8, 4.8 Hz, 1 H), 7.27 (d, J=8.6 Hz, 1 H), 7.36 (m, 1 H), 7.46 (d, J=1.5 Hz, 1 H), 7.82 (dd, J=7.8, 1.7 Hz, 1 H), 8.22 (dd, J=4.8, 1.7 Hz, 1 H), 9.30 (s, 1 H).

Example 83

3'-Chloro-3,6-dihydro-2H-[1,2']bipyridinyl-4-carboxylic acid (2-fluoro-4-iodo-phenyl)-amide The title compound was prepared using the procedure described in Example 49D using 2-fluoro-4-iodo-aniline instead of 4-ter-butylaniline. MS (ESI+) m/z 457 (M+H)$^+$ (80%), m/z 453 (M-4)$^+$ (100%), m/z 455 (M−H)$^−$; 1H NMR (400 MHz, DMSO-D6) δ ppm 2.54 (m, 2 H), 3.46 (t, J=5.5 Hz, 2 H), 4.01 (q, J=2.8 Hz, 2 H), 6.85 (m, 1 H), 7.00 (dd, J=7.7, 4.6 Hz, 1 H), 7.38 (t, J=8.3 Hz, 1 H), 7.54 (dd, J=8.3, 1.2 Hz, 1 H), 7.68 (dd, J=10.0, 2.0 Hz, 1 H), 7.82 (dd, J=8.0, 1.5 Hz, 1 H), 8.22 (dd, J=4.6, 1.5 Hz, 1 H), 9.57 (s, 1 H).

Example 84

3'-Chloro-3,6-dihydro-2H-[1,2']bipyridinyl-4-carboxylic acid (4-chloro-2-trifluoromethyl-phenyl)-amide The title compound was prepared using the procedure described in Example 49D using 2-trifluoromethyl-4-chloro-aniline instead of 4-ter-butylaniline. MS (ESI+) m/z 417 (M+H)$^+$ (75%), m/z 230 (M-186)$^+$ (100%), m/z 414 (M−H)$^−$; 1H NMR (400 MHz, DMSO-D6) δ ppm 2.54 (m, 2 H), 3.46 (t, J=5.4 Hz, 2 H), 4.02 (q, J=2.8 Hz, 2 H), 6.83 (m, 1 H), 7.00 (dd, J=7.8, 4.8 Hz, 1 H), 7.52 (d, J=8.3 Hz, 1 H), 7.78 (dd, J=8.6, 2.5 Hz, 1 H), 7.82 (m, 2 H), 8.22 (dd, J=4.8, 1.7 Hz, 1 H), 9.57 (s, 1 H).

Example 85

3'-Chloro-3,6-dihydro-2H-[1,2']bipyridinyl-4-carboxylic acid (4-chloro-2-fluoro-phenyl)-amide The title compound was prepared using the procedure described in Example 49D using 2-fluoro-4-chloro-aniline instead of 4-ter-butylaniline. MS (ESI+) m/z 366 (M+H)$^+$, m/z 365 (M−H)$^−$ (80%), m/z 363 (M-3)$^−$ (100%); 1H NMR (400 MHz, DMSO-D6) δ ppm 2.55 (m, 2 H), 3.46 (t, J=5.5 Hz, 2 H), 4.02 (q, J=2.8 Hz, 2 H), 6.86 (m, 1 H), 7.00 (dd, J=7.7, 4.6 Hz, 1H), 7.28 (m, 1 H), 7.49 (dd, J=10.4, 2.5 Hz, 1 H), 7.58 (t, J=8.4 Hz, 1 H), 7.82 (dd, J=7.8, 1.7 Hz, 1 H), 8.22 (d, J=1.5 Hz, 1 H), 9.60 (s, 1 H).

Example 86

3'-Chloro-3,6-dihydro-2H-[1,2']bipyridinyl-4-carboxylic acid (2,2-difluoro-benzo[1,3]dioxol-5-yl)-amide The title compound was prepared using the procedure described in Example 49D using 2,2-difluoro-benzo[1,3]dioxol-5-yl amine instead of 4-ter-butylaniline. MS (ESI+) m/z 216 (M-177)$^+$ (100%), m/z 391 (M−H)$^−$; 1H NMR (300 MHz, DMSO-D6) δ ppm 2.56 (m, 2 H), 3.46 (t, J=5.6 Hz, 2 H), 4.02 (q, J=2.7 Hz, 2 H), 6.80 (m, 1 H), 7.00 (dd, J=7.8, 4.7 Hz, 1 H), 7.35 (d, J=8.8 Hz, 1 H), 7.42 (dd, J=8.8, 2.0 Hz, 1 H), 7.83 (m, 2 H), 8.22 (dd, J=4.7, 1.7 Hz, 1 H), 9.94 (s, 1 H).

Example 87

3'-Chloro-3,6-dihydro-2H-[1,2']bipyridinyl-4-carboxylic acid (3,4-dimethyl-phenyl)-amide The title compound was prepared using the procedure described in Example 49D using 3,4-dimethyl-aniline instead of 4-ter-butylaniline. MS (ESI+) m/z 342 (M+H)$^+$; 1H NMR (300 MHz, DMSO-D6) δ ppm 2.17 (s, 3 H), 2.19 (s, 3 H), 2.55 (m, 2 H), 3.46 (t, J=5.4 Hz, 2 H), 4.00 (q, J=2.7 Hz, 2 H), 6.75 (m, 1 H), 7.00 (dd, J=7.8, 4.7 Hz, 1 H), 7.04 (m, 1 H), 7.39 (dd, J=8.0, 2.2 Hz, 1 H), 7.46 (d, J=2.0 Hz, 1 H), 7.82 (dd, J=7.8, 1.7 Hz, 1 H), 8.22 (dd, J=4.6, 1.5 Hz, 1 H), 9.56 (s, 1 H).

Example 88

3'-Chloro-3,6-dihydro-2H-[1,2']bipyridinyl-4-carboxylic acid (6-trifluoromethyl-pyridin-3-yl)-amide The title compound was prepared using the procedure described in Example 49D using 6-trifluoromethyl-pyridin-3-ylamine instead of 4-ter-butylaniline. MS (ESI+) m/z 383 (M+H)$^+$, m/z 380 (M–H)$^-$; 1H NMR (300 MHz, DMSO-D6) δ ppm 2.58 (m, 2 H), 3.47 (t, J=5.6 Hz, 2 H), 4.05 (q, J=2.8 Hz, 2 H), 6.92 (m, 1 H), 7.01 (dd, J=7.8, 4.7 Hz, 1 H), 7.84 (dd, J=7.8, 1.7 Hz, 1 H), 7.88 (d, J=8.8 Hz, 1 H), 8.23 (dd, J=4.7, 1.7 Hz, 1 H), 8.40 (dd, J=8.3, 2.2 Hz, 1 H), 9.01 (d, J=2.4 Hz, 1 H), 10.32 (s, 1 H).

Example 89

3'-Chloro-3,6-dihydro-2H-[1,2']bipyridinyl-4-carboxylic acid (4-tert-butyl-2-fluoro-phenyl)-amide The title compound was prepared using the procedure described in Example 49D using 4-tert-butyl-2-fluoro-aniline instead of 4-ter-butylaniline. MS (ESI+) m/z 388 (M+H)$^+$, m/z 386 (M–H)$^-$; 1H NMR (500 MHz, DMSO-D6) δ ppm 1.28 (s, 9 H), 2.55 (m, 2 H), 3.46 (t, J=5.5 Hz, 2 H), 4.02 (q, J=3.1 Hz, 2 H), 6.84 (m, 1 H), 7.01 (dd, J=7.8, 4.7 Hz, 1 H), 7.19 (dd, J=8.4, 2.0 Hz, 1 H), 7.24 (dd, J=12.8, 2.1 Hz, 1 H), 7.42 (t, J=8.4 Hz, 1 H), 7.84 (dd, J=7.6, 1.5 Hz, 1 H), 8.22 (dd, J=4.6, 1.5 Hz, 1 H), 9.47 (s, 1 H).

Example 90

3'-Chloro-3,6-dihydro-2H-[1,2']bipyridinyl-4-carboxylic acid (6-chloro-pyridin-3-yl)-amide The title compound was prepared using the procedure described in Example 49D using 6-chloro-pyridin-3-ylamine instead of 4-ter-butylaniline. MS (ESI+) m/z 348 (M+H)$^+$, m/z 346 (M–H)$^-$; 1H NMR (300 MHz, DMSO-D6) δ ppm 2.55 (m, 2 H), 3.46 (t, J=5.6 Hz, 2 H), 4.03 (q, J=2.7 Hz, 2 H), 6.86 (m, 1 H), 7.01 (dd, J=7.8, 4.7 Hz, 1 H), 7.48 (d, J=8.5 Hz, 1 H), 7.83 (dd, J=7.8, 1.4 Hz, 1 H), 8.17 (dd, J=8.6, 2.9 Hz, 1 H), 8.23 (dd, J=4.7, 1.7 Hz, 1 H), 8.71 (d, J=2.4 Hz, 1 H), 10.09 (s, 1 H).

Example 91

3'-Chloro-3,6-dihydro-2H-[1,2']bipyridinyl-4-carboxylic acid (4-tert-butyl-3-fluoro-phenyl)-amide The title compound was prepared using the procedure described in Example 49D using 4-tert-butyl-3-fluoro-aniline instead of 4-ter-butylaniline. MS (ESI+) m/z 388 (M+H)$^+$, m/z 386 (M–H)$^-$; 1H NMR (300 MHz, DMSO-D6) δ ppm 1.32 (s, 9 H), 2.56 (m, 2 H), 3.45 (t, J=5.6 Hz, 2 H), 4.02 (q, J=2.7 Hz, 2 H), 6.80 (m, 1 H), 7.00 (dd, J=7.8, 4.7 Hz, 1 H), 7.25 (t, J=9.5 Hz, 1 H), 7.39 (dd, J=8.8, 2.4 Hz, 1 H), 7.58 (dd, J=15.4, 2.2 Hz, 1 H), 7.83 (dd, J=7.6, 1.5 Hz, 1 H), 8.22 (dd, J=4.7, 1.4 Hz, 1 H), 9.85 (s, 1 H).

Example 92

3'-Trifluoromethyl-3,6-dihydro-2H-[1,2']bipyridinyl-4-carboxylic acid [4-(8-aza-bicyclo[3.2.1]oct-8-yl)-phenyl]-amide

Example 92A

8-Aza-bicyclo[3.2.1]octane

To a solution of 8-Methyl-8-aza-bicyclo[3.2.1]octane (19.5 g, 0.156 mol) in DCE (500 mL) at 0° C. was added 1-chloroethyl chloroformate (19.5 mL, 0.179 mol) over 5 min. The mixture was heated to reflux for 4 h, concentrated, and filtered through silica (50% Et$_2$O/Hex). The residue was then refluxed in MeOH (150 mL) for 45 min and concentrated under reduced pressure to provide 8-Aza-bicyclo[3.2.1]octane as a light yellow solid (19.2 g, 0.130 mol, 83%)%): $^1$H NMR (300 MHz, CDCl$_3$) δ 9.47 (brs, 2H), 4.03 (m, 2H), 2.18-2.33 (m, 4H), 1.81-1.89 (m, 2H), 1.55-1.77 (m, 4H).

Example 92B

4-(8-Aza-bicyclo[3.2.1]oct-8-yl)-phenylamine

A mixture of 4-fluoro-nitrobenzene (0.72 mL, 6.8 mmol), 8-Aza-bicyclo[3.2.1]octane (1.01 g, 6.82 mmol), and K$_2$CO$_3$ (1.87 g, 13.5 g) in DMSO (7 mL) was heated to 110° C. and stirred for 3 hour. The mixture was diluted with Et$_2$O (60 mL) and washed with water (40 mL) and brine (30 mL). The organic layer was dried (Na$_2$SO$_4$), concentrated, and triturated with hexane to provide 1.27 g of a yellow solid. A mixture of the solid, HCO$_2$NH$_4$ (1.45 g, 23.0 mmol), and 10% Pd/C (cat) in MeOH (20 mL) was stirred overnight, filtered, and concentrated. The residue was diluted with sat. aq. NaHCO$_3$ (20 mL) and extracted with CH$_2$Cl$_2$ (3×10 mL). The organic layer was dried (Na$_2$SO$_4$) and concentrated under reduced pressure to provide 4-(8-Aza-bicyclo[3.2.1]oct-8-yl)-phenylamine as a dark solid.

$^1$H NMR (300 MHz, CDCl$_3$) δ 6.66 (s, 4H), 4.07 (brs, 2H), 3.14 (brs, 2H), 1.74-2.09 (m, 7H), 1.44 (m, 1H), 1.22 (m, 2H).

Example 92C

3'-Trifluoromethyl-3,6-dihydro-2H-[1,2']bipyridinyl-4-carboxylic acid [4-(8-aza-bicyclo[3.2.1]oct-8-yl)-phenyl]-amide The title compound was prepared using the procedure described in Example 49D using 4-(8-Aza-bicyclo[3.2.1]oct-8-yl)-phenylamine instead of 4-ter-butylaniline. MS (ESI+) m/z 457 (M+H)$^+$; 1H NMR (400 MHz, Methanol-D4) δ ppm 1.29 (m, 2 H), 1.44 (m, 1H), 1.88 (m, 5 H), 2.06 (m, 2 H), 2.61 (m, 2 H), 3.46 (t, J=5.5 Hz, 2 H), 4.01 (q, J=2.9 Hz, 2 H), 4.17 (s, 2 H), 6.72 (m, 1 H), 6.80 (d, J=8.9 Hz, 2 H), 7.11 (dd, J=7.8, 4.8 Hz, 1 H), 7.39 (d, J=8.9 Hz, 2 H), 8.00 (dd, J=7.8, 1.7 Hz, 1 H), 8.45 (d, J=4.9 Hz, 1 H).

Example 93

3'-Trifluoromethyl-3,6-dihydro-2H-[1,2']bipyridinyl-4-carboxylic acid [4-(8-aza-bicyclo[3.2.1]oct-8-yl)-3-fluoro-phenyl]amide The title compound was prepared using the procedure described in Example 49D using 4-(8-aza-bicyclo[3.2.1]oct-8-yl)-3-fluoro-phenylamine instead of 4-ter-butylaniline. MS (ESI+) m/z 475 (M+H)$^+$, m/z 473 (M–H)$^-$; 1H NMR (400 MHz, Methanol-D4) δ ppm 1.44 (m, 3 H), 1.87 (m, 7 H), 2.60 (m, 2 H), 3.45 (t, J=5.5 Hz, 2 H), 4.00 (q, J=3.0 Hz, 2 H), 4.13 (s, 2 H), 6.72 (m, 1 H), 6.89 (t, J=9.8 Hz, 1 H), 7.10 (dd, J=7.8, 4.8 Hz, 1 H), 7.20 (dd, J=8.7, 2.3 Hz, 1 H), 7.42 (dd, J=15.6, 2.5 Hz, 1 H), 7.99 (dd, J=7.8, 1.7 Hz, 1 H), 8.44 (dd, J=4.6, 1.2 Hz, 1 H).

Example 94

3'-Trifluoromethyl-3,6-dihydro-2H-[1,2']bipyridinyl-4-carboxylic acid [4-(8-aza-bicyclo[3.2.1]oct-8-yl)-3,5-difluoro-phenyl]amide The title compound was prepared using the procedure described in Example 49D using 4-(8-aza-bicyclo[3.2.1]oct-8-yl)-3,5-difluoro-phenylamine instead of 4-ter-butylaniline. MS (ESI+) m/z 493 (M+H)$^+$, m/z 491 (M–H)$^-$; 1H NMR (400 MHz, Methanol-D4) δ ppm 1.50 (m, 3 H), 1.86 (m, 7 H), 2.59 (m, 2 H), 3.44 (t, J=5.5 Hz, 2 H), 4.00 (q, J=3.1 Hz, 2 H), 4.03 (s, 2 H), 6.71 (m, 1 H), 7.10 (dd, J=7.8, 4.8 Hz, 1 H), 7.21 (d, J=12.9 Hz, 2 H), 7.99 (dd, J=7.8, 1.7 Hz, 1 H), 8.44 (dd, J=4.6, 1.2 Hz, 1 H).

Example 95

3'-Trifluoromethyl-3,6-dihydro-2H-[1,2']bipyridinyl-4-carboxylic acid (4-chloro-3-fluoro-phenyl)-amide The title compound was prepared using the procedure described in Example 49D using 3-fluoro-4-chloro-aniline instead of 4-ter-butylaniline. MS (ESI+) m/z 400 (M+H)$^+$, m/z 398 (M–H)$^-$; 1H NMR (400 MHz, CHLOROFORM-D) δ ppm 2.64 (m, 2 H), 3.50 (t, J=5.5 Hz, 2 H), 4.05 (q, J=3.1 Hz, 2 H), 6.77 (m, 1 H), 6.99 (dd, J=7.8, 4.8 Hz, 1 H), 7.16 (m, 1 H), 7.31 (t, J=8.9 Hz, 1 H), 7.58 (s, 1 H), 7.66 (dd, J=11.0, 2.5 Hz, 1 H), 7.88 (dd, J=7.7, 1.8 Hz, 1 H), 8.42 (dd, J=4.6, 1.5 Hz, 1 H).

Example 96

3'-Trifluoromethyl-3,6-dihydro-2H-[1,2']bipyridinyl-4-carboxylic acid (4-tert-butyl-3-fluoro-phenyl)-amide The title compound was prepared using the procedure described in Example 49D using 3-fluoro-4-tert-butyl-aniline instead of 4-ter-butylaniline. MS (ESI+) m/z 422 (M+H)$^+$, m/z 420 (M–H)$^-$; 1H NMR (400 MHz, CHLOROFORM-D) δ ppm 1.36 (s, 9 H), 2.65 (m, 2 H), 3.51 (t, J=5.5 Hz, 2 H), 4.05 (q, J=3.1 Hz, 2 H), 6.76 (m, 1 H), 6.98 (dd, J=7.4, 5.2 Hz, 1 H), 7.11 (m, 1 H), 7.23 (t, J=8.7 Hz, 1 H), 7.44 (m, 2 H), 7.88 (dd, J=8.0, 1.8 Hz, 1 H), 8.42 (dd, J=4.6, 1.2 Hz, 1 H).

Example 97

3'-Trifluoromethyl-3,6-dihydro-2H-[1,2']bipyridinyl-4-carboxylic acid [4-(1-hydroxy-1-methyl-ethyl)-phenyl]-amide The title compound was prepared using the procedure described in Example 49D using 4-(1-hydroxy-1-methyl-ethyl)-aniline instead of 4-ter-butylaniline. MS (ESI+) m/z 406 (M+H)$^+$ (80%), m/z 388 (M-17)$^+$ (100%), m/z 404 (M–H)$^-$; 1H NMR (400 MHz, CHLOROFORM-D) δ ppm 1.57 (s, 6 H), 2.65 (m, 2 H), 3.49 (t, J=5.4 Hz, 2 H), 4.03 (q, J=3.0 Hz, 2 H), 5.29 (s, 1 H), 6.75 (m, 1 H), 6.98 (dd, J=7.4, 4.3 Hz, 1 H), 7.44 (m, 2 H), 7.51 (m, 2 H), 7.54 (s, 1 H), 7.88 (dd, J=7.8, 1.7 Hz, 1 H), 8.41 (dd, J=4.8, 1.4 Hz, 1 H).

Example 98

2-Methyl-2-{4-[(3'-trifluoromethyl-3,6-dihydro-2H-[1,2']bipyridinyl-4-carbonyl)-amino]-phenyl}-propionic acid methyl ester The title compound was prepared using the procedure described in Example 49D using 2-(4-Amino-phenyl)-2-methyl-propionic acid methyl ester instead of 4-ter-butylaniline. MS (ESI+) m/z 448 (M+H)$^+$, m/z 446 (M–H)$^-$; 1H NMR (400 MHz, CHLOROFORM-D) δ ppm 1.57 (s, 6 H), 2.65 (m, 2 H), 3.50 (t, J=5.4 Hz, 2 H), 3.64 (s, 3 H), 4.04 (q, J=3.1 Hz, 2 H), 6.75 (m, 1 H), 6.98 (dd, J=7.4, 5.2 Hz, 1 H), 7.30 (m, 2 H), 7.51 (m, 3 H), 7.88 (dd, J=7.7, 1.8 Hz, 1 H), 8.41 (dd, J=4.9, 1.2 Hz, 1 H).

Example 99

1-Pyrimidin-2-yl-1,2,3,6-tetrahydro-pyridine-4-carboxylic acid [4-(8-aza-bicyclo[3.2.1]oct-8-yl)-3-fluoro-phenyl]-amide The title compound was prepared using the procedure described in Example 52B using 4-(8-aza-bicyclo[3.2.1]oct-8-yl)-3-fluoro-phenylamine instead of 4-ter-butylaniline. MS (ESI+) m/z 408 (M+H)$^+$, m/z 406 (M–H)$^-$; 1H NMR (400 MHz, DMSO-D6) δ ppm 1.42 (m, 3 H), 1.76 (m, 5 H), 1.94 (m, 2 H), 2.44 (m, 2 H), 3.91 (t, J=5.7 Hz, 2 H), 4.14 (s, 2 H), 4.35 (q, J=2.8 Hz, 2 H), 6.67 (t, J=4.8 Hz, 1 H), 6.74 (m, 1 H), 6.97 (t, J=9.5 Hz, 1 H), 7.31 (dd, J=8.6, 2.1 Hz, 1 H), 7.57 (dd, J=16.0, 2.5 Hz, 1 H), 8.41 (d, J=4.6 Hz, 2 H), 9.69 (s, 1 H).

Example 100

1-Pyrimidin-2-yl-1,2,3,6-tetrahydro-pyridine-4-carboxylic acid [4-(8-aza-bicyclo[3.2.1]oct-8-yl)-3,5-difluoro-phenyl]-amide The title compound was prepared using the procedure described in Example 52B using 4-(8-aza-bicyclo[3.2.1]oct-8-yl)-3,5-difluoro-phenylamine instead of 4-ter-butylaniline. MS (ESI+) m/z 426 (M+H)$^+$, m/z 424 (M–H)$^-$; 1H NMR (400 MHz, DMSO-D6) δ ppm 1.46 (m, 3 H), 1.74 (m, 5 H), 1.91 (m, 2 H), 2.44 (m, 2 H), 3.91 (t, J=5.7 Hz, 2 H), 3.97 (m, 2 H), 4.35 (q, J=2.8 Hz, 2 H), 6.67 (t, J=4.8 Hz, 1 H), 6.76 (m, 1 H), 7.35 (d, J=13.5 Hz, 2 H), 8.40 (d, J=4.9 Hz, 2 H), 9.78 (s, 1 H).

Example 101

1-Pyrimidin-2-yl-1,2,3,6-tetrahydro-pyridine-4-carboxylic acid (4-azepan-1-yl-phenyl)-amide The title compound was prepared using the procedure described in Example 52B using 4-azapan-1-yl-phenylamine instead of 4-ter-butylaniline. MS (ESI+) m/z 378 (M+H)$^+$, m/z 376 (M−H)$^-$; 1H NMR (400 MHz, DMSO-D6) δ ppm 1.50 (s, 4 H), 1.75 (s, 4 H), 2.45 (m, 2 H), 3.45 (m, 4 H), 3.91 (t, J=5.7 Hz, 2 H), 4.33 (q, J=2.8 Hz, 2 H), 6.67 (t, J=4.6 Hz, 1 H), 6.73 (m, 3 H), 7.46 (d, J=8.9 Hz, 2 H), 8.40 (d, J=4.6 Hz, 2 H), 9.46 (s, 1 H).

Example 102

3'-Chloro-3,6-dihydro-2H-[1,2']bipyridinyl-4-carboxylic acid (2,2,3,3-tetrafluoro-2,3-dihydro-benzo[1,4]dioxin-6-yl)-amide The title compound was prepared using the procedure described in Example 49D using 2,2,3,3-tetrafluoro-2,3-dihydro-benzo[1,4]dioxin-6-ylamine instead of 4-ter-butylaniline. MS (ESI+) m/z 444 (M+H)$^+$ (40%), m/z 330 (M−113)$^+$ (100%), m/z 442 (M−H)$^-$; 1H NMR (400 MHz, DMSO-D6) δ ppm 2.56 (m, 2 H), 3.46 (t, J=5.5 Hz, 2 H), 4.03 (q, J=2.9 Hz, 2 H), 6.82 (m, 1 H), 7.00 (dd, J=7.7, 4.6 Hz, 1 H), 7.43 (m, 1 H), 7.57 (dd, J=9.2, 2.5 Hz, 1 H), 7.82 (dd, J=7.7, 1.5 Hz, 1 H), 7.87 (d, J=2.5 Hz, 1 H), 8.22 (dd, J=4.8, 1.7 Hz, 1 H), 10.03 (s, 1 H).

Example 103

1-Pyrimidin-2-yl-1,2,3,6-tetrahydro-pyridine-4-carboxylic acid (4-tert-butyl-3-fluoro-phenyl)-amide The title compound was prepared using the procedure described in Example 52B using 4-tert-butyl-3-fluoro-aniline instead of 4-ter-butylaniline. MS (ESI+) m/z 355 (M+H)$^+$ (90%), m/z 114 (M−240)$^+$ (100%), m/z 353 (M−H)$^-$; 1H NMR (300 MHz, DMSO-D6) δ ppm 1.32 (s, 9 H), 2.45 (m, 2 H), 3.91 (t, J=5.6 Hz, 2 H), 4.36 (q, J=2.4 Hz, 2 H), 6.67 (t, J=4.7 Hz, 1 H), 6.78 (m, 1 H), 7.25 (m, 2 H), 7.38 (dd, J=8.5, 2.0 Hz, 1 H), 7.57 (dd, J=15.3, 2.0 Hz, 1 H), 8.40 (d, J=4.7 Hz, 1 H), 9.85 (s, 1 H).

Example 104

3'-Trifluoromethyl-3,6-dihydro-2H-[1,2']bipyridinyl-4-carboxylic acid [4-(2-hydroxy-1,1-dimethyl-ethyl)-phenyl]-amide The title compound was prepared using the procedure described in Example 49D using 4-(2-hydroxy-1,1-dimethyl-ethyl)-aniline instead of 4-ter-butylaniline. MS (ESI+) m/z 420 (M+H)$^+$, m/z 418 (M−H)$^-$; 1H NMR (300 MHz, CHLOROFORM-D) δ ppm 1.33 (s, 6 H), 2.04 (s, 1 H), 2.67 (m, 2 H), 3.53 (t, J=5.4 Hz, 2 H), 3.60 (s, 2 H), 4.07 (q, J=2.8 Hz, 2 H), 6.77 (m, 1 H), 6.99 (dd, J=7.8, 4.7 Hz, 1 H), 7.36 (d, J=8.5 Hz, 2 H), 7.41 (s, 1 H), 7.53 (d, J=8.8 Hz, 2 H), 7.89 (dd, J=7.8, 1.7 Hz, 1 H), 8.43 (d, J=4.7 Hz, 1 H).

Example 105

1-Pyrimidin-2-yl-1,2,3,6-tetrahydro-pyridine-4-carboxylic acid (4-trifluoromethyl-phenyl)-amide The title compound was prepared using the procedure described in Example 52B using 4-trifluoromethyl-aniline instead of 4-ter-butylaniline. MS (ESI+) m/z 348 (M+H)$^+$ (40%), m/z 367 (M+19)$^+$ (100%), m/z 346 (M−H)$^-$; 1H NMR (300 MHz, DMSO-D6) δ ppm 2.48 (m, 2 H), 3.93 (t, J=5.8 Hz, 2 H), 4.38 (q, J=2.7 Hz, 2 H), 6.67 (t, J=4.7 Hz, 1 H), 6.84 (m, 1 H), 7.68 (d, J=8.8 Hz, 2 H), 7.91 (d, J=8.5 Hz, 2 H), 8.41 (d, J=4.7 Hz, 2 H), 10.10 (s, 1 H).

Example 106

1-Pyrimidin-2-yl-1,2,3,6-tetrahydro-pyridine-4-carboxylic acid (4-chloro-3-fluoro-phenyl)-amide The title compound was prepared using the procedure described in Example 52B using 4-chloro-3-fluoro-aniline instead of 4-ter-butylaniline. MS (DCI+) m/z 333 (M+H)$^+$; 1H NMR (300 MHz, DMSO-D6) δ ppm 2.47 (m, 2 H), 3.92 (t, J=5.6 Hz, 2 H), 4.37 (q, J=2.9 Hz, 2 H), 6.67 (t, J=4.7 Hz, 1 H), 6.81 (m, 1 H), 7.52 (m, 2 H), 7.85 (m, 1 H), 8.40 (d, J=4.7 Hz, 2 H), 10.05 (s, 1 H).

Example 107

2-Methyl-2-{4-[(1-pyrimidin-2-yl-1,2,3,6-tetrahydro-pyridine-4-carbonyl)-amino]-phenyl}-propionic acid methyl ester The title compound was prepared using the procedure described in Example 52B using 4-propionic acid methyl ester-aniline instead of 4-ter-butylaniline. MS (DCI+) m/z 381 (M+H)$^+$; 1H NMR (300 MHz, DMSO-D6) δ ppm 1.48 (s, 6 H), 2.45 (m, 2 H), 3.58 (s, 3 H), 3.91 (t, J=5.6 Hz, 2 H), 4.35 (q, J=2.9 Hz, 2 H), 6.67 (t, J=4.7 Hz, 1 H), 6.77 (m, 1 H), 7.24 (d, J=8.8 Hz, 2 H), 7.62 (d, J=8.8 Hz, 2 H), 8.40 (d, J=4.7 Hz, 2 H), 9.73 (s, 1 H).

Example 108

3'-Chloro-3,6-dihydro-2H-[1,2']bipyridinyl-4-carboxylic acid [4-(ethyl-isopropyl-amino)-phenyl]-amide hydrochloride The title compound was prepared using the procedure described in Example 49D using 4-(ethyl-isopropyl-amino)-phenylamine instead of 4-ter-butylaniline. MS (ESI+) m/z 399 (M+H)$^+$, m/z 397 (M−H)$^-$; 1H NMR (300 MHz, DMSO-D6) δ ppm 0.99 (t, J=7.1 Hz, 3 H), 1.11 (d, J=6.1 Hz, 3 H), 1.35 (d, J=5.8 Hz, 3 H), 2.57 (s, 2 H), 3.61 (m, 2 H), 3.86 (s, 1 H), 4.03 (q, J=2.7 Hz, 2 H), 6.84 (m, 1 H), 7.01 (dd, J=7.8, 4.7 Hz, 1 H), 7.66 (d, J=8.8 Hz, 2 H), 7.84 (dd, J=7.8, 1.7 Hz, 1 H), 7.90 (d, J=8.8 Hz, 2 H), 8.23 (dd, J=4.7, 1.4 Hz, 1 H), 10.07 (s, 1 H), 11.94 (s, 1 H).

Example 109

3'-Trifluoromethyl-3,6-dihydro-2H-[1,2']bipyridinyl-4-carboxylic acid (4-trifluoromethyl-phenyl)-amide The title compound was prepared using the procedure described in Example 49D using 4-trifluoromethyl-aniline instead of 4-ter-butylaniline. MS (ESI+) m/z 416 (M+H)$^+$, m/z 414 (M−H)⁻; 1H NMR (300 MHz, CHLOROFORM-D) δ ppm 2.68 (m, 2 H), 3.52 (t, J=5.6 Hz, 2 H), 4.08 (q, J=3.1 Hz, 2 H), 6.81 (m, 1 H), 7.00 (dd, J=7.8, 4.7 Hz, 1 H), 7.54 (s, 1 H), 7.60 (d, J=8.5 Hz, 2 H), 7.70 (d, J=8.5 Hz, 2 H), 7.89 (dd, J=7.8, 1.7 Hz, 1 H), 8.43 (dd, J=4.7, 1.4 Hz, 1 H).

Example 110

3'-Trifluoromethyl-3,6-dihydro-2H-[1,2']bipyridinyl-4-carboxylic acid (4-acetyl-phenyl)-amide The title compound was prepared using the procedure described in Example 49D using 4-acetyl-phenylamine instead of 4-ter-butylaniline. MS (ESI+) m/z 390 (M+H)⁺, m/z 388 (M−H)⁻; 1 H NMR (300 MHz, CHLOROFORM-D) δ ppm 2.59 (s, 3 H), 2.68 (m, 2 H), 3.52 (t, J=5.4 Hz, 2 H), 4.08 (q, J=3.1 Hz, 2 H), 6.81 (m, 1 H), 7.00 (dd, J=7.1, 4.7 Hz, 1 H), 7.59 (s, 1 H), 7.68 (d, J=8.8 Hz, 2 H), 7.90 (dd, J=7.8, 1.7 Hz, 1 H), 7.97 (d, J=8.5 Hz, 2 H), 8.43 (dd, J=4.7, 1.4 Hz, 1 H).

Example 111

4-[(3'-Trifluoromethyl-3,6-dihydro-2H-[1,2']bipyridinyl-4-carbonyl)-amino]-benzoic acid methyl ester The title compound was prepared using the procedure described in Example 49D using 4-benzoic acid methyl ester-phenylamine instead of 4-ter-butylaniline. MS (ESI+) m/z 406 (M+H)⁺, m/z 404 (M−H)⁻; 1H NMR (300 MHz, CHLOROFORM-D) δ ppm 2.68 (m, 2 H), 3.52 (t, J=5.4 Hz, 2 H), 3.90 (s, 3 H), 4.08 (q, J=3.1 Hz, 2 H), 6.80 (m, 1 H), 7.00 (dd, J=7.8, 5.8 Hz, 1 H), 7.56 (s, 1 H), 7.66 (dt, J=9.0, 2.4, 2.2 Hz, 2 H), 7.89 (dd, J=7.8, 1.7 Hz, 1 H), 8.03 (dt, J=9.0, 2.4, 2.2 Hz, 2 H), 8.43 (dd, J=4.7, 1.4 Hz, 1 H).

Example 112

3'-Chloro-3,6-dihydro-2H-[1,2']bipyridinyl-4-carboxylic acid (3,4,5,6-tetrahydro-2H-[1,2']bipyridinyl-5'-yl)-amide The title compound was prepared using the procedure described in Example 49D using 3,4,5,6-tetrahydro-2H-[1,2']bipyridinyl-5'-ylamine instead of 4-ter-butylaniline. MS (ESI+) m/z 398 (M+H)⁺, m/z 396 (M−H)⁻ (30%), m/z 211 (M-186)⁻ (100%); 1H NMR (300 MHz, DMSO-D6) δ ppm 1.65 (s, 6 H), 2.55 (m, 2 H), 3.46 (t, J=5.4 Hz, 2 H), 3.65 (s, 4 H), 4.04 (q, J=2.7 Hz, 2 H), 6.89 (m, 1 H), 7.01 (dd, J=7.6, 4.6 Hz, 1 H), 7.45 (d, J=9.8 Hz, 1 H), 7.83 (dd, J=7.6, 1.5 Hz, 1 H), 8.18 (dd, J=10.0, 2.5 Hz, 1 H), 8.22 (dd, J=4.7, 1.7 Hz, 1 H), 8.51 (d, J=2.4 Hz, 1 H), 10.08 (s, 1 H).

Example 113

3'-Chloro-3,6-dihydro-2H-[1,2']bipyridinyl-4-carboxylic acid (6-azepan-1-yl-pyridin-3-yl)-amide The title compound was prepared using the procedure described in Example 49D using 6-azepan-1-yl-pyridin-3-ylamine instead of 4-ter-butylaniline. MS (ESI+) m/z 412 (M+H)⁺, m/z 410 (M−H)⁻; 1H NMR (300 MHz, DMSO-D6) δ ppm 1.52 (m, 4 H), 1.77 (s, 4 H), 2.55 (m, 2 H), 3.46 (t, J=5.4 Hz, 2 H), 3.69 (m, 4 H), 4.03 (q, J=2.7 Hz, 2 H), 6.89 (m, 1 H), 7.01 (dd, J=7.8, 4.7 Hz, 1 H), 7.35 (d, J=9.5 Hz, 1 H), 7.83 (dd, J=7.8, 1.7 Hz, 1 H), 8.18 (dd, J=10.0, 2.5 Hz, 1 H), 8.22 (dd, J=4.7, 1.7 Hz, 1 H), 8.51 (d, J=2.4 Hz, 1 H), 10.08 (s, 1 H).

Example 114

3'-Chloro-3,6-dihydro-2H-[1,2']bipyridinyl-4-carboxylic acid (4-cyclopropyl-phenyl)-amide The title compound was prepared using the procedure described in Example 49D using 4-cyclopropane-aniline instead of 4-tert-butylaniline. MS (ESI+) m/z 354 (M+H)⁺, m/z 352 (M−H)⁻; 1H NMR (300 MHz, DMSO-D6) δ ppm 0.61 (m, 2 H), 0.90 (m, 2 H), 1.86 (m, 1 H), 2.55 (m, 2 H), 3.45 (t, J=5.4 Hz, 2 H), 4.00 (q, J=2.5 Hz, 2 H), 6.76 (m, 1 H), 7.00 (m, 3 H), 7.55 (m, 2 H), 7.82 (dd, J=7.8, 1.7 Hz, 1 H), 8.22 (dd, J=4.7, 1.7 Hz, 1 H), 9.63 (s, 1 H).

Example 115

1-Pyrimidin-2-yl-1,2,3,6-tetrahydro-pyridine-4-carboxylic acid (6-trifluoromethyl-pyridin-3-yl)-amide The title compound was prepared using the procedure described in Example 49D using 6-trifluoromethyl-pyridin-3-ylamine instead of 4-tert-butylaniline. MS (DCI+) m/z 350 (M+H)⁺; 1H NMR (300 MHz, DMSO-D6) δ ppm 2.48 (m, 2 H), 3.93 (t, J=5.8 Hz, 2 H), 4.40 (q, J=2.9 Hz, 2 H), 6.68 (t, J=4.7 Hz, 1 H), 6.91 (m, 1 H), 7.88 (d, J=8.5 Hz, 1 H), 8.40 (m, 3 H), 9.00 (d, J=2.4 Hz, 1 H), 10.32 (s, 1 H).

Example 116

1-Pyrimidin-2-yl-1,2,3,6-tetrahydro-pyridine-4-carboxylic acid (4-acetyl-phenyl)-amide The title compound was prepared using the procedure described in Example 52B using 4-acetyl-aniline instead of 4-tert-butylaniline. MS (DCI+) m/z 323 (M+H)⁺; 1H NMR (300 MHz, DMSO-D6) δ ppm 2.47 (m, 2 H), 2.53 (s, 3 H), 3.92 (t, J=5.8 Hz, 2 H), 4.37 (q, J=2.8 Hz, 2 H), 6.67 (t, J=4.7 Hz, 1 H), 6.84 (m, 1 H), 7.84 (m, 2 H), 7.93 (m, 2 H), 8.41 (d, J=4.7 Hz, 2 H), 10.07 (s, 1 H).

Example 117

4-[(1-Pyrimidin-2-yl-1,2,3,6-tetrahydro-pyridine-4-carbonyl)-amino]-benzoic acid methyl ester The title compound was prepared using the procedure described in Example 52B using 4-amino-benzoic acid methyl ester instead of 4-tert-butylaniline. MS (DCI+) m/z 339 (M+H)⁺; 1H NMR (300 MHz, DMSO-D6) δ ppm 2.46 (m, 2 H), 3.82 (s, 3 H), 3.92 (t, J=5.8 Hz, 2 H), 4.37 (q, J=2.7 Hz, 2 H), 6.67 (t, J=4.7 Hz, 1 H), 6.83 (m, 1 H), 7.84 (m, 2 H), 7.92 (m, 2 H), 8.41 (d, J=4.7 Hz, 2 H), 10.08 (s, 1 H).

Example 118

3'-Trifluoromethyl-3,6-dihydro-2H-[1,2']bipyridinyl-4-carboxylic acid (4-tert-butylsulfanyl-phenyl)-amide The title compound was prepared using the procedure described in Example 49D using 4-tert-butylsulfanyl-phenylamine instead of 4-tert-butylaniline. MS (DCI+) m/z 436 (M+H)⁺; 1H NMR (300 MHz, DMSO-D6) δ ppm 1.22 (s, 9

H), 2.55 (m, 2 H), 3.40 (t, J=5.6 Hz, 2 H), 3.99 (q, J=2.7 Hz, 2 H), 6.78 (m, 1 H), 7.18 (dd, J=7.8, 4.7 Hz, 1 H), 7.42 (dt, J=8.8, 2.7, 2.4 Hz, 2 H), 7.72 (dt, J=9.0, 2.4, 2.2 Hz, 2 H), 8.09 (dd, J=7.8, 2.0 Hz, 1 H), 8.52 (dd, J=4.7, 1.0 Hz, 1 H), 9.88 (s, 1 H).

Example 119

3'-Trifluoromethyl-3,6-dihydro-2H-[1,2']bipyridinyl-4-carboxylic acid (6-trifluoromethyl-pyridin-3-yl)-amide The title compound was prepared using the procedure described in Example 49D using 6-trifluoromethyl-pyrid-3-ylamine instead of 4-tert-butylaniline. MS (DCI+) m/z 417 (M+H)$^+$; 1H NMR (300 MHz, DMSO-D6) δ ppm 2.56 (m, 2 H), 3.40 (t, J=5.4 Hz, 2 H), 4.02 (q, J=2.9 Hz, 2 H), 6.90 (m, 1 H), 7.19 (dd, J=7.8, 4.7 Hz, 1 H), 7.88 (d, J=8.5 Hz, 1 H), 8.10 (dd, J=7.8, 1.7 Hz, 1 H), 8.40 (dd, J=8.3, 2.2 Hz, 1 H), 8.53 (dd, J=4.7, 1.4 Hz, 1 H), 9.01 (d, J=2.4 Hz, 1 H), 10.31 (s, 1 H).

Example 120

3'-Trifluoromethyl-3,6-dihydro-2H-[1,2']bipyridinyl-4-carboxylic acid (2,2-difluoro-benzo[1,3]dioxol-5-yl)-amide The title compound was prepared using the procedure described in Example 49D using 2,2-difluoro-benzo[1,3]dioxol-5-ylamine instead of 4-tert-butylaniline. MS (DCI+) m/z 428 (M+H)$^+$; 1H NMR (300 MHz, DMSO-D6) δ ppm 2.53 (m, 2 H), 3.39 (t, J=4.8 Hz, 2 H), 3.99 (q, J=2.7 Hz, 2 H), 6.78 (m, 1 H), 7.18 (dd, J=7.8, 4.7 Hz, 1 H), 7.35 (d, J=8.8 Hz, 1 H), 7.42 (m, 1 H), 7.82 (d, J=2.0 Hz, 1 H), 8.09 (dd, J=7.8, 1.7 Hz, 1 H), 8.52 (dd, J=4.7, 1.4 Hz, 1 H), 9.94 (s, 1 H).

Example 121

1-Pyrimidin-2-yl-1,2,3,6-tetrahydro-pyridine-4-carboxylic acid [4-(2-methyl-propane-2-sulfonyl)-phenyl]-amide The title compound was prepared using the procedure described in Example 52B using 4-(2-methyl-propane-2-sulfonyl)-phenylamine instead of 4-tert-butylaniline. MS (DCI+) m/z 401 (M+H)$^+$ (90%), m/z 231 (M-169)$^+$ (100%); 1H NMR (300 MHz, DMSO-D6) δ ppm 1.23 (s, 9 H), 2.47 (m, 2 H), 3.93 (t, J=5.6 Hz, 2 H), 4.38 (q, J=2.7 Hz, 2 H), 6.68 (t, J=4.7 Hz, 1 H), 6.86 (m, 1 H), 7.76 (m, 2 H), 7.97 (m, 2 H), 8.41 (d, J=4.7 Hz, 2 H), 10.21 (s, 1 H).

Example 122

1-Pyrimidin-2-yl-1,2,3,6-tetrahydro-pyridine-4-carboxylic acid (4-tert-butylsulfanyl-phenyl)-amide The title compound was prepared using the procedure described in Example 52B using 4-(2-methyl-propane-2-sulfanyl)-phenylamine instead of 4-tert-butylaniline. MS (DCI+) m/z 369 (M+H)$^+$; 1H NMR (300 MHz, DMSO-D6) δ ppm 1.22 (s, 9 H), 2.46 (m, 2 H), 3.92 (t, J=5.8 Hz, 2 H), 4.36 (q, J=2.7 Hz, 2 H), 6.67 (t, J=4.7 Hz, 1 H), 6.79 (m, 1 H), 7.42 (dt, J=9.1, 2.5, 2.3 Hz, 2 H), 7.71 (dt, J=9.1, 2.5, 2.3 Hz, 2 H), 8.40 (d, J=4.7 Hz, 2 H), 9.88 (s, 1 H).

Example 123

3'-Trifluoromethyl-3,6-dihydro-2H-[1,2']bipyridinyl-4-carboxylic acid [4-(2-methyl-propane-2-sulfonyl)-phenyl]-amide The title compound was prepared using the procedure described in Example 49D using 4-(2-methyl-propane-2-sulfonyl)-phenylamine instead of 4-tert-butylaniline. MS (DCI+) m/z 468 (M+H)$^+$; 1H NMR (300 MHz, DMSO-D6) δ ppm 1.23 (s, 9 H), 2.56 (m, 2 H), 3.40 (t, J=5.1 Hz, 2 H), 4.01 (m, 2 H), 6.84 (m, 1H), 7.19 (dd, J=7.8, 4.7 Hz, 1 H), 7.76 (dt, J=9.0, 2.4, 2.2 Hz, 2 H), 7.97 (dt, J=9.0, 2.4, 2.2 Hz, 2 H), 8.09 (dd, J=7.8, 1.7 Hz, 1 H), 8.53 (dd, J=4.7, 1.4 Hz, 1 H), 10.20 (s, 1 H).

Example 124

1-(4-Methoxy-pyrimidin-2-yl)-1,2,3,6-tetrahydro-pyridine-4-carboxylic acid (4-trifluoromethyl-phenyl)-amide MS (DCI+) m/z 379 (M+H)$^+$; 1H NMR (300 MHz, DMSO-D6) δ ppm 2.47 (m, 2 H), 3.87 (s, 3 H), 3.92 (t, J=5.6 Hz, 2 H), 4.39 (q, J=2.6 Hz, 2 H), 6.82 (m, 1 H), 7.68 (d, J=8.5 Hz, 3 H), 7.91 (d, J=8.5 Hz, 2 H), 8.13 (d, J=5.4 Hz, 1 H), 10.09 (s, 1 H).

Example 125

3'-Chloro-3,6-dihydro-2H-[1,2']bipyridinyl-4-carboxylic acid (4-trifluoromethanesulfonyl-phenyl)-amide The title compound was prepared using the procedure described in Example 49D using 4-(trifluoromthyl-sulfonyl)-phenylamine instead of 4-tert-butylaniline. MS (ESI+) m/z 446 (M+H)$^+$, m/z 444 (M−H)$^-$; 1H NMR (300 MHz, CHLOROFORM-D) δ ppm 2.70 (m, 2 H), 3.60 (t, J=5.4 Hz, 2 H), 4.15 (q, J=3.1 Hz, 2 H), 6.88 (m, 2 H), 7.65 (dd, J=7.8, 1.7 Hz, 1 H), 7.81 (m, 1 H), 7.90 (m, 2 H), 8.00 (m, 2 H), 8.19 (dd, J=4.7, 1.7 Hz, 1 H).

Example 126

3'-Chloro-3,6-dihydro-2H-[1,2']bipyridinyl-4-carboxylic acid [4-(2,2,2-trifluoro-1-hydroxy-1-trifluoromethyl-ethyl)-phenyl]-amide The title compound was prepared using the procedure described in Example 49D using 4-(2,2,2-trifluoro-1-hydroxy-1-trifluoromethyl-ethyl)-phenylamine instead of 4-tert-butylaniline. MS (ESI+) m/z 480 (M+H)$^+$, m/z 478 (M−H)$^-$; 1H NMR (300 MHz, CHLOROFORM-D) δ ppm 2.68 (m, 2 H), 3.45 (s, 1 H), 3.67 (t, J=5.8 Hz, 2 H), 4.18 (q, J=2.7 Hz, 2 H), 6.81 (m, 1 H), 6.93 (dd, J=7.8, 5.1 Hz, 1 H), 7.71 (m, 6 H), 8.23 (dd, J=4.9, 1.5 Hz, 1 H).

Example 127

3'-Chloro-3,6-dihydro-2H-[1,2']bipyridinyl-4-carboxylic acid [4-(2,2-dichloro-1-methyl-cyclopropyl)-phenyl]-amide The title compound was prepared using the procedure described in Example 49D using 4-(2,2-dichloro-1-methyl-cyclopropyl)-phenylamine instead of 4-tert-butylaniline.

MS (DCI+) m/z 436 (M+H)$^+$ (70%), m/z 252 (M-183)$^+$ (100%); 1H NMR (300 MHz, DMSO-D6) δ ppm 1.61 (s, 3 H), 1.74 (d, J=7.5 Hz, 1 H), 2.14 (d, J=7.8 Hz, 1 H), 2.56 (m, 2 H), 3.45 (t, J=5.4 Hz, 2 H), 4.01 (q, J=3.0 Hz, 2 H), 6.77 (m, 1 H), 7.00 (dd, J=7.6, 4.6 Hz, 1 H), 7.27 (m, 2 H), 7.67 (m, 2 H), 7.83 (dd, J=7.6, 1.5 Hz, 1 H), 8.22 (dd, J=4.7, 1.7 Hz, 1 H), 9.75 (s, 1 H).

Example 128

3'-Chloro-3,6-dihydro-2H-[1,2']bipyridinyl-4-carboxylic acid [4-(cyano-dimethyl-methyl)-phenyl]-amide The title compound was prepared using the procedure described in Example 49D using 4-(cyano-dimethyl-methyl)-phenylamine instead of 4-tert-butylaniline. MS (DCI+) m/z 381 (M+H)$^+$; 1H NMR (300 MHz, CHLOROFORM-D) δ ppm 1.72 (s, 6 H), 2.69 (m, 2 H), 3.59 (t, J=5.6 Hz, 2 H), 4.12 (q, J=2.9 Hz, 2 H), 6.80 (m, 1 H), 6.87 (dd, J=7.8, 4.7 Hz, 1 H), 7.45 (m, 2 H), 7.49 (s, 1 H), 7.59 (m, 2 H), 7.63 (dd, J=7.6, 1.5 Hz, 1 H), 8.19 (dd, J=4.7, 1.7 Hz, 1 H).

Example 129

3'-Trifluoromethyl-3,6-dihydro-2H-[1,2']bipyridinyl-4-carboxylic acid [4-(cyano-dimethyl-methyl)-phenyl]-amide The title compound was prepared using the procedure described in Example 49D using 4-(cyano-dimethyl-methyl)-phenylamine instead of 4-tert-butylaniline. MS (ESI+) m/z 415 (M+H)$^+$, m/z 414 (M–H)$^-$ (18%), m/z 212 (M-202)$^-$ (100%); 1H NMR (300 MHz, CHLOROFORM-D) δ ppm 1.72 (s, 6 H), 2.67 (m, 2 H), 3.53 (t, J=5.4 Hz, 2 H), 4.07 (q, J=3.1 Hz, 2 H), 6.79 (m, 1 H), 7.00 (dd, J=7.8, 4.7 Hz, 1 H), 7.45 (m, 3 H), 7.59 (m, 2 H), 7.89 (dd, J=7.8, 2.0 Hz, 1 H), 8.43 (dd, J=4.7, 2.0 Hz, 1 H).

Example 130

3'-Trifluoromethyl-3,6-dihydro-2H-[1,2']bipyridinyl-4-carboxylic acid (3-chloro-4-trifluoromethylsulfanyl-phenyl)-amide The title compound was prepared using the procedure described in Example 49D using 3-chloro-4-trifluoromethylsulfanyl-phenylamine instead of 4-tert-butylaniline. MS (DCI+) m/z 482 (M+H)$^+$ (45%), m/z 283 (M-198)$^+$ (100%); 1H NMR (300 MHz, DMSO-D6) δ ppm 2.54 (m, 2 H), 3.39 (t, J=5.4 Hz, 2 H), 4.00 (q, J=2.4 Hz, 2 H), 6.85 (m, 1 H), 7.19 (dd, J=8.0, 4.6 Hz, 1 H), 7.81 (d, J=2.0 Hz, 1 H), 7.83 (s, 1 H), 8.09 (dd, J=8.0, 1.5 Hz, 1 H), 8.16 (d, J=2.0 Hz, 1 H), 8.53 (dd, J=4.7, 1.4 Hz, 1 H), 10.19 (s, 1 H).

Example 131

3'-Chloro-3,6-dihydro-2H-[1,2']bipyridinyl-4-carboxylic acid [4-(8-aza-bicyclo[3.2.1]oct-8-yl)-3,5-difluoro-phenyl]-amide The title compound was prepared using the procedure described in Example 49D using 4-(8-aza-bicyclo[3.2.1]oct-8-yl)-3,5-difluoro-phenylamine instead of 4-tert-butylaniline. MS (ESI+) m/z 459 (M+H)$^+$, m/z 457 (M–H)$^-$; 1H NMR (300 MHz, DMSO) δ ppm 1.52 (m, 3 H), 1.89 (m, 7 H), 2.61 (m, 2 H), 3.53 (t, J=5.4 Hz, 2 H), 4.05 (m, 4 H), 6.75 (m, 1 H), 6.94 (dd, J=7.8, 4.7 Hz, 1 H), 7.22 (m, 2 H), 7.73 (dd, J=7.8, 1.7 Hz, 1 H), 8.16 (dd, J=4.7, 1.7 Hz, 1 H).

Example 132

3'-Trifluoromethyl-3,6-dihydro-2H-[1,2']bipyridinyl-4-carboxylic acid (4-tert-butyl-2-chloro-phenyl)-amide The title compound was prepared using the procedure described in Example 49D using 2-chloro-4-tert-butyl-phenylamine instead of 4-tert-butylaniline. MS (ESI+) m/z 438 (M+H)$^+$, m/z 436 (M–H)$^-$; 1H NMR (300 MHz, CHLOROFORM-D) δ ppm 1.30 (s, 9 H), 2.69 (m, 2 H), 3.55 (t, J=5.4 Hz, 2 H), 4.10 (q, J=3.1 Hz, 2 H), 6.86 (m, 1 H), 6.98 (dd, J=7.3, 5.3 Hz, 1 H), 7.31 (dd, J=8.8, 2.4 Hz, 1 H), 7.38 (d, J=2.4 Hz, 1 H), 7.89 (dd, J=7.8, 1.7 Hz, 1 H), 7.97 (s, 1 H), 8.34 (d, J=8.8 Hz, 1 H), 8.43 (dd, J=4.9, 1.5 Hz, 1 H).

Example 133

1-Thiazol-2-yl-1,2,3,6-tetrahydro-pyridine-4-carboxylic acid (4-trifluoromethanesulfonyl-phenyl)-amide Example 133A 1-Thiazol-2-yl-1,2,3,6-tetrahydro-pyridine-4-carboxylic acid A mixture of 2-bromooxazole (4.98 mmol), and isoguvacine, sodium salt (1.2 g, 8.2 mmol) in water (7 mL) was heated to 90° C. and stirred for 4 hour. Additional isoguvacine, sodium salt (0.52 g, 3.3 mmol) was then added and stirred overnight. The mixture was diluted with water and extracted with CH$_2$Cl$_2$. The aqueous layer was acidified with conc HCl (pH~3) and extracted with CHCl$_3$. The organic layer was dried (Na$_2$SO$_4$) and concentrated under reduced pressure to provide 1-Thiazol-2-yl-1,2,3,6-tetrahydro-pyridine-4-carboxylic acid a solid.

Example 133B

1-Thiazol-2-yl-1,2,3,6-tetrahydro-pyridine-4-carboxylic acid (4-trifluoromethanesulfonyl-phenyl)-amide The title compound was prepared using the procedure described in Example 52D using 4-trifluoromethanesulfonyl-phenylamine instead of 4-tert-butylaniline. MS (DCI+) m/z 418 (M+H)$^+$ (40%), m/z 243 (M-174)$^+$ (100%); 1H NMR (300 MHz, DMSO-D6) δ ppm 2.55 (m, 2 H), 3.63 (t, J=5.8 Hz, 2 H), 4.15 (q, J=2.5 Hz, 2 H), 6.87 (d, J=3.4 Hz, 2 H), 7.20 (d, J=3.4 Hz, 1 H), 8.10 (m, 4 H), 10.52 (s, 1 H).

Example 134

1-Thiazol-2-yl-1,2,3,6-tetrahydro-pyridine-4-carboxylic acid (4-tert-butyl-phenyl)-amide The title compound was prepared using the procedure described in Example 52D. MS (DCI+) m/z 342 (M+H)$^+$; 1H NMR (300 MHz, DMSO-D6) δ ppm 1.26 (s, 9 H), 2.53 (m, 2 H), 3.62 (t, J=5.8 Hz, 2 H), 4.10 (q, J=2.7 Hz, 2 H), 6.74 (m, 1 H), 6.86 (d, J=3.7 Hz, 1 H), 7.20 (d, J=3.7 Hz, 1 H), 7.32 (d, J=8.8 Hz, 2 H), 7.58 (d, J=8.8 Hz, 2 H), 9.71 (s, 1 H).

Example 135

3'-Trifluoromethyl-3,6-dihydro-2H-[1,2']bipyridinyl-4-carboxylic acid (4-dimethylsulfamoyl-phenyl)-amide The title compound was prepared using the procedure described in Example 52D using 4-dimethylsulfamoyl-phenylamine instead of 4-tert-butylaniline. MS (ESI+) m/z 455 (M+H)$^+$, m/z 453 (M–H)$^-$; 1H NMR (300 MHz, CHLOROFORM-D) δ ppm 2.68 (m, 2 H), 2.71 (s, 6 H), 3.53 (t, J=5.4 Hz, 2 H), 4.09 (q, J=2.9 Hz, 2 H), 6.83 (m, 1 H), 7.02 (dd, J=7.8, 4.7 Hz, 1 H), 7.65 (s, 1 H), 7.76 (s, 4 H), 7.91 (dd, J=7.8, 1.7 Hz, 1 H), 8.44 (dd, J=4.6, 1.5 Hz, 1 H).

Example 136

3'-Trifluoromethyl-3,6-dihydro-2H-[1,2']bipyridinyl-4-carboxylic acid [4-(piperidine-1-sulfonyl)-phenyl]-amide The title compound was prepared using the procedure described in Example 52D using 4-(piperidine-1-sulfonyl 4-(piperidine-1-sulfonyl-phenylamine instead of 4-tert-butylaniline. MS (ESI+) m/z 495 (M+H)$^+$, m/z 493 (M–H)$^-$; 1H NMR (300 MHz, CHLOROFORM-D) δ ppm 1.44 (m, 2 H), 1.64 (m, 4 H), 2.68 (m, 2 H), 2.98 (t, J=5.4 Hz, 4 H), 3.54 (t, J=5.6 Hz, 2 H), 4.10 (q, J=2.8 Hz, 2 H), 6.82 (m, 1H), 7.02 (dd, J=7.5, 4.4 Hz, 1 H), 7.67 (m, 1 H), 7.74 (s, 4 H), 7.92 (dd, J=7.8, 1.7 Hz, 1 H), 8.44 (dd, J=5.1, 1.4 Hz, 1 H).

Example 137

3'-Trifluoromethyl-3,6-dihydro-2H-[1,2']bipyridinyl-4-carboxylic acid (5-iodo-pyridin-2-yl)-amide The title compound was prepared using the procedure described in Example 52D using 5-iodo-pyridin-2-ylamine instead of 4-tert-butylaniline. MS (ESI+) m/z 475 (M+H)$^+$, m/z 473 (M–H)$^-$; 1H NMR (300 MHz, CHLOROFORM-D) δ ppm 2.67 (m, 2 H), 3.51 (t, J=5.4 Hz, 2 H), 4.07 (q, J=3.1 Hz, 2 H), 6.86 (m, 1 H), 6.99 (dd, J=7.8, 4.7 Hz, 1 H), 7.89 (dd, J=7.8, 2.0 Hz, 1 H), 7.98 (dd, J=8.8, 2.4 Hz, 1 H), 8.15 (m, 2 H), 8.42 (dd, J=4.7, 1.4 Hz, 1 H), 8.47 (d, J=1.7 Hz, 1 H).

Example 138

3'-Trifluoromethyl-3,6-dihydro-2H-[1,2']bipyridinyl-4-carboxylic acid (3,4-difluoro-phenyl)-amide The title compound was prepared using the procedure described in Example 52D using 3,4-difluoro-phenylamine instead of 4-tert-butylaniline. MS (ESI+) m/z 384 (M+H)$^+$, m/z 382 (M–H)$^-$; 1H NMR (300 MHz, CHLOROFORM-D) δ ppm 2.65 (m, 2 H), 3.52 (t, J=5.6 Hz, 2 H), 4.07 (q, J=3.1 Hz, 2 H), 6.78 (m, 1 H), 7.00 (dd, J=7.8, 4.7 Hz, 1 H), 7.12 (m, 2 H), 7.41 (s, 1 H), 7.68 (m, 1 H), 7.90 (dd, J=7.8, 1.7 Hz, 1 H), 8.43 (dd, J=4.7, 1.4 Hz, 1 H).

Example 139

3'-Chloro-3,6-dihydro-2H-[1,2']bipyridinyl-4-carboxylic acid (4-methanesulfonyl-phenyl)-amide The title compound was prepared using the procedure described in Example 49D using 4-methanesulfonyl-phenylamine instead of 4-tert-butylaniline. MS (DCI+) m/z 392 (M+H)$^+$ (20%), m/z 206 (M-185)$^+$ (100%); 1H NMR (300 MHz, DMSO-D6) δ ppm 2.57 (m, 2 H), 3.17 (s, 3 H), 3.46 (t, J=5.4 Hz, 2 H), 4.04 (q, J=2.8 Hz, 2 H), 6.87 (m, 1 H), 7.01 (dd, J=7.8, 4.7 Hz, 1 H), 7.85 (m, 4 H), 7.96 (dt, J=9.0, 2.4, 2.2 Hz, 2 H), 8.23 (dd, J=4.6, 1.5 Hz, 1 H).

Example 140

3'-Dimethylsulfamoyl-3,6-dihydro-2H-[1,2']bipyridinyl-4-carboxylic acid (4-tert-butyl-phenyl)-amide

Example 140A

2-Chloro-pyridine-3-sulfonic acid dimethylamide

A solution of Me$_2$NH in THF (2M, 8 mL, 16 mmol) was added to 3-(2-chloropyridyl)sulfonyl chloride (J. Med. Chem. 1980, 23, 1376) (2.1 g, 9.9 mmol) in THF (10 mL), and stirred 10 hours, quenched with sat aq NH$_4$Cl, extracted with EtOAc, and purified by flash chromatography (30% EtOAc/Hex) to provide sulfonamide as a red oil

Example 140B

1-Thiazol-2-yl-1,2,3,6-tetrahydro-pyridine-4-carboxylic acid

A solution of 2-chloro-pyridine-3-sulfonic acid dimethylamide (1.18 mmol) and isoguvacine, sodium salt (2.19 mmol) in THF (0.5 mL) and water (2 mL) was stirred at 90° C. for 22 hours, acidified (pH~1) with TFA, and extracted with CH$_2$Cl$_2$. The organic layer was dried (Na$_2$SO$_4$), concentrated, and purified by flash chromatography (5% MeOH/CH$_2$Cl$_2$) and trituration (Et$_2$O) to provide as a white solid. $^1$H NMR (300 MHz, CD$_3$OD) δ 8.47 (dd, J=1.7, 4.8 Hz, 1H), 8.22 (dd, J=1.7, 7.8 Hz, 1H), 7.22 (dd, J=4.8, 7.8 Hz, 1H), 7.03 (sept, J=1.7 Hz, 1H), 3.99 (q, J=3.0 Hz, 2H), 3.40 (t, J=5.6 Hz, 2H), 2.73 (s, 6H), 2.56 (m, 2H).

Example 140C

3'-Dimethylsulfamoyl-3,6-dihydro-2H-[1,2']bipyridinyl-4-carboxylic acid (4-tert-butyl-phenyl)-amide The title compound was prepared using the procedure described in Example 52D using 4-tert-butylaniline. MS (ESI+) m/z 443 (M+H)$^+$, m/z 441 (M–H)$^-$; 1H NMR (300 MHz, CHLOROFORM-D) δ ppm 1.31 (s, 9 H), 2.73 (s, 2 H), 2.77 (s, 6 H), 3.56 (t, J=5.6 Hz, 2 H), 4.08 (q, J=2.9 Hz, 2 H), 6.84 (m, 1 H), 7.10 (dd, J=7.8, 4.7 Hz, 1 H), 7.36 (m, 2 H), 7.39 (d, J=2.0 Hz, 1 H), 7.49 (m, 2 H), 8.18 (dd, J=8.0, 1.9 Hz, 1 H), 8.45 (dd, J=4.7, 2.0 Hz, 1 H).

Example 141

3'-Dimethylsulfamoyl-3,6-dihydro-2H-[1,2']bipyridinyl-4-carboxylic acid (4-chloro-phenyl)-amide The title compound was prepared using the procedure described in Example 52D using 4-chloro-phenylamine instead of 4-tert-butylaniline. MS (ESI+) m/z 421 (M+H)$^+$, m/z 419 (M–H)$^-$; 1H NMR (300 MHz, CHLOROFORM-D) δ ppm 2.72 (s, 2 H), 2.77 (s, 6 H), 3.56 (t, J=5.4 Hz, 2 H), 4.08 (d, J=2.4 Hz, 2 H), 6.86 (s, 1 H), 7.10 (dd, J=8.0, 4.6 Hz, 1 H), 7.31 (d, J=8.8 Hz, 2 H), 7.43 (s, 1H), 7.54 (d, J=9.2 Hz, 2 H), 8.17 (dd, J=7.8, 1.4 Hz, 1 H), 8.45 (dd, J=4.6, 1.5 Hz, 1 H).

Example 142

3'-Dimethylsulfamoyl-3,6-dihydro-2H-[1,2']bipyridinyl-4-carboxylic acid (4-trifluoromethoxy-phenyl)-amide The title compound was prepared using the procedure described in Example 52D using 4-trifluoromethoxy-phenylamine instead of 4-tert-butylaniline. MS (ESI+) m/z 471 $(M+H)^+$, m/z 469 $(M-H)^-$; 1H NMR (300 MHz, CHLOROFORM-D) δ ppm 2.72 (s, 2 H), 2.77 (s, 6 H), 3.57 (t, J=5.3 Hz, 2 H), 4.09 (s, 2 H), 6.87 (s, 1 H), 7.11 (dd, J=7.8, 4.4 Hz, 1 H), 7.20 (d, J=8.1 Hz, 2 H), 7.48 (s, 1 H), 7.62 (d, J=8.8 Hz, 2 H), 8.18 (d, J=7.5 Hz, 1 H), 8.46 (d, J=3.7 Hz, 1 H).

(5) Biological Data (a) In Vitro Data—Determination of Inhibition Potencies

Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 mg/1 Na pyruvate, without phenol red), L-glutamine, hygromycin B, and Lipofectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy) methyl ester) was purchased from Molecular Probes (Eugene, Oreg.).

The cDNAs for the human VR1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. *Pain Vol.* 88 pages 205-215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hVR1 cDNA were transfected individually into 1321N1 human astrocytoma cells using Lipofectamine™. Forty-eight hours after transfection, the neomycin-resistant cells were selected with growth medium containing 800 µg/mL Geneticin (Gibco BRL). Surviving individual colonies were isolated and screened for VR1 receptor activity. Cells expressing recombinant homomeric VR1 receptors were maintained at 37° C. in D-MEM containing 4 mM L-glutamine, 300 µg/mL G418 (Cal-biochem) and 10% fetal bovine serum under a humidified 5% $CO_2$ atmosphere.

The functional activity of compounds at the VR1 receptor was determined with a $Ca^{2+}$ influx assay and measurement of intracellular $Ca^{2+}$ levels ($[Ca^{2+}]i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 µM solution of the VR1 agonist capsaicin was also prepared in D-PBS. The fluorescent $Ca^{2+}$ chelating dye fluo-4 was used as an indicator of the relative levels of $[Ca^{2+}]i$ in a 96-well format using a Fluorescence Imaging Plate Reader (FLIPR)(Molecular Devices, Sunnyvale, Calif.). Cells were grown to confluency in 96-well black-walled tissue culture plates. Then, prior to the assay, the cells were loaded with 100 µL per well of fluo-4 AM (2 µM, in D-PBS) for 1-2 hours at 23° C. Washing of the cells was performed to remove extracellular fluo-4 AM (2×1 mL D-PBS per well), and afterward, the cells were placed in the reading chamber of the FLIPR instrument. 50 µL of the compound solutions were added to the cells at the 10 second time mark of the experimental run. Then, after a 3 minute time delay, 50 µL of the capsaicin solution was added at the 190 second time mark (0.05 µM final concentration)(final volume=200 µL) to challenge the VR1 receptor. Time length of the experimental run was 240 seconds. Fluorescence readings were made at 1 to 5 second intervals over the course of the experimental run. The peak increase in relative fluorescence units (minus baseline) was calculated from the 190 second time mark to the end of the experimental run, and expressed as a percentage of the 0.05 µM capsaicin (control) response. Curve-fits of the data were solved using a four-parameter logistic Hill equation in GraphPad Prism® (GraphPad Software, Inc., San Diego, Calif.), and $IC_{50}$ values were calculated.

The compounds of the present invention were found to be antagonists of the vanilloid receptor subtype 1 (VR1) receptor with $IC_{50s}$ from about 2200 nM to about 0.5 nM. In a preferred range, compounds tested had $IC_{50s}$ from about 200 nM to about 1.0 nM.

(a) In Vivo Data—Analgesic Effects

Experiments were performed on 400 adult male 129J mice (Jackson Laboratories, Bar Harbor, Me.), weighing 20-25 g and male Sprague-Dawley rats (Charles River, Wilmington, Mass.) weighing 200-300 grams were utilized. Animals were kept in a vivarium, maintained at 22° C., with a 12 hour alternating light-dark cycle with food and water available ad libitum. All experiments were performed during the light cycle. Animals were randomly divided into separate groups of 6 animals each. Each animal was used in one experiment only and was sacrificed immediately following the completion of the experiment. All animal handling and experimental procedures were approved by an IACUC Committee.

The antinociceptive test used was a modification of the abdominal constriction assay described in Collier, et al., Br. J. Pharmacol. Chemother. 32 (1968) 295-310. Each animal received an intraperitoneal (i.p.) injection of 0.3 mL of 0.6% acetic acid in normal saline to evoke writhing. Animals were placed separately under clear cylinders for the observation and quantification of abdominal constriction. Abdominal constriction was defined as a mild constriction and elongation passing caudally along the abdominal wall, accompanied by a slight twisting of the trunk and followed by bilateral extension of the hind limbs. The total number of abdominal constrictions was recorded from 5 to 20 minutes after acetic acid injection. The $ED_{50s}$ were determined based on the i.p. injection.

The other antinociceptive test used was Complete Freund's Adjuvant-induced Thermal Hyperalgesia (CFA) assay described in Pircio et al. (*Eur J Pharmacol. Vol.* 31(2) pages 207-15, 1975). Chronic inflammatory hyperalgesia was induced in one group of rats following the injection of complete Freund's adjuvant (CFA, 50%, 150 ul) into the plantar surface of the right hindpaw 48 hours prior to testing.

Thermal nociceptive thresholds were measured in three different groups of rats. The $ED_{50s}$ were determined based on the oral administration.

The compounds of the present invention tested were found to have antinociceptive effects with $ED_{50s}$ from about 1 mg/kg to about 500 mg/kg.

The in vitro and in vivo data demonstrates that compounds of the present invention antagonize the VR1 receptor and are useful for treating pain.

Compounds of the present invention are also useful for ameliorating or preventing additional disorders such as, but not limited to, inflammatory thermal hyperalgesia, bladder overactivity, and urinary incontinence as described by Nolano, M. et al., Pain 81 (1999) 135; Caterina, M. J. and Julius, D., Annu. Rev. Neurosci. 24, (2001) 487-517; Caterina, M. J. et al., Science 288 (2000) 306-313; Caterina, M. J. et al., Nature 389 (1997) 816-824; Fowler, C. Urology 55 (2000) 60; and Davis, J. et al., Nature 405 (2000) 183-187.

The present invention also provides pharmaceutical compositions that comprise compounds of the present invention. The pharmaceutical compositions comprise compounds of the present invention formulated together with one or more non-toxic pharmaceutically acceptable carriers.

The pharmaceutical compositions of this invention can be administered to humans and other mammals orally, rectally, parenterally, intracisternally, intravaginally, topically (as by powders, ointments or drops), bucally or as an oral or nasal spray. The term "parenterally," as used herein, refers to modes of administration, which include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable carrier or excipient, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants that may be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutically acceptable salt," as used herein, means salts derived from inorganic or organic acids. The salts can be prepared in situ during the final isolation and purification of compounds of formula (I-VII) or separately by reacting the free base of a compound of formula (I-VII) with an inorganic or organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, dihydrochloride, hydrobromide, hydroiodide, 2-hydroxyethansulfonate (isethionate), lactate, maleate, fumarate, methanesulfonate, nicotinate, 2-naphthalenesulfonate, oxalate, pamoate, pectinate, persulfate, 3-phenylpropionate, picrate, pivalate, propionate, succinate, sulfate, (L) tartrate, (D) tartrate, (DL) tartrate, thiocyanate, phosphate, glutamate, bicarbonate, p-toluenesulfonate, and undecanoate.

The term "pharmaceutically acceptable ester," as used herein, means esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula (I-VII) may be prepared according to conventional methods.

The term "pharmaceutically acceptable amide," as used herein, means to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I-VII) may be prepared according to conventional methods.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like. Prodrugs of the present invention may be rapidly transformed in vivo to compounds of formula (I-VII), for example, by hydrolysis in blood.

The present invention contemplates compounds of formula (I-VII) formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The total daily dose of the compounds of this invention administered to a human or lower animal may range from about 0.01 to about 150 mg/kg/day. For purposes of oral administration, more preferable doses can be in the range of from about 0.1 to about 150 mg/kg/day. If desired, the effective daily dose can be divided into multiple doses for purposes of administration; consequently, single dose compositions may contain such amounts or submultiples thereof to make up the daily dose.

What is claimed is:

1. A compound of formula (VII)

(VII)

wherein
$X_1$ is N or $CR_1$;
$X_5$ is N or $CR_5$;
$X_6$ is a bond or $CR_6$;
$X_7$ is N or $CR_7$;
$X_8$ is N or $CR_8$;
$X_9$ is N or $CR_9$;
$R_1$, $R_5$, and $R_9$ are independently selected from the group consisting of hydrogen, alkyl, alkoxy, halogen, haloalkyl and heterocycle;
$R_7$ is hydrogen, alkenyl, alkoxy, alkoxycarbonyl, alkoxysulfonyl, alkyl, alkylcarbonyl, alkoxycarbonylalkyl, alkylsulfonyl, alkylthio, alkynyl, aryl, arylalkyl, aryloxy, arylthio, cyanoalkyl, cycloalkyl, cycloalkylalkyl, cycloalkyloxy, cycloalkylthio, haloalkoxy, haloalkyl, haloalkylsulfonyl, haloalkylthio, halogen, heteroaryl, heteroarylalkyl, heteroaryloxy, heteroarylthio, heterocycle, heterocyclealkyl, hydroxy, hydroxyalkyl, $R_CR_DN-$, $(R_AR_BN)$carbonyl-, $(R_AR_BN)$sulfonyl-; or $R_AS(O)_2-$;
$R_6$ and $R_8$ are independently hydrogen, lower alkenyl, lower alkoxy, lower alkyl, lower alkylthio, lower alkynyl, lower haloalkoxy, lower haloalkyl, lower haloalkylthio, halogen, hydroxy, mercapto, or $R_AR_BN-$;
$R_A$ and $R_B$ are independently alkyl, hydrogen, haloalkyl, or heterocycle; and
$R_C$ and $R_D$ are independently hydrogen, alkenyl, alkoxycarbonyl, alkyl, alkylcarbonyl, alkynyl, or $(NR_AR_B)$ carbonyl.

2. A compound according to claim 1, wherein
$X_1$ is $CR_1$;
$X_5$ is $CR_5$;
$X_6$ is $CR_6$;
$X_7$ is $CR_7$;
$X_8$ is $CR_8$;
$X_9$ is N or $CR_9$;
$R_7$ and $R_8$ are independently selected from the group consisting of hydrogen, alkyl, and halogen.

3. A compound according to claim 2, that is
3'-Chloro-3,6-dihydro-2H-[1,2']bipyridinyl-4-carboxylic acid (5-fluoro-pyridin-2-yl)-amide;
3'-Chloro-3,6-dihydro-2H-[1,2']bipyridinyl-4-carboxylic acid (5-chloro-pyridin-2-yl)-amide;
3'-Chloro-3,6-dihydro-2H-[1,2']bipyridinyl-4-carboxylic acid (5-bromo-pyridin-2-yl)-amide;
3'-Chloro-3,6-dihydro-2H-[1,2']bipyridinyl-4-carboxylic acid (5-iodo-pyridin-2-yl)-amide; or
3'-Trifluoromethyl-3,6-dihydro-2H-[1,2']bipyridinyl-4-carboxylic acid (5-iodo-pyridin-2-yl)-amide.

4. The compound according to claim 1, wherein
$X_1$ is $CR_1$;
$X_5$ is $CR_5$;
$X_6$ is $CR_6$;
$X_7$ is $CR_7$;
$X_8$ is N;
$X_9$ is $CR_9$;
$R_5$, $R_6$, $R_9$ and $R_1$ are independently selected from the group consisting of hydrogen, alkyl, haloalkyl, and halogen;
$R_7$ is hydrogen, alkenyl, alkoxy, alkoxycarbonyl, alkoxysulfonyl, alkyl, alkylcarbonyl, alkoxycarbonylalkyl, alkylsulfonyl, alkylthio, alkynyl, aryl, arylalkyl, aryloxy, arylthio, cyanoalkyl, cycloalkyl, cycloalkylalkyl, cycloalkyloxy, cycloalkylthio, haloalkoxy, haloalkyl, haloalkylsulfonyl, haloalkylthio, halogen, heteroaryl, heteroarylalkyl, heteroaryloxy, heteroarylthio, heterocycle, heterocyclealkyl, hydroxy, hydroxyalkyl, $R_CR_DN-$, $(R_AR_BN)$carbonyl-, $(R_AR_BN)$sulfonyl-; or $R_AS(O)_2-$;
$R_A$ and $R_B$ are independently alkyl, hydrogen, haloalkyl, or heterocycle; and
$R_C$ and $R_D$ are independently hydrogen, alkenyl, alkoxycarbonyl, alkyl, alkylcarbonyl, alkynyl, or $(NR_AR_B)$ carbonyl-.

5. A compound according to claim 4, that is
3'-Chloro-3,6-dihydro-2H-[1,2']bipyridinyl-4-carboxylic acid (6-trifluoromethyl-pyridin-3-yl)-amide;
3'-Chloro-3,6-dihydro-2H-[1,2']bipyridinyl-4-carboxylic acid (6-chloro-pyridin-3-yl)-amide;
3'-Chloro-3,6-dihydro-2H-[1,2']bipyridinyl-4-carboxylic acid (3,4,5,6-tetrahydro-2H-[1,2']bipyridinyl-5'-yl)-amide;
3'-Chloro-3,6-dihydro-2H-[1,2']bipyridinyl-4-carboxylic acid (6-azepan-1-yl-pyridin-3-yl)-amide; or
3'-Trifluoromethyl-3,6-dihydro-2H-[1,2']bipyridinyl-4-carboxylic acid (6-trifluoromethyl-pyridin-3-yl)-amide.

6. The compound according to claim 1, wherein
$X_1$ is $CR_1$;
$X_5$ is $CR_5$;
$X_6$ is a bond;
$X_7$ is N;
$X_8$ is N;
$X_9$ is $CR_9$;
$R_1$, $R_9$ and $R_5$, are independently selected from the group consisting of hydrogen, alkyl, haloalkyl, and halogen.

7. The compound according to claim 6, that is 3'-Chloro-3,6-dihydro-2H-[1,2']bipyridinyl-4-carboxylic acid (1-tert-butyl-1H-pyrazol-4-yl)-amide.

8. A compound according to claim 1, wherein
$X_1$ is N;
$X_5$ is $CR_5$;
$X_6$ is $CR_6$;
$X_7$ is $CR_7$;
$X_8$ is N;
$X_9$ is $CR_9$;
$R_6$, $R_7$, $R_9$ and $R_5$, are independently selected from the group consisting of hydrogen, alkyl, haloalkyl, and halogen.

9. A compound according to claim 8, that is 1-pyrimidin-2-yl-1,2,3,6-tetrahydro-pyridine-4-carboxylic acid (6-trifluoromethyl-pyridin-3-yl)-amide.

10. A pharmaceutical composition comprising a therapeutically effective amount of a compound of formula (VII) according to claim 1 or a pharmaceutically acceptable salt thereof and a pharmaceutically acceptable carrier.

11. A method of treating pain in a mammal, comprising administering a therapeutically effective amount of a compound of formula (VII) according to claim 1 or a pharmaceutically acceptable salt thereof.

* * * * *